United States Patent
Golz et al.

(10) Patent No.: US 8,088,584 B2
(45) Date of Patent: Jan. 3, 2012

(54) LTBP2 AS A BIOMARKER AND DIAGNOSTIC TARGET

(75) Inventors: Stefan Golz, Essen (DE); Holger Summer, Wuppertal (DE); Andreas Geerts, Wuppertal (DE); Ulf Brüggemeier, Leichlingen (DE); Barbara Albrecht-Küpper, Wülfrath (DE); Martina Klein, Düsseldorf (DE); Sonja Steppan, Neu-Isenburg (DE); Peter Ellinghaus, Melle (DE); Donatella D'Urso, Düsseldorf (DE); Michael Seewald, Berlin (DE); Hendrik Milting, Bad Oeynhausen (DE)

(73) Assignee: Bayer Schering Pharma Aktiengesellschaft, Berlin (DE)

(*) Notice: Subject to any disclaimer, the term of this patent is extended or adjusted under 35 U.S.C. 154(b) by 0 days.

(21) Appl. No.: 12/444,596

(22) PCT Filed: Oct. 2, 2007

(86) PCT No.: PCT/EP2007/008558
§ 371 (c)(1),
(2), (4) Date: Jul. 10, 2009

(87) PCT Pub. No.: WO2008/046509
PCT Pub. Date: Apr. 24, 2008

(65) Prior Publication Data
US 2010/0028264 A1 Feb. 4, 2010

(30) Foreign Application Priority Data
Oct. 16, 2006 (EP) .................... 06021595

(51) Int. Cl.
*C12Q 1/68* (2006.01)
*C07K 14/47* (2006.01)
*C07H 21/04* (2006.01)

(52) U.S. Cl. ........ 435/6.17; 530/350; 530/841; 536/23.5
(58) Field of Classification Search ................. None
See application file for complete search history.

(56) References Cited

U.S. PATENT DOCUMENTS
2003/0224989 A1 12/2003 Quinn et al.
2010/0028264 A1* 2/2010 Golz et al. ............... 424/9.4

FOREIGN PATENT DOCUMENTS
WO    WO 03/032813    4/2003
WO    WO 2004/069870    8/2004

OTHER PUBLICATIONS
Hirani et al 2007. Matrix Biology. 26(4): 213-223.*
Feroze-Merzoug et al. (Cancer and Metastasis Rev 20: 165-171, 2001).*

(Continued)

*Primary Examiner* — Bridget E Bunner
*Assistant Examiner* — Zachary Howard
(74) *Attorney, Agent, or Firm* — Banner & Witcoff, Ltd.

(57) ABSTRACT

The invention provides LTBP2, which is associated with cardiovascular diseases, hematological diseases, neurological diseases, cancer, endocrinological diseases, and urological diseases. The invention also provides assays for the identification of compounds useful in the treatment or prevention of cardiovascular diseases, hematological diseases, neurological diseases, cancer, endocrinological diseases, and urological diseases. The invention also features compounds which bind to and/or activate or inhibit the activity of LTBP2 as well as pharmaceutical compositions comprising such compounds. The invention also provides LTBP2 as a biomarker for diseases such as cardiovascular diseases, hematological diseases, neurological diseases, cancer, endocrinological diseases, and urological diseases.

4 Claims, 15 Drawing Sheets

Microarray expression data of LTBP2 in human heart

OTHER PUBLICATIONS

Lian et al. (2001, Blood 98:513-524).*

Fessler et al. (2002, J. Biol. Chem. 277:31291-31302).*

Li et al, 2004. J Dent Res. 83(3): 199-203.*

Buján et al., "Expression of elastic components in healthy and varicose veins," *World J. Surg.* 27, 901-05, August 3002.

Fang et al., "Mouse latent TGF-beta binding protein-2: molecular cloning and developmental expression," *Biochim. Biophys. Acta* 1354, 219-30, Nov. 20, 1997.

Shipley et al., "Developmental expression of latent transforming growth factor beta binding protein 2 and its requirement early in mouse development," *Mol. Cell. Biol.* 20, 4879-87, Jul. 2000.

Sinha et al., "Expression of latent TGF-beta binding proteins and association with TGF-beta 1 and fibrillin-1 following arterial injury," *Cardiovascular Res.* 53, 971-83, Mar. 2002.

International Search Report issued Feb. 7, 2008 for PCT/EP2007/008558 (WO 2008/046509).

* cited by examiner

FIG. 1A
SEQ ID NO:1

CCTCGCTCCCTCTCCGGTAATGAGGGGGCTGAGCTGTCCCTCCGAGGAGGGGGCC
TGGTGTGGATAAAAGAGACGAAAAAGCCGGGGGAGGTTTCCAAAAATAAAACCGT
CCGGGTCCCCTTCAGACGGCTGCAGGCACAGGGAGGAGGCGCGAAGGTGCAGCAG
CCGTGCGAGCCCAGCTGGAGTAGGAGCGCGGACTCGAGGCTCGGGGCGCGCAGCC
CTCGTTCCGCCGAGAGCCGGGCCCCAGTCGGCCGCTTCAGGGCCCCCTAGACTC
AGAGAAGCTGGCCGCCGGGCGGGGCCGGGAGAACAGCCCGCGGGCGTCCAGCGTG
CCGACCACAAAGCTCTTCGCGGTGCCCGCGCGCACCACTCTCCAGCCGCCCCGCG
CCATGAGGCCGCGGACCAAAGCCCGCAGCCCGGGGCGCGCCCTGCGGAACCCCTG
GAGAGGCTTCCTGCCGCTCACCCTGGCTCTCTTCGTGGGCGCGGGTCATGCCCAA
AGGGACCCCGTAGGGAGATACGAGCCGGCTGGTGGAGACGCGAATCGACTGCGGC
GCCCTGGGGGCAGCTACCCGGCAGCGGCTGCAGCCAAGGTGTACAGTCTGTTCCG
GGAGCAGGACGCGCCTGTCGCGGGCTTGCAGCCCGTGGAGCGGGCCCAGCCGGGC
TGGGGGAGCCCCAGGAGGCCCACCGAGGCGGAGGCCAGGAGGCCGTCCCGCGCGC
AGCAGTCGCGGCGTGTCCAGCCACCTGCGCAGACCCGGAGAAGCACTCCCCTGGG
CCAGCAGCAACCAGCACCCCGGACCCGGGCCGCGCCGGCTCTCCCACGCCTGGGG
ACCCCACAGCGGTCTGGGGCTGCGCCCCAACCCCGCCGCGAGGGCGGCTCACGG
GGAGGAACGTCTGCGGGGACAGTGCTGCCCAGGATGGACAACAGCAAACAGCAC
CAACCACTGTATCAAACCCGTTTGCGAGCCGCCGTGCCAGAACCGGGGCTCCTGC
AGCCGCCCGCAGCTCTGTGTCTGCCGCTCTGGTTTCCGTGGAGCCCGCTGCGAGG
AGGTCATTCCCGATGAGGAATTTGACCCCAGAACTCCAGGCTGGCACCTCGACG
CTGGGCCGAGCGTTCACCCAACCTGCGCAGGAGCAGTGCGGCTGGAGAGGGCACC
TTGGCCAGAGCACAGCCGCCAGCACCACAGTCGCCGCCCGCACCACAGTCGCCAC
CAGCTGGGACCCTGAGTGGCCTCAGCCAGACCCACCCTTCCCAGCAGCACGTGGG
GTTGTCCCGCACTGTCCGACTTCACCCGACTGCCACGGCCAGTAGCCAGCTCTCT
TCCAACGCCCTGCCCCGGGACCAGGCCTTGAGCAGAGAGATGGCACCCAACAGG
CGGTACCTCTGGAGCACCCCTCATCCCCTGGGGGCTGAACCTCACGGAGAAAAT
CAAGAAGATCAAGATCGTCTTCACTCCCACCATCTGCAAGCAGACCTGTGCCCGT
GGACACTGTGCCAACAGCTGTGAGAGGGGCGACACCACCACCCTGTACAGCCAGG
GCGGCCATGGGCACGATCCCAAGTCTGGCTTCCGCATCTATTTCTGCCAGATCCC
CTGCCTGAACGGAGGCCGCTGCATCGGCAGGGACGAATGCTGGTGCCCCGCCAAC
TCCACCGGGAAGTTCTGCCACCTGCCTATCCCGCAGCCGGACAGGGAGCCTCCAG
GGAGGGGGTCCCGCCCCAGGGCCTTGCTGGAAGCCCACTGAAGCAGTCCACTTT
CACACTGCCGCTCTCCAACCAGCTGGCCTCCGTGAACCCTCCCTGGTGAAGGTG
CACATTCACCACCCACCCGAGGCCTCAGTGCAGATCCACCAGGTGGCCCAGGTGC
GGGGCGGGGTGGAGGAGGCCCTAGTGGAGAACAGCGTGGAGACCAGACCCCGCC
CTGGCTGCCTGCCAGCCCTGGCCACAGCCTCTGGGACAGCAACAACATCCCTGCT

FIG. 1B
SEQ ID NO:1, cont.

```
CGGTCTGGAGAGCCCCCTCGGCCACTGCCCCCAGCAGCACCCAGGCCTCGAGGAC
TGCTGGGCCGGTGTTACCTGAACACTGTGAACGGACAGTGTGCCAACCCTCTGCT
GGAGCTGACTACCCAGGAGGACTGCTGTGGCAGTGTGGGAGCCTTCTGGGGGGTG
ACTTTGTGTGCCCCATGCCCACCCAGACCAGCCTCCCGGTGATTGAGAATGGCC
AGCTGGAGTGTCCTCAGGGGTACAAGAGACTGAACCTCACTCACTGCCAAGATAT
CAACGAGTGCTTGACCCTGGGCCTGTGCAAGGACGCGGAGTGTGTGAATACCAGG
GGCAGCTACCTGTGCACATGCAGACCTGGCCTCATGCTGGATCCATCGCGGAGCC
GCTGTGTGTCGGACAAGGCAATCTCCATGCTGCAGGGACTGTGCTACCGGTCGCT
GGGGCCCGGCACCTGCACCCTGCCTTTGGCCCAGCGGATCACCAAGCAGATATGC
TGCTGCAGCCGCGTGGGCAAAGCATGGGGCAGCGAGTGTGAGAAATGCCCTCTGC
CTGGCACAGAGGCCTTCAGAGAGATCTGCCCTGCCGGCCACGGCTACACCTACGC
GAGCTCCGACATCCGCCTGTCCATGAGGAAAGCCGAGGAGGAGGAACTGGCAAGG
CCCCCAAGGGAGCAAGGGCAGAGGAGCAGCGGGGCACTGCCCGGGCCAGCAGAGA
GGCAGCCCCTCCGGGTCGTCACGGACACCTGGCTTGAGGCCGGGACCATCCCTGA
CAAGGGTGACTCTCAGGCTGGCCAGGTCACGACCAGTGTCACTCATGCACCTGCC
TGGGTCACAGGGAATGCCACAACCCCACCAATGCCTGAACAGGGGATTGCAGAGA
TACAGGAAGAACAAGTGACCCCCTCCACCGATGTGCTGGTGACCCTGAGCACCCC
AGGCATTGACAGATGCGCTGCTGGAGCCACCAACGTCTGTGGCCCTGGAACCTGC
GTGAACCTCCCCGATGGATACAGATGTGTCTGCAGCCCTGGCTACCAGCTGCACC
CCAGCCAGGCCTACTGCACAGATGACAACGAGTGTCTGAGGGACCCCTGCAAGGG
AAAAGGGCGCTGCATCAACCGCGTGGGGTCCTACTCCTGCTTCTGCTACCCTGGC
TACACTCTGGCCACCTCAGGGGCGACACAGGAGTGTCAAGATATCAATGAGTGTG
AGCAGCCAGGGGTGTGCAGCGGGGGGCAGTGCACCAACACCGAGGGCTCGTACCA
CTGCGAGTGTGATCAGGGCTACATCATGGTCAGGAAAGGACACTGCCAAGATATC
AACGAATGCCGTCACCCCGGTACCTGCCCTGATGGGAGATGCGTCAATTCCCCTG
GCTCCTACACTTGTCTGGCCTGTGAGGAGGGCTACCGGGGCCAGAGTGGGAGCTG
TGTAGATGTGAATGAGTGTCTGACTCCCGGGGTCTGTGCCCATGGAAAGTGCACC
AACCTAGAAGGCTCCTTCAGATGCTCTTGTGAGCAGGGCTATGAGGTCACCTCAG
ATGAGAAGGGCTGCCAAGATGTGGATGAGTGTGCCAGCCGGGCCTCATGCCCCAC
AGGCCTCTGCCTCAACACGGAGGGCTCCTTCGCCTGCTCTGCCTGTGAGAACGGG
TACTGGGTGAATGAAGACGGCACTGCCTGTGAAGACCTAGATGAGTGTGCCTTCC
CGGGAGTCTGCCCCTCCGGAGTCTGCACCAACACGGCTGGCTCCTTCTCCTGCAA
GGACTGCGATGGGGGCTACCGGCCCAGCCCCTGGGTGACTCCTGTGAAGATGTG
GATGAATGTGAAGACCCCCAGAGCAGCTGCCTGGGAGGCGAGTGCAAGAACACTG
TGGGCTCCTACCAGTGCCTCTGTCCCAGGGCTTCCAGCTGGCCAATGGCACCGT
GTGTGAGGATGTGAATGAGTGCATGGGGGAGGAGCACTGCGCACCCCACGGCGAG
```

FIG. 1C
SEQ ID NO:1, cont.

TGCCTCAACAGCCACGGGTCTTTCTTCTGTCTGTGCGCGCCTGGCTTCGTCAGCG
CAGAGGGGGCACCAGCTGCCAGGATGTGGACGAGTGTGCCACCACAGACCCGTG
TGTGGGAGGGCACTGTGTCAACACCGAGGGCTCCTTCAACTGTCTATGTGAGACT
GGCTTCCAGCCCTCCCCAGAGAGTGGAGAGTGTGTGGATATTGACGAGTGTGAGG
ACTATGGAGACCCGGTGTGTGGCACCTGGAAGTGTGAAAACAGCCCTGGCTCCTA
CCGCTGTGTTCTGGGCTGCCAGCCTGGCTTCCACATGGCCCCGAACGGAGACTGC
ATTGACATAGACGAGTGCGCCAACGACACCATGTGTGGCAGCCACGGCTTCTGTG
ACAACACTGATGGCTCCTTCCGCTGCCTCTGTGACCAGGGCTTCGAGATCTCTCC
CTCAGGCTGGGACTGTGTGGATGTGAACGAGTGTGAGCTTATGCTGGCGGTATGT
GGGGCCGCGCTCTGTGAGAACGTGGAGGGCTCCTTCCTGTGCCTCTGTGCCAGTG
ACCTGGAGGAGTACGATGCCCAGGAGGGGCACTGCCGCCCACGGGGGGCTGGAGG
TCAGAGTATGTCTGAGGCCCCAACGGGGGACCATGCCCCGGCCCCACCCGCATG
GACTGCTACTCCGGGCAGAAGGGCCATGCGCCCTGCTCCAGTGTCCTGGGCCGGA
ACACCACACAGGCTGAATGCTGCTGCACCCAGGGCGCTAGCTGGGGAGATGCCTG
TGACCTCTGCCCGTCTGAGGACTCAGCTGAATTCAGCGAGATCTGCCCTAGTGGA
AAAGGCTACATTCCTGTGGAAGGAGCCTGGACGTTTGGACAGACCATGTACACAG
ATGCGGATGAGTGTGTGATATTCGGGCCTGGTCTCTGCCCGAACGGCCGGTGCCT
CAACACCGTGCCTGGTTATGTCTGCCTGTGCAATCCCGGCTTCCACTACGATGCT
TCCCACAAGAAGTGTGAGGATCACGATGAGTGCCAGGACCTGGCCTGTGAGAATG
GCGAGTGCGTCAACACGGAGGGCTCCTTCCACTGCTTCTGCAGCCCCCCGCTCAC
CCTGGACCTCAGCCAGCAGCGCTGCATGAACAGCACCAGCAGCACGGAGGACCTC
CCTGACCACGACATCCACATGGACATCTGCTGGAAAAAAGTCACCAATGATGTGT
GCAGCGAACCCCTGCGTGGGCACCGCACCACCTACACGGAATGCTGCTGCCAGGA
CGGCGAGGCCTGGAGCCAGCAGTGTGCTCTGTGTCCCCGAGGAGCTCTGAGGTC
TATGCTCAGCTGTGCAACGTGGCTCGCATTGAGGCAGAGCGGGAGGCCGGGTCC
ACTTCCGGCCAGGCTATGAGTATGGCCCCGGGCCCGATGACCTGCACTACAGCAT
CTATGGCCCAGATGGGGCCCCCTTCTACAACTACCTGGGCCCCGAGGACACCGTC
CCTGAGCCTGCCTTCCCCAACACAGCCGGTCACTCAGCGGACCGCACACCCATCC
TTGAGTCTCCTTTGCAGCCCTCAGAACTCCAGCCCCACTACGTGGCCAGCCATCC
AGAGCCCCCAGCCGGCTTCGAAGGGCTTCAGGCGGAGGAGTGCGGCATCCTGAAC
GGCTGTGAGAATGGCCGCTGTGTGCGCGTGCGGGAGGGCTACACCTGTGACTGTT
TTGAGGGCTTCCAGCTGGATGCGGCCCACATGGCCTGCGTAGATGTGAATGAGTG
TGATGACTTGAACGGGCCTGCTGTGCTCTGTCCATGGTTACTGCGAGAACACA
GAGGGCTCCTACCGCTGCCACTGCTCCCCGGGATATGTGGCTGAGGCAGGGCCCC
CCCACTGCACTGCCAAGGAGTAGCAGTCAGGGTCAGTGTGGCAACTACCTGGAA
ATGGCCTCCAGTCACAGGCAGGGCCTTGAGGATGATTTCCTAGCTGGGAAGACA

FIG. 1D
SEQ ID NO:1, cont.

```
CCGTGACATCAGGCCAGAGGTTTCCAATCAGCCTTGCCTGCTTTCATCTCTCCCA
GCTTAGCCTCTGGCTGTAAGCTTCGGTCATTGCCTCCATGCCCTTGCTTGGCTCA
AGCACCACCAATCGCTTTAATGCTTCAGCCACCGCATGAGGCCCTGTCCACCACC
TTTCCTGGCCTTGCTATGGGATGCTTACCAAAGGATGGCCCTCATCCACCCTCCC
AAGCTGTGCGAGCATGCAAGGCCCCATGGCCTCACACTGCAGACACCCCTTTCCA
GCCACAATCCACCATCATCCTGACGATCCCACAACTGGGACAGAGGCTACATCTG
CCCTAGGGAGGTCCTTCAGAATCTGTGGAGCAAGAAAGGATTTGGGGAAGCTTGG
GGACTGACTCCAGAGCCCCCTCCTAAGAACCATCACCACCACTCAGCCAATCTGT
TCTGGGCCCTGATTTTGCCACACCTCCATCCTGTAGCCCATTCTCTGACCCCAAG
GAGTGGCAGAAGATCCCTTCACTCAGAGAAGCAAGGCTGATATTAGCTTGTTGAA
TGTAAGAGACACAAATGAAGAAGAACAAAGAGCCTGAGAAAGCAGCAAGAGGACA
TGATGAAAATACGTGGAGTTGATGAGAAAGGGGAGCCAAGGCTTTATACGTCTA
AAGAAAATATTCAGTAGCTGAATCCGCCCAGTGATAGCCTGTGGGCACCAGCAGC
AAGGGCTGCCATGGATACAGCACCCATCTACAAAGACCTCTATTACATAAACAC
TGCTTCTTACAGGAAACAAACCTCTTCTGGGATCTCCTTTTGTGAAAACCAGTTT
GATGTGCTAAAAGTAAAAGTCTATTTTCCAGTGTGGTCTTGTTCAGAAGCAGCC
AGATTTCCAATGTTGTTTTTCCCCTCCACTCAGAAACCCCTGCCCTTTCCCTTCA
GAAAACGATGGCAGGCATTCCTCTGAGTTTACAAGCAGAGACTCACTCCAACCCA
AACTAGCTGGGAGTTCAGAACCATGGTGGAATAAAGAAATGTGCATCTGGTCCAA
AAAAAAAAAAAAAAAAAAAAAAAAAAAAAAA
```

FIG. 2A
SEQ ID NO:2

```
AGAGGTCCCTAGACGGGAAGGGGCACGCCGCCAGGCGGGACTGTGGAGCTAACGA
TGGAGAGCACCTCCCTGCGAGGTCTCCGGTGCCCACAGCTCTGCAGCCACTCTGG
CGCCATGAGGGCGCCGACCACCGTCCGCTGCTCCGGACGCATCCAAAGGGCGCGT
TGGAGGGGCTTCCTGCCACTTGTCCTGGCTCTCTTGATGGGGACAAGTCATGCCC
AAAGGGATTCCGTGGGGAGATACGAACCAGCTAGCCGGGATGCCAATCGGTTGTG
GCGCCCCGTGGGCAACCACCCCGCAGCGGCTGCAGCCAAGGTGTACAGTCTGTTC
CGAGAGCCCGACGCGCCGGTCCCCGGCTTGTCGCCCTCTGAGTGGAATCAGCCGG
GCCAGGGGATCCCTGGGAGGCTCGCAGAGGCCGAGGCCAGGAGACCGTCCCGAGC
CCAGCAGCTGCGTCGAGTCCAGTCACCTGTCCAGACTCGGAGAAGCAATCCCCGA
GGCCAGCAGCCACCAGCAGCCCGGACCGCACATTCCGTCGTGCGCCTGGCGACCC
CTCAGCGACCCGCGGCTGCACGCCGAGGGCGGCTCACCGGGAGAAATGTCTGCGG
GGGACAGTGCTGCCCTGGATGGACGACATCGAACAGCACCAACCACTGTATCAAA
CCTGTGTGTCAGCCTCCCTGTCAGAACCGGGGCTCCTGCAGCCGGCCCCAGCTCT
GCATCTGCCGTTCTGGCTTCCGTGGGGCACGCTGCGAGGAGGTCATCCCTGAGGA
GGAGTTTGACCCTCAGAATGCCAGGCCTGTGCCCAGACGCTCAGTGGAGGGAGCA
CCTGGCCCTCACAGGAGCAGCGAGGCCAGAGGAAGTCTAGTGACCAGAATACAGC
CGCTGCTACCACCACTACCACCACCTCCATCTAGGACCCTCAGCCAGACCCGTCC
CCTGCAGCAGCATGCAGGACTGTCCAGAACAGTTCGTCGTTATCCGGCCACTGGT
ACCAATGGCCAACTGATGTCCAACGCTCTGCCTTCAGGACCAGGACCTGAGCTGA
GAGACAGCAGCCAACAGGCAGCACACATGAACCATCTCTCACACCCCTGGGGGCT
GAACCTCACCGAGAAAATCAAGAAGATTAAGGTCGTCTTCACTCCACCATCTGC
AAGCAGACCTGTGCCCGGGGCCGCTGTGCCAACACGTGTGAGAAGGGTGACACCA
CCACCCTGTACAGTCAGGGCGGCCATGGGCATGACCCCAAGTCTGGCTTCCGTAT
CTATTTCTGCCAAATCCCCTGCCTGAATGGAGGCCGCTGCATTGGCCGGGACGAG
TGCTGGTGTCCAGCCAACTCTACAGGGAAGTTCTGCCATCTGCCTGTCCCACAGC
CAGACAGGGAGCCTCCAGGACGAGGCTCCCAGCACAGAGCCCTGCTGGAAGGGCC
ATTGAAGCAATCCACCTTCACGCTGCCTCTCTCCAACCAGCTGGCCTCTGTGAAC
CCCTCGCTGGTGAAGGTACAAATGCAGCACCCGCCTGAGGCCTCCGTGCAGATCC
ACCAGGTGGCCCGGGTCCGGGGTGAGGTGGACCCTGTGCCAGAGGACAACAGTGT
GGAGACCAGAGCCTCTCATCGCCCCATGGCAGCTCAGGCCACAGCCACTGGGCC
AGCAACAGCATACCCGCTCGGGCTGGAGAGGCCCCTCGGCCACCACCAGTGCCGT
CCAGGCATTATGGACTTCTGGGCCAGTGTTACCTGAGCACGGTGAATGGACAGTG
TGCTAACCCCCTAGGGGAGCTGACTTCTCAGGAAGACTGCTGTGGCAGTGTGGGG
ACTTCTTGGGGGTGACTTCCTGTGCCCCATGCCCACCCAGACCAGCTTTCCCCG
TGATTGAAAACGGCCAGCTGGAGTGTCCCAAGGGTATAAGAGACTAAACCTCAG
CCATTGCCAAGACATCAATGAGTGCCTGACCCTGGGCCTGTGCAAGGATTCAGAG
```

FIG. 2B
SEQ ID NO:2, cont.

```
TGTGTGAACACCAGGGGCAGCTACCTGTGCACCTGCAGGCCCGGCCTCATGCTGG
ATCCATCAAGGAGCCGCTGTGTATCGGACAAGGCTGTCTCCATGAAACAGGGACT
CTGTTACCGGTCAATGGTGTCTGGCACCTGCACCCTGCCTTTGGTACAACGGATC
ACCAAGCAGATATGCTGTTGCAGCCGTGTGGGCAAAGCCTGGGGCAGCAAATGTG
AACACTGCCCCCTGCCTGGCACAGAAGCCTTCAGGGAGATCTGCCCTGCTGGCCA
TGGCTACGCCTACTCAAGCTCAGACATCCGCCTGTCTATGAGGAAAGCTGAGGAA
GAGGAACTGGCTAGCCCCGTAAGGGAACAGAGACAGCAGAGCAGTGGACCCCCAC
CTGGGGCAGCAGAAAGGCAGCCACTCCGGGCAGCCACTGCCACCTGGATTGAGGC
TGAGACCCTCCCTGACAAGGTGACTCTCGGGCTATTCAGATTACAACCAGTGCT
CCCCACCTACCTGCCCGGGTACCAGGGGATGCCACTGGAAGACCAACGCCATCAT
TGCCTGGACAGGGCATTCCAGAGGGTCCAGCAGAAGAGCAGGTGATCCCTTCCAG
TGATGTCCTGGTGACGCACGGTCCCCAGGCTTTGATCCATGTTTCGCTGGAGCC
TCCAACATCTGTGGCCCTGGGACCTGTGTGAAGCTCCCAAATGGATACAGATGTG
TCTGCAGCCCTGGTTACCAGCTACACCCCAGCCAGGACTACTGTACTGATGACAA
CGAGTGTCTGAGGAACCCCTGTGAAGGAAGAGGGCGCTGTGTCAACAGTGTGGGC
TCCTACTCCTGCCTCTGCTACCCAGGCTACACACTAGCCACCCTAGGAGACACAC
AGGAGTGCCAAGATGTGGATGAGTGTGAGCAGCCGGGGGTGTGCAGCGGTGGACG
ATGCAGCAACACTGAGGGCTCGTACCACTGCGAGTGTGATCAGGGCTACGTCATG
GTCAGAAGAGGACACTGCCAAGATATCAACGAATGCCGTCACCCTGGTACCTGCC
CTGATGGGAGATGCGTCAACTCCCCTGGCTCCTACACTTGTCTGGCCTGTGAGGA
GGGCTACATAGGGCAGAGCGGGAACTGTGTAGATATGAATGAGTGTCTGACCCCC
GGGATATGTGCCCATGGAAGGTGCATCAACATGGAAGGCTCCTTTAGATGCTCTT
GTGAGCCAGGCTATGAGCTCACCCCAGACAAGAAGGGCTGCCGAGATGTGGACGA
GTGTGCCAGCCGAGCCTCATGCCCCACCGGCCTCTGCCTCAACACGGAGGGCTCC
TTCACCTGCTCAGCCTGTCAGAGTGGGTACTGGGTGAACGAAGATGGCACTGCCT
GTGAAGACCTGGATGAATGTGCCTTCCCCGGAGTCTGCCCCACAGGCGTCTGCAC
CAACACTGTGGGCTCCTTCTCCTGCAAGGACTGCGACAGGGGCTTCCGGCCCAGC
CCCCTGGGCAACAGCTGTGAAGATGTGGATGAGTGTGAAGGTCCCCAGAACAGCT
GCCTGGGAGGCGAGTGCAAGAACACAGATGGTTCCTACCAGTGCCTCTGTCCCCA
GGGCTTCCAGCTGGCCAATGGCACCGTGTGTGAGGATGTGGACGAATGTGTTGGG
GAAGAACACTGCGCTCCTCATGGCGAATGCCTCAACAGCCCGGGTCCTTCTTCT
GTCTCTGTGCACCCGGCTTTGCTAGTGCTGAGGGGGGCACCAGATGCCAGGATGT
TGATGAATGTGCAACCACAGAGCCGTGTCTGGGAGGACACTGTGTCAACACCGAG
GGCTCCTTCAACTGTCTGTGTGAGACTGGCTTCCAGCCCGCCCCAGACAGTGGAG
```

FIG. 2C
SEQ ID NO:2, cont.

```
AGTGTGTGGACATAGATGAATGTGCAAATGATACTGTGTGTGGGAACCATGGCTT
CTGTGACAATACGGATGGCTCCTTCCGCTGCCTGTGTGACCAGGGCTTCGAGACC
TCACCCTCAGGCTGGGAGTGTGTTGATGTGAACGAGTGTGAGCTCATGCTGGCAG
TGTGTGGGATGCACTCTGCGAGAACGTGGAAGGCTCCTTCCTGTGCCTTTGTGC
CAGTGACCTTGAGGAGTATGATGCAGAAGAAGGACACTGCCGTCCTCGGGTGGCT
GGAGCTCAGAGAATCCCAGAGGTCCCAACAGAGGAGCAGGCTGCAGGCCTTACCG
GCATGGAGTGCTATGCTGAACACAATGGTGGTCCTCCATGCTCTCAAATCTTGGG
CCAGAACTCCACACAGGCTGAGTGCTGCTCGACCCAGGGTGCCAGATGGGGGAA
ACCTGTGATCCCTGCCCATCTGAGGACTCAGTTGAATTCAGTGAGCTGTGCCCCA
GTGGTCAAGGTTACATCCCAGTGGAAGGGGCCTGGACATTTGGACAAGCCATGTA
TACAGATGCCGACGAGTGCATACTGTTTGGGCCTGCTCTCTGCCAGAATGGCCGA
TGCCTCAACACAGTGCCTGGCTACATTTGCCTGTGCAACCCTGGCTACCACTATG
ATGCCGTCAGCAGGAAGTGCCAGGATCACAACGAATGCCAGGACTTGGCCTGTGA
GAACGGCGAGTGTGTGAACACAGAAGGCTCCTTCCACTGCTTCTGCAGTCCCCCC
CTCATCCTAGACCTCAGCGGACAGCGCTGTGTGAACAGTACCAGCAGCTCAGAGG
ACTTCCCTGACCATGACATCCACATGGACATCTGCTGGAAAAAAGTCACCAATGA
CGTGTGCAGCCAGCCCTTGCGTGGGCACCATACTACCTATACAGAGTGCTGCTGC
CAAGACGGGGAGGCCTGGAGCCAGCAGTGTGCTCTGTGCCCCCCCAGGAGCTCTG
AGGTCTATGCTCAGCTGTGCAATGTGGCTCGGATTGAGGCAGAGAGGGAAGCAGG
GATCCACTTCCGGCCAGGATATGAGTATGGCCCTGGCCCAGATGATCTACCTGAA
ACCCTCTACGGCCCAGATGGAGCCCCTTTCTATAACTACCTGGGCCCTGAGGACA
CTGTTCCTGAGCCTCCCTTCTCCAACACAGCCAGTCATTTGGGAGACAACACACC
CATCCTTGAGCCTCCCCTGCAGCCCTCTGAACTTCAGCCCCAGCCATTCAGAAC
CCCCTGGCTTCCTTCGAAGGCCTTCAGGCTGAGGAATGTGGCATCCTGAATGGCT
GTGAGAATGGCCGCTGTGTGCGTGTGCGCGAGGGCTACACTTGTGACTGCTTTGA
AGGCTTCCAGCTGGATACAGCCCTCATGGCCTGTGTGGATGTGAATGAGTGTGAA
GACCTGAACGGCGCTGCGCGACTCTGTGCGCATGGTCACTGCGAGAACACAGAGG
GTTCCTATCGCTGCCACTGTTCCCCTGGTTACGTGGCAGAGCCCGGGCCCCCACA
CTGTGCAGCCAAGGAGTAGGAGTGAGAGATCATGGTGGGCAGCTATGTGGAAATG
GCTATCAGCCATAGGCTGGGGACTTAAGGTTGCTTCCCTAGCTGGGAAGACGTGA
CTGGGAAGACCCCGTGATGCCATCAGGCCAGGGCTCTGGAGCCCAGTTCCGCCAG
CCTCGCCTCCTTTTTATCTCTTCCGGCTTAACTCTGGGTGTGAATTCCGTCACTG
CCTCTATGCCACTGCTTGGCTCAGACACCACAAATATTTTAATGCTTTAGCCACT
GGCCGTGAGACACAGCCCACAGTCTGTCCTCGGGCCACACTTTAGAGCGCCCAT
CAGAAGAGTCCTCGTGCACTCCTCTTAGGCTGTGCAGACACTGCAGGCACCCCT
```

FIG. 2D
SEQ ID NO:2, cont.

```
TCCATCTGTGATCTACACATCATCTCGATGGTTCTGTAACGGGGACAGTGGCTAC
ATCCACCTGGGGATGGCCCTTCACAGTGAATGGAGCAGGAGAGGGTCTGGGGAGT
AGCTCCAATGCCACCTCTCAGAACCACCACCAGCACTGGGTGGCGTGAGTTCTTT
TTGCTACTCCTCCATCCCATAGACAGTTCTGCGGCCCCGAGAAGGGACCAGTTTC
CCTCACCTCAGAGGATGAAGACTAATACTAACTTGCTGAGTGTAAGAAACGAAAG
AAGAGGAATAACGAGTCTGAGAAAGTGTGGCAAGAGAGTGATACGGAAAACATGG
GAGTCCATATGAAAGGAGGAGCCAAGAGTTAGACAAAACACGAAGTCGCTTTGGG
CAAATCAGTCCAAGCCTCCTTAGAGCTTCTGTGTGCCTGCAGGGAGGCTCGCCAC
AAGCTCTGGCGCCCATCTGCAAACACCTTTATTAGGCTCATCTGTTCCCCACAGG
AAAACCTAAATAGATGGCCTTAACAATATAAAGGCAGAGCAAGCCAGATTTTTCA
AAGTTGTTTCTCTCCTCCACTTCAGAAGCACTTGCCCTTGCTTCCTCTTAACACA
TGCACTTCCACACCAGCTAGCTGGGGTTCAGGAGCGTGGGGAATAAAATGTTC
ATCTGCC
```

FIG. 3
SEQ ID NO:3

MRPRTKARSPGRALRNPWRGFLPLTLALFVGAGHAQRDPVGRYEPAGGDANRLRR
PGGSYPAAAAAKVYSLFREQDAPVAGLQPVERAQPGWGSPRRPTEAEARRPSRAQ
QSRRVQPPAQTRRSTPLGQQQPAPRTRAAPALPRLGTPQRSGAAPPTPPRGRLTG
RNVCGGQCCPGWTTANSTNHCIKPVCEPPCQNRGSCSRPQLCVCRSGFRGARCEE
VIPDEEFDPQNSRLAPRRWAERSPNLRRSSAAGEGTLARAQPPAPQSPPAPQSPP
AGTLSGLSQTHPSQQHVGLSRTVRLHPTATASSQLSSNALPPGPGLEQRDGTQQA
VPLEHPSSPWGLNLTEKIKKIKIVFTPTICKQTCARGHCANSCERGDTTTLYSQG
GHGHDPKSGFRIYFCQIPCLNGGRCIGRDECWCPANSTGKFCHLPIPQPDREPPG
RGSRPRALLEAPLKQSTFTLPLSNQLASVNPSLVKVHIHHPPEASVQIHQVAQVR
GGVEEALVENSVETRPPPWLPASPGHSLWDSNNIPARSGEPPRPLPPAAPRPRGL
LGRCYLNTVNGQCANPLLELTTQEDCCGSVGAFWGVTLCAPCPPRPASPVIENGQ
LECPQGYKRLNLTHCQDINECLTGLCKDAECVNTRGSYLCTCRPGLMLDPSRSR
CVSDKAISMLQGLCYRSLGPGTCTLPLAQRITKQICCCSRVGKAWGSECEKCPLP
GTEAFREICPAGHGYTYASSDIRLSMRKAEEEELARPPREQGQRSSGALPGPAER
QPLRVVTDTWLEAGTIPDKGDSQAGQVTTSVTHAPAWVTGNATTPPMPEQGIAEI
QEEQVTPSTDVLVTLSTPGIDRCAAGATNVCGPGTCVNLPDGYRCVCSPGYQLHP
SQAYCTDDNECLRDPCKGKGRCINRVGSYSCFCYPGYTLATSGATQECQDINECE
QPGVCSGGQCTNTEGSYHCECDQGYIMVRKGHCQDINECRHPGTCPDGRCVNSPG
SYTCLACEEGYRGQSGSCVDVNECLTPGVCAHGKCTNLEGSFRCSCEQGYEVTSD
EKGCQDVDECASRASCPTGLCLNTEGSFACSACENGYWVNEDGTACEDLDECAFP
GVCPSGVCTNTAGSFSCKDCDGGYRPSPLGDSCEDVDECEDPQSSCLGGECKNTV
GSYQCLCPQGFQLANGTVCEDVNECMGEEHCAPHGECLNSHGSFFCLCAPGFVSA
EGGTSCQDVDECATTDPCVGGHCVNTEGSFNCLCETGFQPSPESGECVDIDECED
YGDPVCGTWKCENSPGSYRCVLGCQPGFHMAPNGDCIDIDECANDTMCGSHGFCD
NTDGSFRCLCDQGFEISPSGWDCVDVNECELMLAVCGAALCENVEGSFLCLCASD
LEEYDAQEGHCRPRGAGGQSMSEAPTGDHAPAPTRMDCYSGQKGHAPCSSVLGRN
TTQAECCCTQGASWGDACDLCPSEDSAEFSEICPSGKGYIPVEGAWTFGQTMYTD
ADECVIFGPGLCPNGRCLNTVPGYVCLCNPGFHYDASHKKCEDHDECQDLACENG
ECVNTEGSFHCFCSPPLTLDLSQQRCMNSTSSTEDLPDHDIHMDICWKKVTNDVC
SEPLRGHRTTYTECCCQDGEAWSQQCALCPPRSSEVYAQLCNVARIEAEREAGVH
FRPGYEYGPGPDDLHYSIYGPDGAPFYNYLGPEDTVPEPAFPNTAGHSADRTPIL
ESPLQPSELQPHYVASHPEPPAGFEGLQAEECGILNGCENGRCVRVREGYTCDCF
EGFQLDAAHMACVDVNECDDLNGPAVLCVHGYCENTEGSYRCHCSPGYVAEAGPP
HCTAKE

FIG. 4
SEQ ID NO:4

MRAPTTVRCSGRIQRARWRGFLPLVLALLMGTSHAQRDSVGRYEPASRDANRLWR
PVGNHPAAAAAKVYSLFREPDAPVPGLSPSEWNQPGQGIPGRLAEAEARRPSRAQ
QLRRVQSPVQTRRSNPRGQQPPAARTAHSVVRLATPQRPAAARRGRLTGRNVCGG
QCCPGWTTSNSTNHCIKPVCQPPCNRGSCSRPQLCICRSGFRGARCEEVIPEEE
FDPQNARPVPRRSVEGAPGPHRSSEARGSLVTRIQPLLPPLPPPPSRTLSQTRPL
QQHAGLSRTVRRYPATGTNGQLMSNALPSGPGPELRDSSQQAAHMNHLSHPWGLN
LTEKIKKIKVVFTPTICKQTCARGRCANTCEKGDTTTLYSQGGHGHDPKSGFRIY
FCQIPCLNGGRCIGRDECWCPANSTGKFCHLPVPQPDREPPGRGSQHRALLEGPL
KQSTFTLPLSNQLASVNPSLVKVQMQHPPEASVQIHQVARVRGEVDPVPEDNSVE
TRASHRPHGSSGHSHWASNSIPARAGEAPRPPPVPSRHYGLLGQCYLSTVNGQCA
NPLGELTSQEDCCGSVGTSWGVTSCAPCPPRPAFPVIENGQLECPQGYKRLNLSH
CQDINECLTLGLCKDSECVNTRGSYLCTCRPGLMLDPSRSRCVSDKAVSMKQGLC
YRSMVSGTCTLPLVQRITKQICCCSRVGKAWGSKCEHCPLPGTEAFREICPAGHG
YAYSSSDIRLSMRKAEEEELASPVREQRQQSSGPPPGAAERQPLRAATATWIEAE
TLPDKGDSRAIQITTSAPHLPARVPGDATGRPTPSLPGQGIPEGPAEEQVIPSSD
VLVTHGPPGFDPCFAGASNICGPGTCVKLPNGYRCVCSPGYQLHPSQDYCTDDNE
CLRNPCEGRGRCVNSVGSYSCLCYPGYTLATLGDTQECQDVDECEQPGVCSGGRC
SNTEGSYHCECDQGYVMVRRGHCQDINECRHPGTCPDGRCVNSPGSYTCLACEEG
YIGQSGNCVDMNECLTPGICAHGRCINMEGSFRCSCEPGYELTPDKKGCRDVDEC
ASRASCPTGLCLNTEGSFTCSACQSGYWVNEDGTACEDLDECAFPGVCPTGVCTN
TVGSFSCKDCDRGFRPSPLGNSCEDVDECEGPQNSCLGGECKNTDGSYQCLCPQG
FQLANGTVCEDVDECVGEEHCAPHGECLNSPGSFFCLCAPGFASAEGGTRCQDVD
ECATTEPCLGGHCVNTEGSFNCLCETGFQPAPDSGECVDIDECANDTVCGNHGFC
DNTDGSFRCLCDQGFETSPSGWECVDVNECELMLAVCGDALCENVEGSFLCLCAS
DLEEYDAEEGHCRPRVAGAQRIPEVPTEEQAAGLTGMECYAEHNGGPPCSQILGQ
NSTQAECCSTQGARWGETCDPCPSEDSVEFSELCPSGQGYIPVEGAWTFGQAMYT
DADECILFGPALCQNGRCLNTVPGYICLCNPGYHYDAVSRKCQDHNECQDLACEN
GECVNTEGSFHCFCSPPLILDLSGQRCVNSTSSSEDFPDHDIHMDICWKKVTNDV
CSQPLRGHHTTYTECCCQDGEAWSQQCALCPPRSSEVYAQLCNVARIEAEREAGI
HFRPGYEYGPGPDDLPETLYGPDGAPFYNYLGPEDTVPEPPFSNTASHLGDNTPI
LEPPLQPSELQPPAIQNPLASFEGLQAEECGILNGCENGRCVRVREGYTCDCFEG
FQLDTALMACVDVNECEDLNGAARLCAHGHCENTEGSYRCHCSPGYVAEPGPPHC
AAKE

FIG. 5
SEQ ID NO:5

5' CGAGATCTGCCCTAGTGGAAA 3'

FIG. 6
SEQ ID NO:6

5' GGCCCGAATATCACACACTCA 3'

FIG. 7
SEQ ID NO:7

5' AGCCTGGACGTTTGGACAGACCA 3'

FIG. 8
SEQ ID NO:8

5' CACTTGTGACTGCTTTGAAGG 3'

FIG. 9
SEQ ID NO:9

5' CCCGTTCAGGTCTTCACACT 3'

Fig. 10
SEQ ID NO: 10
5' CTCATGGCCTGTGTGGATGTGAATG 3'
Fig. 11
Real-time expression data of LTBP2 in rat heart (DOCA model)
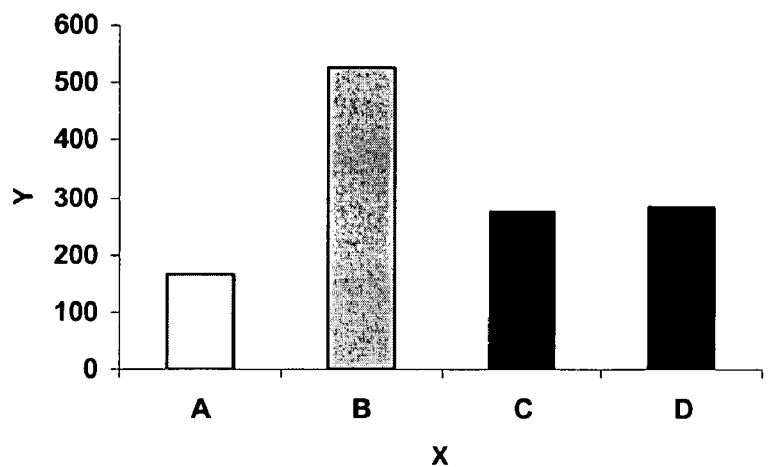
Fig. 12
Real-time expression data of LTBP2 in rat heart (occlusion model)
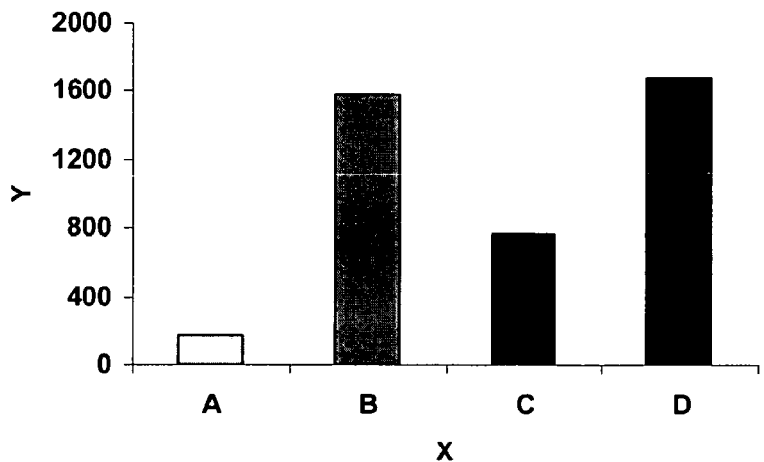

Real-time expression data of LTBP2 in rat heart (monocrotalin model)

Microarray expression data of LTBP2 in rat heart (DOCA model)

Microarray expression data of LTBP2 in rat heart (occlusion model)

Microarray expression data of LTBP2 in rat heart (monocrotalin model)

Microarray expression data of LTBP2 in human heart

LTBP2 AS A BIOMARKER AND DIAGNOSTIC TARGET

This application is a National Stage application of copending PCT application PCT/EP2007/008558 filed on Oct. 2, 2007, which was published in English under PCT Article 21(2) on Apr. 24, 2008, and which claims the benefit of European patent application Serial No. 06021595.1 filed Oct. 16, 2006. These applications are incorporated herein by reference in their entireties.

This application incorporates by reference the contents of a 44.7 KB text file created on Apr. 1, 2009 and named "BHC061149_sequence_listing.txt," which is the sequence listing for this application.

TECHNICAL FIELD OF THE INVENTION

The present invention is in the field of molecular biology, more particularly, the present invention relates to nucleic acid sequences and amino acid sequences of a human and rat LTBP2 and its regulation for the treatment, diagnostic and use as a biomarker of cardiovascular diseases, hematological diseases, neurological diseases, cancer, endocrinological diseases and urological diseases in mammals.

BACKGROUND OF THE INVENTION

TaqMan-Technology/Expression Profiling

TaqMan is a recently developed technique, in which the release of a fluorescent reporter dye from a hybridisation probe in real-time during a polymerase chain reaction (PCR) is proportional to the accumulation of the PCR product. Quantification is based on the early, linear part of the reaction, and by determining the threshold cycle (CT), at which fluorescence above background is first detected.

Gene expression technologies may be useful in several areas of drug discovery and development, such as target identification, lead optimization, and identification of mechanisms of action. The TaqMan technology can be used to compare differences between expression profiles of normal tissue and diseased tissue. Expression profiling has been used in identifying genes, which are up- or downregulated in a variety of diseases. An interesting application of expression profiling is temporal monitoring of changes in gene expression during disease progression and drug treatment or in patients versus healthy individuals. The premise in this approach is that changes in pattern of gene expression in response to physiological or environmental stimuli (e.g., drugs) may serve as indirect clues about disease-causing genes or drug targets. Moreover, the effects of drugs with established efficacy on global gene expression patterns may provide a guidepost, or a genetic signature, against which a new drug candidate can be compared.

LTBP2

The nucleotide sequence of LTBP2 is accessible in the databases by the accession number Z37976 (human) and Y12760 (rat). The sequences are given in SEQ ID NO:1 (human) and SEQ ID NO:2 (rat). The amino acid sequence of LTBP2 depicted in SEQ ID NO:3 (human) and SEQ ID NO:4 (rat).

The transforming growth factor beta (TGFβ) cytokines are a multifunctional family that exert a wide variety of effects on both normal and transformed mammalian cells. The secretion and activation of TGFβs is regulated by their association with latency associated proteins and latent TGFβ binding proteins (LTBPs). Transforming growth factor β (TGFβ) exists as three mammalian isoforms (TGFβ1, TGFβ2 and TGFβ3). Each of these is usually secreted in large latent complexes (LLCs) which have no biological activity and comprise three components: a disulphide bonded homodimer of mature TGFβ associated non-covalently with latency-associated proteins (LAPs; homodimers of the N-terminal fragment of precursor TGFβ) and a covalently attached molecule of latent TGFβ binding protein (LTBP) Four LTBP genes have been identified: LTBP1 to LTBP4. LAPs are sufficient to render the mature homodimer inactive, and removal of both the LAPs and LTBP or modulation of their interaction is essential for any of the TGFβ isoforms to function. The TGFβ cytokines modulate the growth and functions of a wide variety of mammalian cell types. It has become evident in recent years that LTBPs may be involved in the assembly, secretion and targeting of TGFβ to sites at which it is stored and/or activated. Thus these proteins may play critical roles in controlling and directing the activity of TGFβs. LTBPs may also exert effects independently of those associated with TGFβ, for example as structural matrix proteins [Oklu et al., (2000)]

Relatively little is known about the functional role of LTBP2. Unlike the other LTBPs, LTBP2 is unable to associate with the small latent TGFβ [Saharinen et al. (2000)] Human LTBP2 is expressed mostly in the lung and to a lesser extent in the liver, skeletal muscle placenta and heart [Vehvilainen et al (2003)]. Latent TGFβ binding protein LTBP2 decreases fibroblast adhesion to fibronectin [Hyytiainen et al. (2003)] Elucidation of the functional role of LTBP2 is further limited by the fact that deletion of LTBP2 in mice leads to embryonic lethality [Shipley et al. (2000)].

Regarding a functional role of LTBP2 in the cardiovascular system, it was demonstrated that LTBP2 synthesis increased in response to arterial injury in a porcine model of coronary angioplasty [Sinha et al. (2000)] Thus, together with the well known role of TGFβ in the developing of heart failure [Watkins et al. (2006)] our finding that TGFβ-function modifying LTBP2 is regulated on RNA level in LVAD hearts as well as in various animal models of heart failure makes LTBP2 an attractive candidate biomarker for CHF.

LTBP2 is published (but not limited to) in patents WO2004075835 and WO02068579.

SUMMARY OF THE INVENTION

The invention relates to the use of LTBP2 polypeptides and polynucleotides as a biomarker in cardiovascular diseases, hematological diseases, neurological diseases, cancer, endocrinological diseases and urological diseases. The invention also relates to novel disease associations of LTBP2 polypeptides and polynucleotides. The invention also relates to the use of LTBP2 as a biomarker for cardiovascular diseases, hematological diseases, neurological diseases, cancer, endocrinological diseases and urological diseases. The invention also relates to novel methods of screening for therapeutic agents for the treatment of cardiovascular diseases, hematological diseases, neurological diseases, cancer, endocrinological diseases and urological diseases in a mammal. The invention also relates to pharmaceutical compositions for the treatment of cardiovascular diseases, hematological diseases, neurological diseases, cancer, endocrinological diseases and urological diseases in a mammal comprising a LTBP2 polypeptide, a LTBP2 polynucleotide, or regulators of LTBP2 or modulators of LTBP2 activity. The invention further comprises methods of diagnosing cardiovascular diseases, hematological diseases, neurological diseases, cancer, endocrinological diseases and urological diseases in a mammal.

BRIEF DESCRIPTION OF THE DRAWINGS

FIGS. 1A-1D show the nucleotide sequence of a human LTBP2 polynucleotide (SEQ ID NO:1). FIGS. 2A-2D show the nucleotide sequence of a rat LTBP2 polynucleotide (SEQ ID NO:2).

FIG. 3 shows the amino acid sequence of a LTBP2 polypeptide human (SEQ ID NO:3).

FIG. 4 shows the amino acid sequence of a LTBP2 polypeptide rat (SEQ ID NO:4).

FIG. 5 shows the nucleotide sequence of a primer useful for the invention (SEQ ID NO:5).

FIG. 6 shows the nucleotide sequence of a primer useful for the invention (SEQ ID NO:6).

FIG. 7 shows a nucleotide sequence useful as a probe to detect proteins of the invention (SEQ ID NO:7).

FIG. 8 shows the nucleotide sequence of a primer useful for the invention (SEQ ID NO:8).

FIG. 9 shows the nucleotide sequence of a primer useful for the invention (SEQ ID NO:9).

FIG. 10 shows a nucleotide sequence useful as a probe to detect proteins of the invention (SEQ ID NO: 10).

FIG. 11 shows the results of real-time expression analysis of LTBP2 in rat hearts (DOCA). X axis: treatment; Y axis: relative expression; A: control; B: control/placebo; C: compound P/concentration 1; D: compound P/concentration 2. The expression of LTBP2 is disease state, treatment- and dose-dependent regulated in the animal model.

FIG. 12 shows the results of real-time expression analysis of LTBP2 in rat hearts (occlusion). X axis: treatment; Y axis: relative expression; A: control; B: control/placebo; C: compound P/concentration 1; D: compound P/concentration 2. The expression of LTBP2 is disease state, treatment- and dose-dependent regulated in the animal model.

DETAILED DESCRIPTION OF THE INVENTION

Definition of Terms

Figure 13:
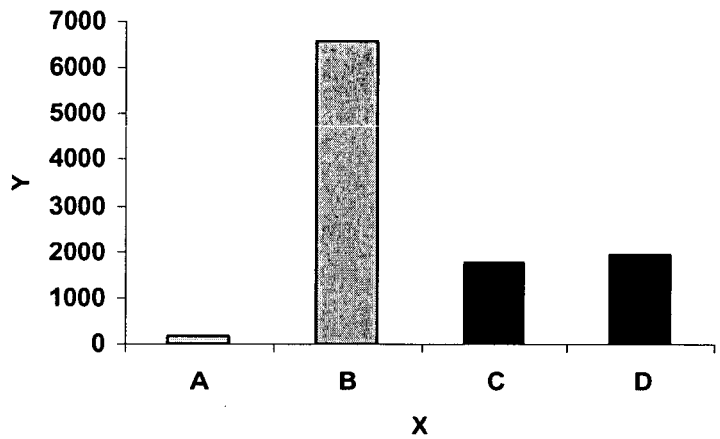
FIG. 13 shows the results of real-time expression analysis of LTBP2 in rat hearts (monocrotalin). X axis: treatment; Y axis: relative expression; A: control; B: control/placebo; C: compound P/concentration 1; D: compound P/concentration 2. The expression of LTBP2 is disease state, treatment- and dose-dependent regulated in the animal model.
Figure 14:
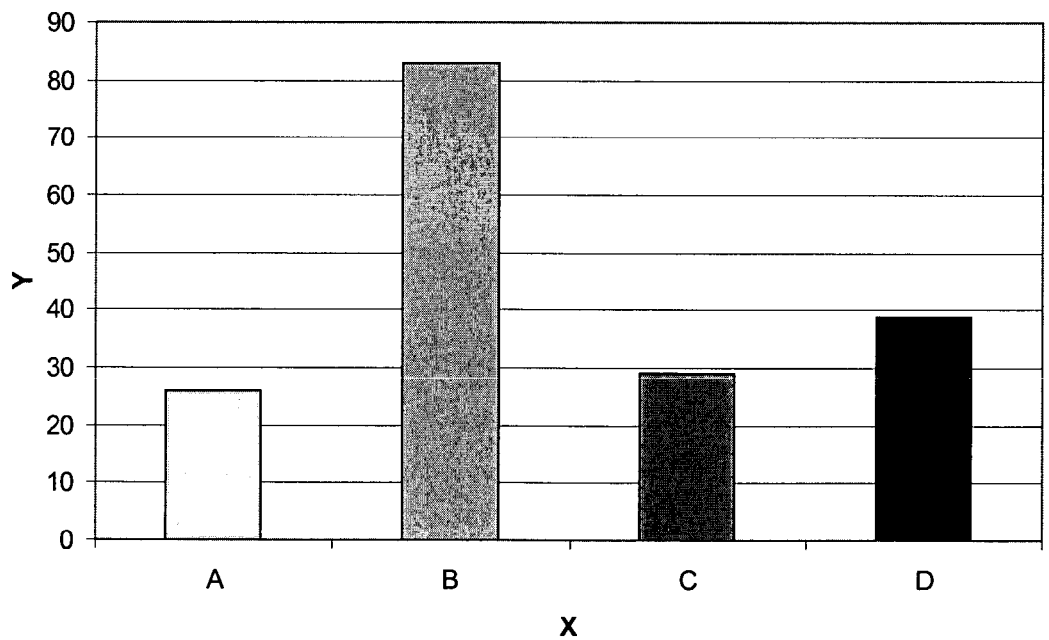
FIG. 14 shows the results of microarray expression analysis of LTBP2 in rat hearts (Doca). X axis: treatment; Y axis: relative expression; A: control; B: control/placebo; C: compound P/concentration 1; D: compound P/concentration 2. The expression of LTBP2 is disease state, treatment- and dose-dependent regulated in the animal model.
Figure 15:
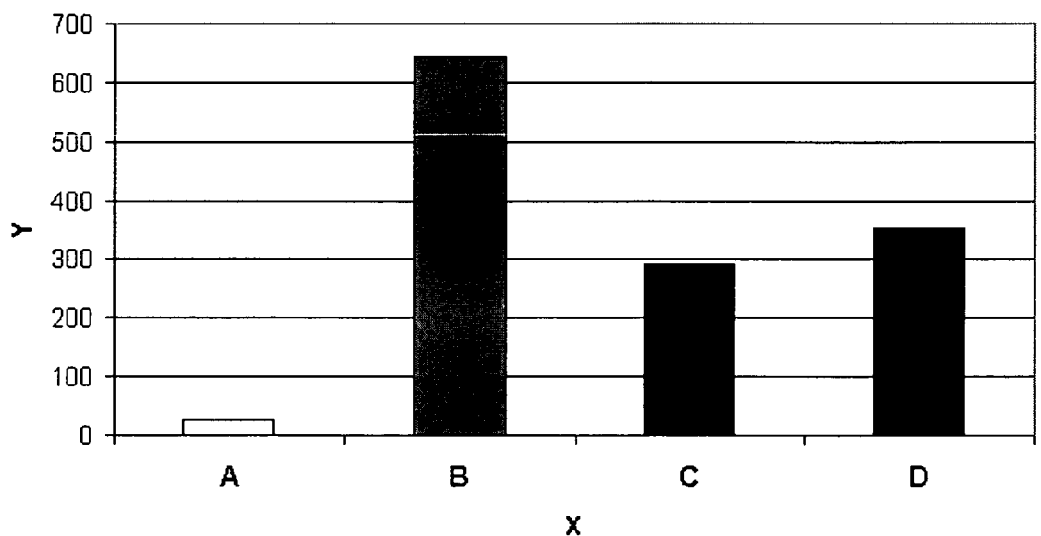
FIG. 15 shows the results of microarray expression analysis of LTBP2 in rat hearts (Occlusion). X axis: treatment; Y axis: relative expression; A: control; B: control/placebo; C: compound P/concentration 1; D: compound P/concentration 2. The expression of LTBP2 is disease state, treatment- and dose-dependent regulated in the animal model.
Figure 16:
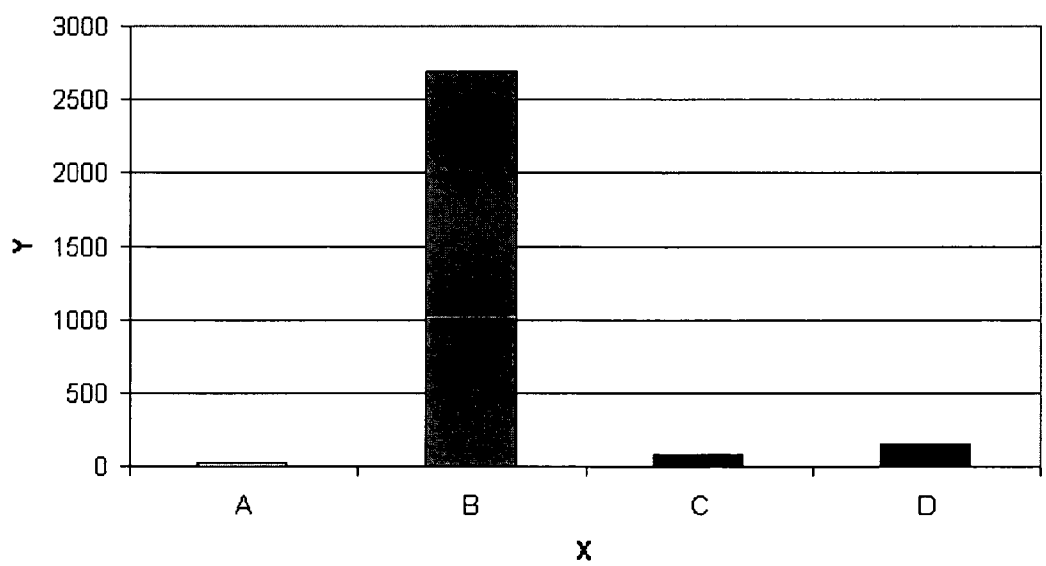
FIG. 16 shows the results of microarray expression analysis of LTBP2 in rat hearts (monocrotalin). X axis: treatment; Y axis: relative expression; A: control; B: control/placebo; C: compound P/concentration 1; D: compound P/concentration 2. The expression of LTBP2 is disease state, treatment- and dose-dependent regulated in the animal model.
Figure 17:
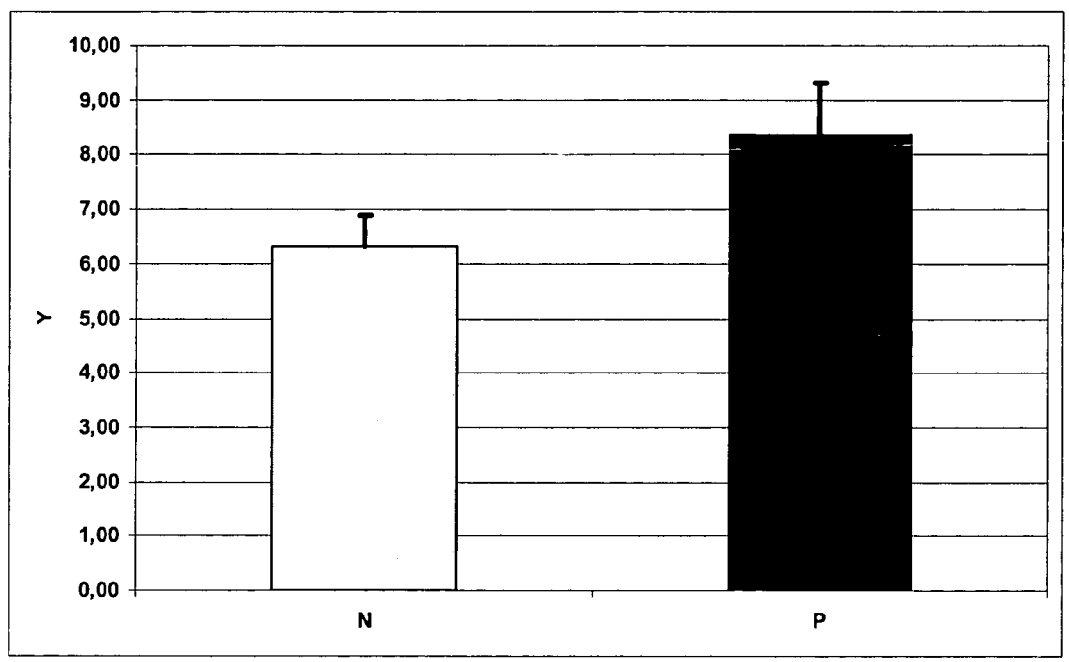
FIG. 17 shows the results of microarray expression analysis of LTBP2 in human hearts. X axis: disease status; Y axis: relative expression; N: non-failure; P: pre-LVAD. The expression of LTBP2 is disease state regulated in human heart.

An "oligonucleotide" is a stretch of nucleotide residues which has a sufficient number of bases to be used as an oligomer, amplimer or probe in a polymerase chain reaction (PCR). Oligonucleotides are prepared from genomic or cDNA sequence and are used to amplify, reveal, or confirm the presence of a similar DNA or RNA in a particular cell or tissue. Oligonucleotides or oligomers comprise portions of a DNA sequence having at least about 10 nucleotides and as many as about 35 nucleotides, preferably about 25 nucleotides.

"Probes" may be derived from naturally occurring or recombinant single- or double-stranded nucleic acids or may be chemically synthesized. They are useful in detecting the presence of identical or similar sequences. Such probes may be labeled with reporter molecules using nick translation, Klenow fill-in reaction, PCR or other methods well known in the art. Nucleic acid probes may be used in southern, northern or in situ hybridizations to determine whether DNA or RNA encoding a certain protein is present in a cell type, tissue, or organ.

A "fragment of a polynucleotide" is a nucleic acid that comprises all or any part of a given nucleotide molecule, the fragment having fewer nucleotides than about 6 kb, preferably fewer than about 1 kb.

"Reporter molecules" are radionuclides, enzymes, fluorescent, chemiluminescent, or chromogenic agents which associate with a particular nucleotide or amino acid sequence, thereby establishing the presence of a certain sequence, or allowing for the quantification of a certain sequence.

"Chimeric" molecules may be constructed by introducing all or part of the nucleotide sequence of this invention into a vector containing additional nucleic acid sequence which might be expected to change any one or several of the following LTBP2 characteristics: cellular location, distribution, ligand-binding affinities, interchain affinities, degradation/turnover rate, signaling, etc.

"Active", with respect to a LTBP2 polypeptide, refers to those forms, fragments, or domains of a LTBP2 polypeptide which retain the biological and/or antigenic activity of a LTBP2 polypeptide.

"Naturally occurring LTBP2 polypeptide" refers to a polypeptide produced by cells which have not been genetically engineered and specifically contemplates various polypeptides arising from post-translational modifications of the polypeptide including but not limited to acetylation, carboxylation, glycosylation, phosphorylation, lipidation and acylation.

"Derivative" refers to polypeptides which have been chemically modified by techniques such as ubiquitination, labeling (see above), pegylation (derivatization with polyethylene glycol), and chemical insertion or substitution of amino acids such as ornithine which do not normally occur in human proteins.

"Conservative amino acid substitutions" result from replacing one amino acid with another having similar structural and/or chemical properties, such as the replacement of a leucine with an isoleucine or valine, an aspartate with a glutamate, or a threonine with a serine.

"Insertions" or "deletions" are typically in the range of about 1 to 5 amino acids. The variation allowed may be experimentally determined by producing the peptide synthetically while systematically making insertions, deletions, or substitutions of nucleotides in the sequence using recombinant DNA techniques.

A "signal sequence" or "leader sequence" can be used, when desired, to direct the polypeptide through a membrane of a cell. Such a sequence may be naturally present on the polypeptides of the present invention or provided from heterologous sources by recombinant DNA techniques.

An "oligopeptide" is a short stretch of amino acid residues and may be expressed from an oligonucleotide. Oligopeptides comprise a stretch of amino acid residues of at least 3, 5, 10 amino acids and at most 10, 15, 25 amino acids, typically of at least 9 to 13 amino acids, and of sufficient length to display biological and/or antigenic activity.

"Inhibitor" is any substance which retards or prevents a chemical or physiological reaction or response. Common inhibitors include but are not limited to antisense molecules, antibodies, and antagonists.

"Biomarker" are measurable and quantifiable biological parameters (e.g. specific enzyme concentration, specific hormone concentration, specific gene phenotype distribution in a population, presence of biological substances) which serve as indices for health—and physiology related assessments, such as disease risk, psychiatric disorders, environmental exposure and its effects, disease diagnosis, metabolic processes, substance abuse, pregnancy, cell line development, epidemiologic studies, etc. Parameter that can be used to identify a toxic effect in an individual organism and can be used in extrapolation between species. Indicator signalling an event or condition in a biological system or sample and giving a measure of exposure, effect, or susceptibility.

Biological markers can reflect a variety of disease characteristics, including the level of exposure to an environmental or genetic trigger, an element of the disease process itself, an intermediate stage between exposure and disease onset, or an independent factor associated with the disease state but not causative of pathogenesis. Depending on the specific characteristic, biomarkers can be used to identify the risk of developing an illness (antecedent biomarkers), aid in identifying disease (diagnostic biomarkers), or predict future disease course, including response to therapy (prognostic biomarkers).

"Standard expression" is a quantitative or qualitative measurement for comparison. It is based on a statistically appropriate number of normal samples and is created to use as a basis of comparison when performing diagnostic assays, running clinical trials, or following patient treatment profiles.

"Animal" as used herein may be defined to include human, domestic (e.g., cats, dogs, etc.), agricultural (e.g., cows, horses, sheep, etc.) or test species (e.g., mouse, rat, rabbit, etc.).

A "LTBP2 polynucleotide", within the meaning of the invention, shall be understood as being a nucleic acid molecule selected from a group consisting of
(i) nucleic acid molecules encoding a polypeptide comprising the amino acid sequence of SEQ ID NO: 3 or SEQ ID NO: 4,
(ii) nucleic acid molecules comprising the sequence of SEQ ID NO: 1 or SEQ ID NO: 2,
(iii) nucleic acid molecules having the sequence of SEQ ID NO: 1 or SEQ ID NO: 2,
(iv) nucleic acid molecules the complementary strand of which hybridizes under stringent conditions to a nucleic acid molecule of (i), (ii), or (iii),
(v) nucleic acid molecules the sequence of which differs from the sequence of a nucleic acid molecule of (iii) due to the degeneracy of the genetic code,
(vi) nucleic acid molecules which have a sequence identity of at least 80%, 85%, 90%, 95%, 98% or 99%; and
(vii) wherein the polypeptide encoded by said nucleic acid molecules of (i)-(vi) have LTBP2 activity A "LTBP2 polypeptide", within the meaning of the invention, shall be understood as being a polypeptide selected from a group consisting of
(i) polypeptides having the sequence of SEQ ID NO: 3 or 4,
(ii) polypeptides comprising the sequence of SEQ ID NO: 3 or 4,
(iii) polypeptides encoded by LTBP2 polynucleotides; and
(iv) polypeptides which show at least 99%, 98%, 95%, 90%, or 80% identity with a polypeptide of (i), (ii), or (iii);
wherein said polypeptide has LTBP2 activity.

The nucleotide sequences encoding a LTBP2 (or their complement) have numerous applications in techniques known to those skilled in the art of molecular biology. These techniques include use as hybridization probes, use in the construction of oligomers for PCR, use for chromosome and gene mapping, use in the recombinant production of LTBP2, and use in generation of antisense DNA or RNA, their chemical analogs and the like. Uses of nucleotides encoding a LTBP2 disclosed herein are exemplary of known techniques and are not intended to limit their use in any technique known to a person of ordinary skill in the art. Furthermore, the nucleotide sequences disclosed herein may be used in molecular biology techniques that have not yet been developed, provided the new techniques rely on properties of nucleotide sequences that are currently known, e.g., the triplet genetic code, specific base pair interactions, etc.

It will be appreciated by those skilled in the art that as a result of the degeneracy of the genetic code, a multitude of LTBP2-encoding nucleotide sequences may be produced. Some of these will only bear minimal homology to the nucleotide sequence of the known and naturally occurring LTBP2. The invention has specifically contemplated each and every possible variation of nucleotide sequence that could be made by selecting combinations based on possible codon choices. These combinations are made in accordance with the standard triplet genetic code as applied to the nucleotide sequence of naturally occurring LTBP2, and all such variations are to be considered as being specifically disclosed.

Although the nucleotide sequences which encode a LTBP2, its derivatives or its variants are preferably capable of hybridizing to the nucleotide sequence of the naturally occurring LTBP2 polynucleotide under stringent conditions, it may be advantageous to produce nucleotide sequences encoding LTBP2 polypeptides or its derivatives possessing a substantially different codon usage. Codons can be selected to increase the rate at which expression of the peptide occurs in a particular prokaryotic or eukaryotic expression host in accordance with the frequency with which particular codons are utilized by the host. Other reasons for substantially altering the nucleotide sequence encoding a LTBP2 polypeptide and/or its derivatives without altering the encoded amino acid sequence include the production of RNA transcripts having more desirable properties, such as a greater half-life, than transcripts produced from the naturally occurring sequence.

Nucleotide sequences encoding a LTBP2 polypeptide may be joined to a variety of other nucleotide sequences by means of well established recombinant DNA techniques. Useful nucleotide sequences for joining to LTBP2 polynucleotides include an assortment of cloning vectors such as plasmids, cosmids, lambda phage derivatives, phagemids, and the like. Vectors of interest include expression vectors, replication vectors, probe generation vectors, sequencing vectors, etc. In general, vectors of interest may contain an origin of replication functional in at least one organism, convenient restriction endonuclease sensitive sites, and selectable markers for one or more host cell systems.

Another aspect of the subject invention is to provide for LTBP2-specific hybridization probes capable of hybridizing with naturally occurring nucleotide sequences encoding LTBP2. Such probes may also be used for the detection of similar protein encoding sequences and should preferably show at least 40% nucleotide identity to LTBP2 polynucleotides. The hybridization probes of the subject invention may be derived from the nucleotide sequence presented as SEQ ID NO: 1 or from genomic sequences including promoter, enhancers or introns of the native gene. Hybridization probes may be labelled by a variety of reporter molecules using techniques well known in the art.

It will be recognized that many deletional or mutational analogs of LTBP2 polynucleotides will be effective hybridization probes for LTBP2 polynucleotides. Accordingly, the invention relates to nucleic acid sequences that hybridize with such LTBP2 encoding nucleic acid sequences under stringent conditions.

"Stringent conditions" refers to conditions that allow for the hybridization of substantially related nucleic acid sequences. For instance, such conditions will generally allow hybridization of sequence with at least about 85% sequence identity, preferably with at least about 90% sequence identity, more preferably with at least about 95% sequence identity. Hybridization conditions and probes can be adjusted in well-characterized ways to achieve selective hybridization of human-derived probes. Stringent conditions, within the meaning of the invention are 68° C. in a buffer containing 0.2×SSC (1×standard saline-citrate=150 mM NaCl, 15 mM Trinatriumcitrat) [Sambrook et al., (1989)].

Nucleic acid molecules that will hybridize to LTBP2 polynucleotides under stringent conditions can be identified functionally. Without limitation, examples of the uses for hybridization probes include: histochemical uses such as identifying tissues that express LTBP2; measuring mRNA levels, for instance to identify a sample's tissue type or to identify cells that express abnormal levels of LTBP2; and detecting polymorphisms of LTBP2.

PCR provides additional uses for oligonucleotides based upon the nucleotide sequence which encodes LTBP2. Such probes used in PCR may be of recombinant origin, chemically synthesized, or a mixture of both. Oligomers may comprise discrete nucleotide sequences employed under optimized conditions for identification of LTBP2 in specific tissues or diagnostic use. The same two oligomers, a nested set of oligomers, or even a degenerate pool of oligomers may be employed under less stringent conditions for identification of closely related DNAs or RNAs.

Rules for designing polymerase chain reaction (PCR) primers are now established, as reviewed by PCR Protocols. Degenerate primers, i.e., preparations of primers that are heterogeneous at given sequence locations, can be designed to amplify nucleic acid sequences that are highly homologous to, but not identical with LTBP2. Strategies are now available that allow for only one of the primers to be required to specifically hybridize with a known sequence. For example, appropriate nucleic acid primers can be ligated to the nucleic acid sought to be amplified to provide the hybridization partner for one of the primers. In this way, only one of the primers need be based on the sequence of the nucleic acid sought to be amplified.

PCR methods for amplifying nucleic acid will utilize at least two primers. One of these primers will be capable of hybridizing to a first strand of the nucleic acid to be amplified and of priming enzyme-driven nucleic acid synthesis in a first direction. The other will be capable of hybridizing the reciprocal sequence of the first strand (if the sequence to be amplified is single stranded, this sequence will initially be hypothetical, but will be synthesized in the first amplification cycle) and of priming nucleic acid synthesis from that strand in the direction opposite the first direction and towards the site of hybridization for the first primer. Conditions for conducting such amplifications, particularly under preferred stringent hybridization conditions, are well known.

Other means of producing specific hybridization probes for LTBP2 include the cloning of nucleic acid sequences encoding LTBP2 or LTBP2 derivatives into vectors for the production of mRNA probes. Such vectors are known in the art, are commercially available and may be used to synthesize RNA probes in vitro by means of the addition of the appropriate RNA polymerase as T7 or SP6 RNA polymerase and the appropriate reporter molecules.

It is possible to produce a DNA sequence, or portions thereof, entirely by synthetic chemistry. After synthesis, the nucleic acid sequence can be inserted into any of the many available DNA vectors and their respective host cells using techniques which are well known in the art. Moreover, synthetic chemistry may be used to introduce mutations into the nucleotide sequence. Alternately, a portion of sequence in which a mutation is desired can be synthesized and recombined with longer portion of an existing genomic or recombinant sequence.

LTBP2 polynucleotides may be used to produce a purified oligo- or polypeptide using well known methods of recombinant DNA technology. The oligopeptide may be expressed in a variety of host cells, either prokaryotic or eukaryotic. Host cells may be from the same species from which the nucleotide sequence was derived or from a different species. Advantages of producing an oligonucleotide by recombinant DNA technology include obtaining adequate amounts of the protein for purification and the availability of simplified purification procedures.

Quantitative Determinations of Nucleic Acids

An important step in the molecular genetic analysis of human disease is often the enumeration of the copy number of a nucleus acid or the relative expression of a gene in particular tissues.

Several different approaches are currently available to make quantitative determinations of nucleic acids. Chromosome-based techniques, such as comparative genomic hybridization (CGH) and fluorescent in situ hybridization (FISH) facilitate efforts to cytogenetically localize genomic regions that are altered in tumor cells. Regions of genomic alteration can be narrowed further using loss of heterozygosity analysis (LOH), in which disease DNA is analyzed and compared with normal DNA for the loss of a heterozygous polymorphic marker. The first experiments used restriction fragment length polymorphisms (RFLPs) [Johnson, (1989)], or hypervariable mini-satellite DNA [Barnes, 2000]. In recent years LOH has been performed primarily using PCR amplification of microsatellite markers and electrophoresis of the radio labelled [Jeffreys, (1985)] or fluorescently labelled PCR products [Weber, (1990)] and compared between paired normal and disease DNAs.

A number of other methods have also been developed to quantify nucleic acids [Gergen, (1992)]. More recently, PCR and RT-PCR methods have been developed which are capable of measuring the amount of a nucleic acid in a sample. One approach, for example, measures PCR product quantity in the log phase of the reaction before the formation of reaction products plateaus [Thomas, (1980)].

A gene sequence contained in all samples at relatively constant quantity is typically utilized for sample amplification efficiency normalization. This approach, however, suffers from several drawbacks. The method requires that each sample has equal input amounts of the nucleic acid and that the amplification efficiency between samples is identical until the time of analysis. Furthermore, it is difficult using the conventional methods of PCR quantitation such as gel electrophoresis or plate capture hybridization to determine that all samples are in fact analyzed during the log phase of the reaction as required by the method.

Another method called quantitative competitive (QC)-PCR, as the name implies, relies on the inclusion of an internal control competitor in each reaction [Piatak, (1993), Bio-Techniques]. The efficiency of each reaction is normalized to the internal competitor. A known amount of internal competitor is typically added to each sample. The unknown target PCR product is compared with the known competitor PCR product to obtain relative quantitation. A difficulty with this general approach lies in developing an internal control that amplifies with the same efficiency than the target molecule.

5' Fluorogenic Nuclease Assays

Fluorogenic nuclease assays are a real time quantitation method that uses a probe to monitor formation of amplification product. The basis for this method of monitoring the formation of amplification product is to measure continuously PCR product accumulation using a dual-labelled fluorogenic oligonucleotide probe, an approach frequently referred to in the literature simply as the "TaqMan method" [Piatak, (1993), Science; Heid, (1996); Gibson, (1996); Holland. (1991)].

The probe used in such assays is typically a short (about 20-25 bases) oligonucleotide that is labeled with two different fluorescent dyes. The 5' terminus of the probe is attached to a reporter dye and the 3' terminus is attached to a quenching dye, although the dyes could be attached at other locations on the probe as well. The probe is designed to have at least substantial sequence complementarity with the probe binding site. Upstream and downstream PCR primers which bind to flanking regions of the locus are added to the reaction mixture. When the probe is intact, energy transfer between the two fluorophors occurs and the quencher quenches emission from the reporter. During the extension phase of PCR, the probe is cleaved by the 5' nuclease activity of a nucleic acid polymerase such as Taq polymerase, thereby releasing the reporter from the oligonucleotide-quencher and resulting in an increase of reporter emission intensity which can be measured by an appropriate detector.

One detector which is specifically adapted for measuring fluorescence emissions such as those created during a fluorogenic assay is the ABI 7700 or 4700 HT manufactured by Applied Biosystems, Inc. in Foster City, Calif. The ABI 7700 uses fiber optics connected with each well in a 96- or 384 well PCR tube arrangement. The instrument includes a laser for exciting the labels and is capable of measuring the fluorescence spectra intensity from each tube with continuous monitoring during PCR amplification. Each tube is re-examined every 8.5 seconds.

Computer software provided with the instrument is capable of recording the fluorescence intensity of reporter and quencher over the course of the amplification. The recorded values will then be used to calculate the increase in normalized reporter emission intensity on a continuous basis. The increase in emission intensity is plotted versus time, i.e., the number of amplification cycles, to produce a continuous measure of amplification. To quantify the locus in each amplification reaction, the amplification plot is examined at a point during the log phase of product accumulation. This is accomplished by assigning a fluorescence threshold intensity above background and determining the point at which each amplification plot crosses the threshold (defined as the threshold cycle number or Ct). Differences in threshold cycle number are used to quantify the relative amount of PCR target contained within each tube. Assuming that each reaction functions at 100% PCR efficiency, a difference of one Ct represents a two-fold difference in the amount of starting template. The fluorescence value can be used in conjunction with a standard curve to determine the amount of amplification product present.

Non-Probe-Based Detection Methods

A variety of options are available for measuring the amplification products as they are formed. One method utilizes labels, such as dyes, which only bind to double stranded DNA. In this type of approach, amplification product (which is double stranded) binds dye molecules in solution to form a complex. With the appropriate dyes, it is possible to distinguish between dye molecules free in solution and dye molecules bound to amplification product. For example, certain dyes fluoresce only when bound to amplification product. Examples of dyes which can be used in methods of this general type include, but are not limited to, Syber Green™ and Pico Green from Molecular Probes, Inc. of Eugene, Oreg., ethidium bromide, propidium iodide, chromomycin, acridine orange, Hoechst 33258, Toto-1, Yoyo-1, DAPI (4',6-diamidino-2-phenylindole hydrochloride).

Another real time detection technique measures alteration in energy fluorescence energy transfer between fluorophors conjugated with PCR primers [Livak, (1995)].

Probe-Based Detection Methods

These detection methods involve some alteration to the structure or conformation of a probe hybridized to the locus between the amplification primer pair. In some instances, the alteration is caused by the template-dependent extension catalyzed by a nucleic acid polymerase during the amplification process. The alteration generates a detectable signal which is an indirect measure of the amount of amplification product formed.

For example, some methods involve the degradation or digestion of the probe during the extension reaction. These methods are a consequence of the 5'-3' nuclease activity associated with some nucleic acid polymerases. Polymerases having this activity cleave mononucleotides or small oligonucleotides from an oligonucleotide probe annealed to its complementary sequence located within the locus.

The 3' end of the upstream primer provides the initial binding site for the nucleic acid polymerase. As the polymerase catalyzes extension of the upstream primer and encounters the bound probe, the nucleic acid polymerase displaces a portion of the 5' end of the probe and through its nuclease activity cleaves mononucleotides or oligonucleotides from the probe.

The upstream primer and the probe can be designed such that they anneal to the complementary strand in close proximity to one another. In fact, the 3' end of the upstream primer and the 5' end of the probe may abut one another. In this situation, extension of the upstream primer is not necessary in order for the nucleic acid polymerase to begin cleaving the probe. In the case in which intervening nucleotides separate the upstream primer and the probe, extension of the primer is necessary before the nucleic acid polymerase encounters the 5' end of the probe. Once contact occurs and polymerization continues, the 5'-3' exonuclease activity of the nucleic acid polymerase begins cleaving mononucleotides or oligonucleotides from the 5' end of the probe. Digestion of the probe continues until the remaining portion of the probe dissociates from the complementary strand.

In solution, the two end sections can hybridize with each other to form a hairpin loop. In this conformation, the reporter and quencher dye are in sufficiently close proximity that fluorescence from the reporter dye is effectively quenched by the quencher dye. Hybridized probe, in contrast, results in a linearized conformation in which the extent of quenching is decreased. Thus, by monitoring emission changes for the two dyes, it is possible to indirectly monitor the formation of amplification product.

Probes

The labeled probe is selected so that its sequence is substantially complementary to a segment of the test locus or a reference locus. As indicated above, the nucleic acid site to which the probe binds should be located between the primer binding sites for the upstream and downstream amplification primers.

Primers

The primers used in the amplification are selected so as to be capable of hybridizing to sequences at flanking regions of the locus being amplified. The primers are chosen to have at least substantial complementarity with the different strands of the nucleic acid being amplified. When a probe is utilized to detect the formation of amplification products, the primers are selected in such that they flank the probe, i.e. are located upstream and downstream of the probe.

The primer must have sufficient length so that it is capable of priming the synthesis of extension products in the presence of an agent for polymerization. The length and composition of the primer depends on many parameters, including, for example, the temperature at which the annealing reaction is conducted, proximity of the probe binding site to that of the primer, relative concentrations of the primer and probe and the particular nucleic acid composition of the probe. Typically the primer includes 15-30 nucleotides. However, the length of the primer may be more or less depending on the complexity of the primer binding site and the factors listed above.

Labels for Probes and Primers

The labels used for labeling the probes or primers of the current invention and which can provide the signal corresponding to the quantity of amplification product can take a variety of forms. As indicated above with regard to the 5' fluorogenic nuclease method, a fluorescent signal is one signal which can be measured. However, measurements may also be made, for example, by monitoring radioactivity, colorimetry, absorption, magnetic parameters, or enzymatic activity. Thus, labels which can be employed include, but are not limited to, fluorophors, chromophores, radioactive isotopes, electron dense reagents, enzymes, and ligands having specific binding partners (e.g., biotin-avidin).

Monitoring changes in fluorescence is a particularly useful way to monitor the accumulation of amplification products. A number of labels useful for attachment to probes or primers are commercially available including fluorescein and various fluorescein derivatives such as FAM, HEX, TET and JOE (all which are available from Applied Biosystems, Foster City, Calif.); lucifer yellow, and coumarin derivatives.

Labels may be attached to the probe or primer using a variety of techniques and can be attached at the 5' end, and/or the 3' end and/or at an internal nucleotide. The label can also be attached to spacer arms of various sizes which are attached to the probe or primer. These spacer arms are useful for obtaining a desired distance between multiple labels attached to the probe or primer.

In some instances, a single label may be utilized; whereas, in other instances, such as with the 5' fluorogenic nuclease assays for example, two or more labels are attached to the probe. In cases wherein the probe includes multiple labels, it is generally advisable to maintain spacing between the labels which is sufficient to permit separation of the labels during digestion of the probe through the 5'-3' nuclease activity of the nucleic acid polymerase.

Microarray

Nucleic acid arrays that have been used in the present invention are those that are commercially available from Affymetrix (Santa Clara, Calif.) under the brand name GeneChip Human Genome U133 Plus 2.0 Array.® or Rat Genome U230 plus 2.0 Array respectively which represents the complete coverage of the Human Genome U133 Set plus 9921 probe sets representing approximately 6,500 new genes (with a total of approximately 56 000 transcripts) or the Rat Genome respectively. Affymetrix (Santa Clara, Calif.) GeneChip technology platform which consists of high-density microarrays and tools to help process and analyze those arrays, including standardized assays and reagents, instrumentation, and data management and analysis tools.

GeneChip microarrays consist of small DNA fragments (referred to as probes), chemically synthesized at specific locations on a coated quartz surface. By extracting and labeling nucleic acids from experimental samples, and then hybridizing those prepared samples to the array, the amount of label can be monitored enabling a measurement of gene regulation The GeneChip human genome arrays include a set of human maintenance genes to facilitate the normalization and scaling of array experiments and to perform data comparison. This set of normalization genes shows consistent levels of expression over a diverse set of tissues.

Patients Exhibiting Symptoms of Disease

A number of diseases are associated with changes in the copy number of a certain gene. For patients having symptoms of a disease, the real-time PCR method can be used to determine if the patient has copy number alterations which are known to be linked with diseases that are associated with the symptoms the patient has.

LTBP2 Expression

LTBP2 Fusion Proteins

Fusion proteins are useful for generating antibodies against LTBP2 polypeptides and for use in various assay systems. For example, fusion proteins can be used to identify proteins which interact with portions of LTBP2 polypeptides. Protein affinity chromatography or library-based assays for protein-protein interactions, such as the yeast two-hybrid or phage display systems, can be used for this purpose. Such methods are well known in the art and also can be used as drug screens.

A LTBP2 fusion protein comprises two polypeptide segments fused together by means of a peptide bond. The first polypeptide segment can comprise at least 54, 75, 100, 125, 139, 150, 175, 200, 225, 250, 275, 300, 325 or 350 contiguous amino acids of SEQ ID NO: 3 or 4 or of a variant, such as those described above. The first polypeptide segment also can comprise full-length LTBP2.

The second polypeptide segment can be a full-length protein or a protein fragment. Proteins commonly used in fusion protein construction include, but are not limited to β galactosidase, β-glucuronidase, green fluorescent protein (GFP), autofluorescent proteins, including blue fluorescent protein (BFP), glutathione-S-transferase (GST), luciferase, horseradish peroxidase (HRP), and chloramphenicol acetyltransferase (CAT). Additionally, epitope tags are used in fusion protein constructions, including histidine (His) tags, FLAG tags, influenza hemagglutinin (HA) tags, Myc tags, VSV-G tags, and thioredoxin (Trx) tags. Other fusion constructions can include maltose binding protein (MBP), S-tag, Lex a DNA binding domain (DBD) fusions, GAL4 DNA binding domain fusions, and herpes simplex virus (HSV) BP16 protein fusions. A fusion protein also can be engineered to contain a cleavage site located adjacent to the LTBP2.

Preparation of Polynucleotides

A naturally occurring LTBP2 polynucleotide can be isolated free of other cellular components such as membrane components, proteins, and lipids. Polynucleotides can be made by a cell and isolated using standard nucleic acid purification techniques, or synthesized using an amplification technique, such as the polymerase chain reaction (PCR), or by using an automatic synthesizer. Methods for isolating polynucleotides are routine and are known in the art. Any such technique for obtaining a polynucleotide can be used to obtain isolated LTBP2 polynucleotides. For example, restriction enzymes and probes can be used to isolate polynucleotide fragments which comprise LTBP2 nucleotide sequences. Isolated polynucleotides are in preparations which are free or at least 70, 80, or 90% free of other molecules.

LTBP2 cDNA molecules can be made with standard molecular biology techniques, using LTBP2 mRNA as a template. LTBP2 cDNA molecules can thereafter be replicated using molecular biology techniques known in the art. An amplification technique, such as PCR, can be used to obtain additional copies of polynucleotides of the invention, using either human genomic DNA or cDNA as a template.

Alternatively, synthetic chemistry techniques can be used to synthesizes LTBP2 polynucleotides. The degeneracy of the genetic code allows alternate nucleotide sequences to be synthesized which will encode LTBP2 having, for example, an amino acid sequence shown in SEQ ID NO: 2 or a biologically active variant thereof.

Extending Polynucleotides

Various PCR-based methods can be used to extend nucleic acid sequences encoding human LTBP2, for example to detect upstream sequences of LTBP2 gene such as promoters and regulatory elements. For example, restriction-site PCR uses universal primers to retrieve unknown sequence adjacent to a known locus. Genomic DNA is first amplified in the presence of a primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR also can be used to amplify or extend sequences using divergent primers based on a known region. Primers can be designed using commercially available software, such as OLIGO 4.06 Primer Analysis software (National Biosciences Inc., Plymouth, Minn.), to be 22-30 nucleotides in length, to have a GC content of 50% or more, and to anneal to the target sequence at temperatures about 68-72° C. The method uses several restriction enzymes to generate a suitable fragment in the known region of a gene. The fragment is then circularized by intramolecular ligation and used as a PCR template.

Another method which can be used is capture PCR, which involves PCR amplification of DNA fragments adjacent to a known sequence in human and yeast artificial chromosome DNA. In this method, multiple restriction enzyme digestions and ligations also can be used to place an engineered double-stranded sequence into an unknown fragment of the DNA molecule before performing PCR.

When screening for full-length cDNAs, it is preferable to use libraries that have been size-selected to include larger cDNAs. Randomly-primed libraries are preferable, in that they will contain more sequences which contain the 5' regions of genes. Use of a randomly primed library may be especially preferable for situations in which an oligo d(T) library does not yield a full-length cDNA. Genomic libraries can be useful for extension of sequence into 5' non-transcribed regulatory regions.

Commercially available capillary electrophoresis systems can be used to analyze the size or confirm the nucleotide sequence of PCR or sequencing products. For example, capillary sequencing can employ flowable polymers for electrophoretic separation, four different fluorescent dyes (one for each nucleotide) which are laser activated, and detection of the emitted wavelengths by a charge coupled device camera. Output/light intensity can be converted to electrical signal using appropriate equipment and software (e.g., GENOTYPER and Sequence NAVIGATOR, Perkin Elmer), and the entire process from loading of samples to computer analysis and electronic data display can be computer controlled. Capillary electrophoresis is especially preferable for the sequencing of small pieces of DNA which might be present in limited amounts in a particular sample.

Obtaining Polypeptides

LTBP2 can be obtained, for example, by purification from human cells, by expression of LTBP2 polynucleotides, or by direct chemical synthesis.

Protein Purification

LTBP2 can be purified from any human cell which expresses the enzyme, including those which have been transfected with expression constructs which express LTBP2. A purified LTBP2 is separated from other compounds which normally associate with LTBP2 in the cell, such as certain proteins, carbohydrates, or lipids, using methods well-known in the art. Such methods include, but are not limited to, size exclusion chromatography, ammonium sulfate fractionation, ion exchange chromatography, affinity chromatography, and preparative gel electrophoresis.

Expression of LTBP2 Polynucleotides

To express LTBP2, LTBP2 polynucleotides can be inserted into an expression vector which contains the necessary elements for the transcription and translation of the inserted coding sequence. Methods which are well known to those skilled in the art can be used to construct expression vectors containing sequences encoding LTBP2 and appropriate transcriptional and translational control elements. These methods include in vitro recombinant DNA techniques, synthetic techniques, and in vivo genetic recombination.

A variety of expression vector/host systems can be utilized to contain and express sequences encoding LTBP2. These include, but are not limited to, microorganisms, such as bacteria transformed with recombinant bacteriophage, plasmid, or cosmid DNA expression vectors; yeast transformed with yeast expression vectors, insect cell systems infected with virus expression vectors (e.g., baculovirus), plant cell systems transformed with virus expression vectors (e.g., cauliflower mosaic virus, CaMV; tobacco mosaic virus, TMV) or with bacterial expression vectors (e.g., Ti or pBR322 plasmids), or animal cell systems.

The control elements or regulatory sequences are those non-translated regions of the vector—enhancers, promoters, 5' and 3' untranslated regions—which interact with host cellular proteins to carry out transcription and translation. Such elements can vary in their strength and specificity. Depending on the vector system and host utilized, any number of suitable transcription and translation elements, including constitutive and inducible promoters, can be used. For example, when cloning in bacterial systems, inducible promoters such as the hybrid lacZ promoter of the BLUESCRIPT phagemid (Stratagene, LaJolla, Calif.) or pSPORT1 plasmid (Life Technologies) and the like can be used. The baculovirus polyhedrin promoter can be used in insect cells. Promoters or enhancers derived from the genomes of plant cells (e.g., heat shock, RUBISCO, and storage protein genes) or from plant viruses (e.g., viral promoters or leader sequences) can be cloned into the vector. In mammalian cell systems, promoters from mammalian genes or from mammalian viruses are preferable. If it is necessary to generate a cell line that contains multiple copies of a nucleotide sequence encoding LTBP2, vectors based on SV40 or EBV can be used with an appropriate selectable marker.

Bacterial and Yeast Expression Systems

In bacterial systems, a number of expression vectors can be selected. For example, when a large quantity of LTBP2 is needed for the induction of antibodies, vectors which direct high level expression of fusion proteins that are readily purified can be used. Such vectors include, but are not limited to, multifunctional *E. coli* cloning and expression vectors such as BLUESCRIPT (Stratagene). In a BLUESCRIPT vector, a sequence encoding LTBP2 can be ligated into the vector in frame with sequences for the amino-terminal Met and the subsequent 7 residues of β-galactosidase so that a hybrid protein is produced. pIN vectors or pGEX vectors (Promega, Madison, Wis.) also can be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems can be designed to include heparin, thrombin, or factor Xa protease cleavage sites so that the cloned polypeptide of interest can be released from the GST moiety at will.

Plant and Insect Expression Systems

If plant expression vectors are used, the expression of sequences encoding LTBP2 can be driven by any of a number of promoters. For example, viral promoters such as the 35S and 19S promoters of CaMV can be used alone or in combination with the omega leader sequence from TMV. Alternatively, plant promoters such as the small subunit of RUBISCO or heat shock promoters can be used. These constructs can be introduced into plant cells by direct DNA transformation or by pathogen-mediated transfection.

An insect system also can be used to express LTBP2. For example, in one such system *Autographa californica* nuclear polyhedrosis virus (AcNPV) is used as a vector to express foreign genes in *Spodoptera frugiperda* cells or in *Trichoplusia larvae*. Sequences encoding LTBP2 can be cloned into a non-essential region of the virus, such as the polyhedrin gene, and placed under control of the polyhedrin promoter. Successful insertion of LTBP2 will render the polyhedrin gene inactive and produce recombinant virus lacking coat protein. The recombinant viruses can then be used to infect *S. frugiperda* cells or *Trichoplusia larvae* in which LTBP2 can be expressed.

Mammalian Expression Systems

A number of viral-based expression systems can be used to express LTBP2 in mammalian host cells. For example, if an adenovirus is used as an expression vector, sequences encoding LTBP2 can be ligated into an adenovirus transcription/translation complex comprising the late promoter and tripartite leader sequence. Insertion in a non-essential E1 or E3 region of the viral genome can be used to obtain a viable virus which is capable of expressing LTBP2 in infected host cells [Engelhard, (1994)]. If desired, transcription enhancers, such as the Rous sarcoma virus (RSV) enhancer, can be used to increase expression in mammalian host cells.

Human artificial chromosomes (HACs) also can be used to deliver larger fragments of DNA than can be contained and expressed in a plasmid. HACs of 6M to 10M are constructed and delivered to cells via conventional delivery methods (e.g., liposomes, polycationic amino polymers, or vesicles). Specific initiation signals also can be used to achieve more efficient translation of sequences encoding LTBP2. Such signals include the ATG initiation codon and adjacent sequences. In cases where sequences encoding LTBP2, its initiation codon, and upstream sequences are inserted into the appropriate expression vector, no additional transcriptional or translational control signals may be needed. However, in cases where only coding sequence, or a fragment thereof, is inserted, exogenous translational control signals (including the ATG initiation codon) should be provided. The initiation codon should be in the correct reading frame to ensure translation of the entire insert. Exogenous translational elements and initiation codons can be of various origins, both natural and synthetic.

Host Cells

A host cell strain can be chosen for its ability to modulate the expression of the inserted sequences or to process the expressed LTBP2 in the desired fashion. Such modifications of the polypeptide include, but are not limited to, acetylation, carboxylation, glycosylation, phosphorylation, lipidation, and acylation. Post-translational processing which cleaves a "prepro" form of the polypeptide also can be used to facilitate correct insertion, folding and/or function. Different host cells which have specific cellular machinery and characteristic mechanisms for post-translational activities (e.g., CHO, HeLa, MDCK, HEK293, and WI38), are available from the American Type Culture Collection (ATCC; 10801 University Boulevard, Manassas, Va. 20110-2209) and can be chosen to ensure the correct modification and processing of the foreign protein.

Stable expression is preferred for long-term, high-yield production of recombinant proteins. For example, cell lines which stably express LTBP2 can be transformed using expression vectors which can contain viral origins of replication and/or endogenous expression elements and a selectable marker gene on the same or on a separate vector. Following the introduction of the vector, cells can be allowed to grow for 1-2 days in an enriched medium before they are switched to a selective medium. The purpose of the selectable marker is to confer resistance to selection, and its presence allows growth and recovery of cells which successfully express the introduced LTBP2 sequences. Resistant clones of stably transformed cells can be proliferated using tissue culture techniques appropriate to the cell type. Any number of selection systems can be used to recover transformed cell lines. These include, but are not limited to, the herpes simplex virus thymidine kinase [Logan, (1984)] and adenine phosphoribosyltransferase [Wigler, (1977)] genes which can be employed in tk⁻ or aprt⁻ cells, respectively. Also, antimetabolite, antibiotic, or herbicide resistance can be used as the basis for selection. For example, dhfr confers resistance to methotrexate [Lowy, (1980)], npt confers resistance to the aminoglycosides, neomycin and G-418 [Wigler, (1980)], and als and pat confer resistance to chlorsulfuron and phosphinotricin acetyltransferase, respectively [Colbere-Garapin, 1981]. Additional selectable genes have been described. For example, trpB allows cells to utilize indole in place of tryptophan, or hisD, which allows cells to utilize histinol in place of histidine. Visible markers such as anthocyanins, β-glucuronidase and its substrate GUS, and luciferase and its substrate luciferin, can be used to identify transformants and to quantify the amount of transient or stable protein expression attributable to a specific vector system Detecting Polypeptide Expression Although the presence of marker gene expression suggests that a LTBP2 polynucleotide is also present, its presence and expression may need to be confirmed. For example, if a sequence encoding LTBP2 is inserted within a marker gene sequence, transformed cells containing sequences which encode LTBP2 can be identified by the absence of marker gene function. Alternatively, a marker gene can be placed in tandem with a sequence encoding LTBP2 under the control of a single promoter. Expression of the marker gene in response to induction or selection usually indicates expression of LTBP2 polynucleotide.

Alternatively, host cells which contain a LTBP2 polynucleotide and which express LTBP2 can be identified by a variety of procedures known to those of skill in the art. These procedures include, but are not limited to, DNA-DNA or DNA-RNA hybridizations and protein bioassay or immunoassay techniques which include membrane, solution, or chip-based technologies for the detection and/or quantification of nucleic acid or protein. For example, the presence of a polynucleotide sequence encoding LTBP2 can be detected by DNA-DNA or DNA-RNA hybridization or amplification using probes or fragments or fragments of polynucleotides encoding LTBP2. Nucleic acid amplification-based assays involve the use of oligonucleotides selected from sequences encoding LTBP2 to detect transformants which contain a LTBP2 polynucleotide.

A variety of protocols for detecting and measuring the expression of LTBP2, using either polyclonal or monoclonal antibodies specific for the polypeptide, are known in the art. Examples include enzyme-linked immunosorbent assay (ELISA), radioimmunoassay (RIA), and fluorescence activated cell sorting (FACS). A two-site, monoclonal-based immunoassay using monoclonal antibodies reactive to two non-interfering epitopes on LTBP2 can be used, or a competitive binding assay can be employed.

A wide variety of labels and conjugation techniques are known by those skilled in the art and can be used in various nucleic acid and amino acid assays. Means for producing labeled hybridization or PCR probes for detecting sequences related to polynucleotides encoding LTBP2 include oligolabeling, nick translation, end-labeling, or PCR amplification using a labeled nucleotide. Alternatively, sequences encoding LTBP2 can be cloned into a vector for the production of an mRNA probe. Such vectors are known in the art, are commercially available, and can be used to synthesize RNA probes in vitro by addition of labeled nucleotides and an appropriate RNA polymerase such as T7, T3, or SP6. These procedures can be conducted using a variety of commercially available kits (Amersham Pharmacia Biotech, Promega, and US Biochemical). Suitable reporter molecules or labels which can be used for ease of detection include radionuclides, enzymes, and fluorescent, chemiluminescent, or chromogenic agents, as well as substrates, cofactors, inhibitors, magnetic particles, and the like.

Expression and Purification of Polypeptides

Host cells transformed with LTBP2 polynucleotides can be cultured under conditions suitable for the expression and recovery of the protein from cell culture. The polypeptide produced by a transformed cell can be secreted or contained intracellularly depending on the sequence and/or the vector used. As will be understood by those of skill in the art, expression vectors containing LTBP2 polynucleotides can be designed to contain signal sequences which direct secretion of soluble LTBP2 through a prokaryotic or eukaryotic cell membrane or which direct the membrane insertion of membrane-bound LTBP2.

As discussed above, other constructions can be used to join a sequence encoding LTBP2 to a nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). Inclusion of cleavable linker sequences such as those specific for Factor XA or enterokinase (Invitrogen, San Diego, Calif.) between the purification domain and LTBP2 also can be used to facilitate purification. One such expression vector provides for expression of a fusion protein containing LTBP2 and 6 histidine residues preceding a thioredoxin or an enterokinase cleavage site. The histidine residues facilitate purification by IMAC (immobilized metal ion affinity chromatography) Maddox, (1983)], while the enterokinase cleavage site provides a means for purifying LTBP2 from the fusion protein [Porath, (1992)].

Chemical Synthesis

Sequences encoding LTBP2 can be synthesized, in whole or in part, using chemical methods well known in the art. Alternatively, LTBP2 itself can be produced using chemical methods to synthesize its amino acid sequence, such as by direct peptide synthesis using solid-phase techniques. Protein synthesis can either be performed using manual techniques or by automation. Automated synthesis can be achieved, for example, using Applied Biosystems 431A Peptide Synthesizer (Perkin Elmer). Optionally, fragments of LTBP2 can be separately synthesized and combined using chemical methods to produce a full-length molecule.

The newly synthesized peptide can be substantially purified by preparative high performance liquid chromatography. The composition of a synthetic LTBP2 can be confirmed by amino acid analysis or sequencing. Additionally, any portion of the amino acid sequence of LTBP2 can be altered during direct synthesis and/or combined using chemical methods with sequences from other proteins to produce a variant polypeptide or a fusion protein.

Production of Altered Polypeptides

As will be understood by those of skill in the art, it may be advantageous to produce LTBP2 polynucleotides possessing non-naturally occurring codons. For example, codons preferred by a particular prokaryotic or eukaryotic host can be selected to increase the rate of protein expression or to produce an RNA transcript having desirable properties, such as a half-life which is longer than that of a transcript generated from the naturally occurring sequence.

The nucleotide sequences referred to herein can be engineered using methods generally known in the art to alter LTBP2 polynucleotides for a variety of reasons, including but not limited to, alterations which modify the cloning, processing, and/or expression of the polypeptide or mRNA product. DNA shuffling by random fragmentation and PCR reassembly of gene fragments and synthetic oligonucleotides can be used to engineer the nucleotide sequences. For example, site-directed mutagenesis can be used to insert new restriction sites, alter glycosylation patterns, change codon preference, produce splice variants, introduce mutations, and so forth.

LTBP2 Analogs

One general class of LTBP2 analogs are variants having an amino acid sequence that is a mutation of the amino acid sequence disclosed herein. Another general class of LTBP2 analogs is provided by anti-idiotype antibodies, and fragments thereof, as described below. Moreover, recombinant antibodies comprising anti-idiotype variable domains can be used as analogs (see, for example, [Monfardini et al., (1996)]). Since the variable domains of anti-idiotype LTBP2 antibodies mimic LTBP2, these domains can provide LTBP2 enzymatic activity. Methods of producing anti-idiotypic catalytic antibodies are known to those of skill in the art [Joron et al., (1992), Friboulet et al. (1994), Avalle et al., (1998)].

Another approach to identifying LTBP2 analogs is provided by the use of combinatorial libraries. Methods for constructing and screening phage display and other combinatorial libraries are provided, for example, by [Kay et al., Phage Display of Peptides and Proteins (Academic Press 1996), U.S. Pat. Nos. 5,783,384, 5,747,334, and 5,723,323.

Antibodies

Any type of antibody known in the art can be generated to bind specifically to an epitope of LTBP2.

"Antibody" as used herein includes intact immunoglobulin molecules, as well as fragments thereof, such as Fab, $F(ab')_2$, and Fv, which are capable of binding an epitope of LTBP2. Typically, at least 6, 8, 10, or 12 contiguous amino acids are required to form an epitope. However, epitopes which involve non-contiguous amino acids may require more, e.g., at least 15, 25, or 50 amino acid. An antibody which specifically binds to an epitope of LTBP2 can be used therapeutically, as well as in immunochemical assays, such as Western blots, ELISAs, radioimmunoassays, immunohistochemical assays, immunoprecipitations, or other immunochemical assays known in the art. Various immunoassays can be used to identify antibodies having the desired specificity. Numerous protocols for competitive binding or immunoradiometric assays are well known in the art. Such immunoassays typically involve the measurement of complex formation between an immunogen and an antibody which specifically binds to the LTBP2 immunogen.

Typically, an antibody which specifically binds to LTBP2 provides a detection signal at least 5-, 10-, or 20-fold higher than a detection signal provided with other proteins when used in an immunochemical assay. Preferably, antibodies which specifically bind to LTBP2 do not detect other proteins in immunochemical assays and can immunoprecipitate LTBP2 from solution.

LTBP2 can be used to immunize a mammal, such as a mouse, rat, rabbit, guinea pig, monkey, or human, to produce polyclonal antibodies. If desired, LTBP2 can be conjugated to a carrier protein, such as bovine serum albumin, thyroglobulin, and keyhole limpet hemocyanin. Depending on the host species, various adjuvants can be used to increase the immunological response. Such adjuvants include, but are not limited to, Freund's adjuvant, mineral gels (e.g., aluminum hydroxide), and surface active substances (e.g., lysolecithin, pluronic polyols, polyanions, peptides, oil emulsions, keyhole limpet hemocyanin, and dinitrophenol). Among adjuvants used in humans, BCG (*bacilli Calmette-Guerin*) and *Corynebacterium parvum* are especially useful.

Monoclonal antibodies which specifically bind to LTBP2 can be prepared using any technique which provides for the production of antibody molecules by continuous cell lines in culture. These techniques include, but are not limited to, the hybridoma technique, the human B-cell hybridoma technique, and the EBV-hybridoma technique [Roberge, (1995)].

In addition, techniques developed for the production of "chimeric antibodies", the splicing of mouse antibody genes to human antibody genes to obtain a molecule with appropriate antigen specificity and biological activity, can be used. Monoclonal and other antibodies also can be "humanized" to prevent a patient from mounting an immune response against the antibody when it is used therapeutically. Such antibodies may be sufficiently similar in sequence to human antibodies to be used directly in therapy or may require alteration of a few key residues. Sequence differences between rodent antibodies and human sequences can be minimized by replacing residues which differ from those in the human sequences by site directed mutagenesis of individual residues or by grating of entire complementarity determining regions. Antibodies which specifically bind to LTBP2 can contain antigen binding sites which are either partially or fully humanized, as disclosed in U.S. Pat. No. 5,565,332.

Alternatively, techniques described for the production of single chain antibodies can be adapted using methods known in the art to produce single chain antibodies which specifically bind to LTBP2. Antibodies with related specificity, but of distinct idiotypic composition, can be generated by chain shuffling from random combinatorial immunoglobin libraries. Single-chain antibodies also can be constructed using a DNA amplification method, such as PCR, using hybridoma cDNA as a template. Single-chain antibodies can be mono- or bispecific, and can be bivalent or tetravalent. Construction of tetravalent, bispecific single-chain antibodies is taught. A nucleotide sequence encoding a single-chain antibody can be constructed using manual or automated nucleotide synthesis, cloned into an expression construct using standard recombinant DNA methods, and introduced into a cell to express the coding sequence, as described below. Alternatively, single-chain antibodies can be produced directly using, for example, filamentous phage technology.

Antibodies which specifically bind to LTBP2 also can be produced by inducing in vivo production in the lymphocyte population or by screening immunoglobulin libraries or panels of highly specific binding reagents. Other types of antibodies can be constructed and used therapeutically in methods of the invention. For example, chimeric antibodies can be constructed as disclosed in WO 93/03151. Binding proteins which are derived from immunoglobulins and which are multivalent and multispecific, such as the "diabodies" described in WO 94/13804, also can be prepared.

Antibodies according to the invention can be purified by methods well known in the art. For example, antibodies can be affinity purified by passage over a column to which LTBP2 is bound. The bound antibodies can then be eluted from the column using a buffer with a high salt concentration.

Antisense Oligonucleotides

Antisense oligonucleotides are nucleotide sequences which are complementary to a specific DNA or RNA sequence. Once introduced into a cell, the complementary nucleotides combine with natural sequences produced by the cell to form complexes and block either transcription or translation. Preferably, an antisense oligonucleotide is at least 11 nucleotides in length, but can be at least 12, 15, 20, 25, 30, 35, 40, 45, or 50 or more nucleotides long. Longer sequences also can be used. Antisense oligonucleotide molecules can be provided in a DNA construct and introduced into a cell as described above to decrease the level of LTBP2 gene products in the cell.

Antisense oligonucleotides can be deoxyribonucleotides, ribonucleotides, or a combination of both. Oligonucleotides can be synthesized manually or by an automated synthesizer, by covalently linking the 5' end of one nucleotide with the 3' end of another nucleotide with non-phosphodiester internucleotide linkages such alkylphosphonates, phosphorothioates, phosphorodithioates, alkylphosphonothioates, alkylphosphonates, phosphoramidates, phosphate esters, carbamates, acetamidate, carboxymethyl esters, carbonates, and phosphate triesters.

Modifications of LTBP2 gene expression can be obtained by designing antisense oligonucleotides which will form duplexes to the control, 5', or regulatory regions of the LTBP2 gene. Oligonucleotides derived from the transcription initiation site, e.g., between positions −10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or chaperons. Therapeutic advances using triplex DNA have been described in the literature [Nicholls, (1993)]. An antisense oligonucleotide also can be designed to block translation of mRNA by preventing the transcript from binding to ribosomes.

Precise complementarity is not required for successful complex formation between an antisense oligonucleotide and the complementary sequence of a LTBP2 polynucleotide. Antisense oligonucleotides which comprise, for example, 2, 3, 4, or 5 or more stretches of contiguous nucleotides which are precisely complementary to a LTBP2 polynucleotide, each separated by a stretch of contiguous nucleotides which are not complementary to adjacent LTBP2 nucleotides, can provide sufficient targeting specificity for LTBP2 mRNA. Preferably, each stretch of complementary contiguous nucleotides is at least 4, 5, 6, 7, or 8 or more nucleotides in length. Non-complementary intervening sequences are preferably 1, 2, 3, or 4 nucleotides in length. One skilled in the art can easily use the calculated melting point of an antisense-sense pair to determine the degree of mismatching which will be tolerated between a particular antisense oligonucleotide and a particular LTBP2 polynucleotide sequence. Antisense oligonucleotides can be modified without affecting their ability to hybridize to a LTBP2 polynucleotide. These modifications can be internal or at one or both ends of the antisense molecule. For example, internucleoside phosphate linkages can be modified by adding cholesteryl or diamine moieties with varying numbers of carbon residues between the amino groups and terminal ribose. Modified bases and/or sugars, such as arabinose instead of ribose, or a 3',5'-substituted oligonucleotide in which the 3' hydroxyl group or the 5' phosphate group are substituted, also can be employed in a modified antisense oligonucleotide. These modified oligonucleotides can be prepared by methods well known in the art.

Ribozymes

Ribozymes are RNA molecules with catalytic activity [Uhlmann, (1987)]. Ribozymes can be used to inhibit gene function by cleaving an RNA sequence, as is known in the art. The mechanism of ribozyme action involves sequence-specific hybridization of the ribozyme molecule to complementary target RNA, followed by endonucleolytic cleavage. Examples include engineered hammerhead motif ribozyme molecules that can specifically and efficiently catalyze endonucleolytic cleavage of specific nucleotide sequences. The coding sequence of a LTBP2 polynucleotide can be used to generate ribozymes which will specifically bind to mRNA transcribed from a LTBP2 polynucleotide. Methods of designing and constructing ribozymes which can cleave other RNA molecules in trans in a highly sequence specific manner have been developed and described in the art. For example, the cleavage activity of ribozymes can be targeted to specific RNAs by engineering a discrete "hybridization" region into the ribozyme. The hybridization region contains a sequence complementary to the target RNA and thus specifically hybridizes with the target RNA.

Specific ribozyme cleavage sites within a LTBP2 RNA target can be identified by scanning the target molecule for ribozyme cleavage sites which include the following sequences: GUA, GUU, and GUC. Once identified, short RNA sequences of between 15 and 20 ribonucleotides corresponding to the region of the target RNA containing the cleavage site can be evaluated for secondary structural features which may render the target inoperable. Suitability of candidate LTBP2 RNA targets also can be evaluated by testing accessibility to hybridization with complementary oligonucleotides using ribonuclease protection assays. The nucleotide sequences shown in SEQ ID NO: 1 and its complement provide sources of suitable hybridization region sequences. Longer complementary sequences can be used to increase the affinity of the hybridization sequence for the target. The hybridizing and cleavage regions of the ribozyme can be integrally related such that upon hybridizing to the target RNA through the complementary regions, the catalytic region of the ribozyme can cleave the target.

Ribozymes can be introduced into cells as part of a DNA construct. Mechanical methods, such as microinjection, liposome-mediated transfection, electroporation, or calcium phosphate precipitation, can be used to introduce a ribozyme-containing DNA construct into cells in which it is desired to decrease LTBP2 expression. Alternatively, if it is desired that the cells stably retain the DNA construct, the construct can be supplied on a plasmid and maintained as a separate element or integrated into the genome of the cells, as is known in the art. A ribozyme-encoding DNA construct can include transcriptional regulatory elements, such as a promoter element, an enhancer or UAS element, and a transcriptional terminator signal, for controlling transcription of ribozymes in the cells (U.S. Pat. No. 5,641,673). Ribozymes also can be engineered to provide an additional level of regulation, so that destruction of mRNA occurs only when both a ribozyme and a target gene are induced in the cells.

LTBP2 Assay

LTBP2 protein expression in tissues, tissue homogenates and body fluids including plasma and serum can be measured by antibody-based strategies, e.g. by ELISA technology or Western Blotting/immunofluorescence. A polyclonal antibody generated against the full-length LTBP2 has been described in the literature.

Screening/Screening Assays

Regulators

Regulators as used herein, refer to compounds that affect the activity of LTBP2 in vivo and/or in vitro. Regulators can be agonists and antagonists of LTBP2 polypeptide and can be compounds that exert their effect on the LTBP2 activity via the enzymatic activity, expression, post-translational modifications or by other means. Agonists of LTBP2 are molecules which, when bound to LTBP2, increase or prolong the activity of LTBP2. Agonists of LTBP2 include proteins, nucleic acids, carbohydrates, small molecules, or any other molecule which activate LTBP2. Antagonists of LTBP2 are molecules which, when bound to LTBP2, decrease the amount or the duration of the activity of LTBP2. Antagonists include proteins, nucleic acids, carbohydrates, antibodies, small molecules, or any other molecule which decrease the activity of LTBP2.

The term "modulate", as it appears herein, refers to a change in the activity of LTBP2 polypeptide. For example, modulation may cause an increase or a decrease in enzymatic activity, binding characteristics, or any other biological, functional, or immunological properties of LTBP2.

As used herein, the terms "specific binding" or "specifically binding" refer to that interaction between a protein or peptide and an agonist, an antibody, or an antagonist. The interaction is dependent upon the presence of a particular structure of the protein recognized by the binding molecule (i.e., the antigenic determinant or epitope). For example, if an antibody is specific for epitope "A" the presence of a polypeptide containing the epitope A, or the presence of free unlabeled A, in a reaction containing free labeled A and the antibody will reduce the amount of labeled A that binds to the antibody.

The invention provides methods (also referred to herein as "screening assays") for identifying compounds which can be used for the treatment of diseases related to LTBP2. The methods entail the identification of candidate or test compounds or agents (e.g., peptides, peptidomimetics, small molecules or other molecules) which bind to LTBP2 and/or have a stimulatory or inhibitory effect on the biological activity of LTBP2 or its expression and then determining which of these compounds have an effect on symptoms or diseases related to LTBP2 in an in vivo assay.

Candidate or test compounds or agents which bind to LTBP2 and/or have a stimulatory or inhibitory effect on the activity or the expression of LTBP2 are identified either in assays that employ cells which express LTBP2 (cell-based assays) or in assays with isolated LTBP2 (cell-free assays). The various assays can employ a variety of variants of LTBP2 (e.g., full-length LTBP2, a biologically active fragment of LTBP2, or a fusion protein which includes all or a portion of LTBP2). Moreover, LTBP2 can be derived from any suitable mammalian species (e.g., human LTBP2, rat LTBP2 or murine LTBP2). The assay can be a binding assay entailing direct or indirect measurement of the binding of a test compound or a known LTBP2 ligand to LTBP2. The assay can also be an activity assay entailing direct or indirect measurement of the activity of LTBP2. The assay can also be an expression assay entailing direct or indirect measurement of the expression of LTBP2 mRNA or LTBP2 protein. The various screening assays are combined with an in vivo assay entailing measuring the effect of the test compound on the symptoms of diseases related to LTBP2.

The present invention includes biochemical, cell free assays that allow the identification of inhibitors and agonists of proteins suitable as lead structures for pharmacological drug development. Such assays involve contacting a form of LTBP2 (e.g., full-length LTBP2, a biologically active fragment of LTBP2, or a fusion protein comprising all or a portion of LTBP2) with a test compound and determining the ability of the test compound to act as an antagonist (preferably) or an agonist of the enzymatic activity of LTBP2.

Solution in vitro assays can be used to identify a LTBP2 substrate or inhibitor. Solid phase systems can also be used to identify a substrate or inhibitor of a LTBP2 polypeptide. For example, a LTBP2 polypeptide or LTBP2 fusion protein can be immobilized onto the surface of a receptor chip of a commercially available biosensor instrument (BIACORE, Biacore AB; Uppsala, Sweden). The use of this instrument is disclosed, for example, by [Karlsson, (1991), and Cunningham and Wells, (1993)].

In brief, a LTBP2 polypeptide or fusion protein is covalently attached, using amine or sulfhydryl chemistry, to dextran fibers that are attached to gold film within a flow cell. A test sample is then passed through the cell. If a LTBP2 substrate or inhibitor is present in the sample, it will bind to the immobilized polypeptide or fusion protein, causing a change in the refractive index of the medium, which is detected as a change in surface plasmon resonance of the gold film. This system allows the determination on- and off-rates, from which binding affinity can be calculated, and assessment of the stoichiometry of binding, as well as the kinetic effects of LTBP2 mutation. This system can also be used to examine antibody-antigen interactions, and the interactions of other complement/anti-complement pairs.

In one embodiment, the invention provides assays for screening candidate or test compounds which bind to or modulate the activity of LTBP2. Such assays can employ full-length LTBP2, a biologically active fragment of LTBP2, or a fusion protein which includes all or a portion of LTBP2. As described in greater detail below, the test compound can be obtained by any suitable means, e.g., from conventional compound libraries.

Determining the ability of the test compound to modulate the activity of LTBP2 can be accomplished, for example, by determining the ability of LTBP2 to bind to or interact with a target molecule. The target molecule can be a molecule with which LTBP2 binds or interacts with in nature. The target molecule can be a component of a signal transduction pathway which facilitates transduction of an extracellular signal. The target LTBP2 molecule can be, for example, a second intracellular protein which has catalytic activity or a protein which facilitates the association of downstream signaling molecules with LTBP2.

Determining the ability of LTBP2 to bind to or interact with a target molecule can be accomplished by one of the methods described above for determining direct binding. In one embodiment, determining the ability of a polypeptide of the invention to bind to or interact with a target molecule can be accomplished by determining the activity of the target molecule. For example, the activity of the target molecule can be determined by detecting induction of a cellular second messenger of the target (e.g., intracellular $Ca^{2+}$, diacylglycerol, $IP_3$, etc.), detecting catalytic/enzymatic activity of the target on an appropriate substrate, detecting the induction of a reporter gene (e.g., a regulatory element that is responsive to a polypeptide of the invention operably linked to a nucleic acid encoding a detectable marker, e.g., luciferase), or detecting a cellular response.

In various embodiments of the above assay methods of the present invention, it may be desirable to immobilize LTBP2 (or a LTBP2 target molecule) to facilitate separation of complexed from uncomplexed forms of one or both of the proteins, as well as to accommodate automation of the assay. Binding of a test compound to LTBP2, or interaction of LTBP2 with a target molecule in the presence and absence of a candidate compound, can be accomplished in any vessel suitable for containing the reactants. Examples of such vessels include microtitre plates, test tubes, and microcentrifuge tubes. In one embodiment, a fusion protein can be provided which adds a domain that allows one or both of the proteins to be bound to a matrix. For example, glutathione-S-transferase (GST) fusion proteins or glutathione-S-transferase fusion proteins can be adsorbed onto glutathione sepharose beads (Sigma Chemical; St. Louis, Mo.) or glutathione derivatized microtitre plates, which are then combined with the test compound or the test compound and either the non-adsorbed target protein or LTBP2, and the mixture incubated under conditions conducive to complex formation (e.g., at physiological conditions for salt and pH). Following incubation, the beads or microtitre plate wells are washed to remove any unbound components and complex formation is measured either directly or indirectly, for example, as described above. Alternatively, the complexes can be dissociated from the matrix, and the level of binding or activity of LTBP2 can be determined using standard techniques.

Other techniques for immobilizing proteins on matrices can also be used in the screening assays of the invention. For example, either LTBP2 or its target molecule can be immobilized utilizing conjugation of biotin and streptavidin. Biotinylated polypeptide of the invention or target molecules can be prepared from biotin-NHS (N-hydroxy-succinimide) using techniques well known in the art (e.g., biotinylation kit, Pierce Chemicals; Rockford, Ill.), and immobilized in the wells of streptavidin-coated plates (Pierce Chemical). Alternatively, antibodies reactive with LTBP2 or target molecules but which do not interfere with binding of the polypeptide of the invention to its target molecule can be derivatized to the wells of the plate, and unbound target or polypeptide of the invention trapped in the wells by antibody conjugation. Methods for detecting such complexes, in addition to those described above for the GST-immobilized complexes, include immunodetection of complexes using antibodies reactive with LTBP2 or target molecule, as well as enzyme-linked assays which rely on detecting an enzymatic activity associated with LTBP2 or target molecule.

Another technique for drug screening which may be used provides for high throughput screening of compounds having suitable binding affinity to the protein of interest as described in published PCT application WO84/03564. In this method, large numbers of different small test compounds are synthesized on a solid substrate, such as plastic pins or some other surface. The test compounds are reacted with LTBP2, or fragments thereof, and washed. Bound LTBP2 is then detected by methods well known in the art. Purified LTBP2 can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding LTBP2 specifically compete with a test compound for binding LTBP2. In this manner, antibodies can be used to detect the presence of any peptide which shares one or more antigenic determinants with LTBP2.

The screening assay can also involve monitoring the expression of LTBP2. For example, regulators of expression of LTBP2 can be identified in a method in which a cell is contacted with a candidate compound and the expression of LTBP2 protein or mRNA in the cell is determined. The level of expression of LTBP2 protein or mRNA the presence of the candidate compound is compared to the level of expression of LTBP2 protein or mRNA in the absence of the candidate compound. The candidate compound can then be identified as a regulator of expression of LTBP2 based on this comparison. For example, when expression of LTBP2 protein or mRNA protein is greater (statistically significantly greater) in the presence of the candidate compound than in its absence, the candidate compound is identified as a stimulator of LTBP2 protein or mRNA expression. Alternatively, when expression of LTBP2 protein or mRNA is less (statistically significantly less) in the presence of the candidate compound than in its absence, the candidate compound is identified as an inhibitor of LTBP2 protein or mRNA expression. The level of LTBP2 protein or mRNA expression in the cells can be determined by methods described below.

Binding Assays

For binding assays, the test compound is preferably a small molecule which binds to and occupies the active site of LTBP2 polypeptide, thereby making the ligand binding site inaccessible to substrate such that normal biological activity is prevented. Examples of such small molecules include, but are not limited to, small peptides or peptide-like molecules. Potential ligands which bind to a polypeptide of the invention include, but are not limited to, the natural ligands of known LTBP2 proteins and analogues or derivatives thereof.

In binding assays, either the test compound or the LTBP2 polypeptide can comprise a detectable label, such as a fluorescent, radioisotopic, chemiluminescent, or enzymatic label, such as horseradish peroxidase, alkaline phosphatase, or luciferase. Detection of a test compound which is bound to LTBP2 polypeptide can then be accomplished, for example, by direct counting of radioemission, by scintillation counting, or by determining conversion of an appropriate substrate to a detectable product. Alternatively, binding of a test compound to a LTBP2 polypeptide can be determined without labeling either of the interactants. For example, a microphysiometer can be used to detect binding of a test compound with a LTBP2 polypeptide. A microphysiometer (e.g., Cytosensor™) is an analytical instrument that measures the rate at which a cell acidifies its environment using a light-addressable potentiometric sensor (LAPS). Changes in this acidification rate can be used as an indicator of the interaction between a test compound and LTBP2 [Haseloff, (1988)].

Determining the ability of a test compound to bind to LTBP2 also can be accomplished using a technology such as real-time Bimolecular Interaction Analysis (BIA) [McConnell, (1992); Sjolander, (1991)]. BIA is a technology for studying biospecific interactions in real time, without labeling any of the interactants (e.g., BIAcore™). Changes in the optical phenomenon surface plasmon resonance (SPR) can be used as an indication of real-time reactions between biological molecules.

In yet another aspect of the invention, a LTBP2-like polypeptide can be used as a "bait protein" in a two-hybrid assay or three-hybrid assay [Szabo, (1995); U.S. Pat. No. 5,283,317), to identify other proteins which bind to or interact with LTBP2 and modulate its activity.

The two-hybrid system is based on the modular nature of most transcription factors, which consist of separable DNA-binding and activation domains. Briefly, the assay utilizes two different DNA constructs. For example, in one construct, polynucleotide encoding LTBP2 can be fused to a polynucleotide encoding the DNA binding domain of a known transcription factor (e.g., GAL-4). In the other construct a DNA sequence that encodes an unidentified protein ("prey" or "sample") can be fused to a polynucleotide that codes for the activation domain of the known transcription factor. If the "bait" and the "prey" proteins are able to interact in vivo to form an protein-dependent complex, the DNA-binding and activation domains of the transcription factor are brought into close proximity. This proximity allows transcription of a reporter gene (e.g., LacZ), which is operably linked to a transcriptional regulatory site responsive to the transcription factor. Expression of the reporter gene can be detected, and cell colonies containing the functional transcription factor can be isolated and used to obtain the DNA sequence encoding the protein which interacts with LTBP2.

It may be desirable to immobilize either the LTBP2 (or polynucleotide) or the test compound to facilitate separation of the bound form from unbound forms of one or both of the interactants, as well as to accommodate automation of the assay. Thus, either the LTBP2-like polypeptide (or polynucleotide) or the test compound can be bound to a solid support. Suitable solid supports include, but are not limited to, glass or plastic slides, tissue culture plates, microtiter wells, tubes, silicon chips, or particles such as beads (including, but not limited to, latex, polystyrene, or glass beads). Any method known in the art can be used to attach LTBP2-like polypeptide (or polynucleotide) or test compound to a solid support, including use of covalent and non-covalent linkages, passive absorption, or pairs of binding moieties attached respectively to the polypeptide (or polynucleotide) or test compound and the solid support. Test compounds are preferably bound to the solid support in an array, so that the location of individual test compounds can be tracked. Binding of a test compound to LTBP2 (or a polynucleotide encoding for LTBP2) can be accomplished in any vessel suitable for containing the reactants. Examples of such vessels include microtiter plates, test tubes, and microcentrifuge tubes.

In one embodiment, LTBP2 is a fusion protein comprising a domain that allows binding of LTBP2 to a solid support. For example, glutathione-S-transferase fusion proteins can be adsorbed onto glutathione sepharose beads (Sigma Chemical, St. Louis, Mo.) or glutathione derivatized microtiter plates, which are then combined with the test compound or the test compound and the non-adsorbed LTBP2; the mixture is then incubated under conditions conducive to complex formation (e.g., at physiological conditions for salt and pH). Following incubation, the beads or microtiter plate wells are washed to remove any unbound components. Binding of the interactants can be determined either directly or indirectly, as described above. Alternatively, the complexes can be dissociated from the solid support before binding is determined.

Other techniques for immobilizing proteins or polynucleotides on a solid support also can be used in the screening assays of the invention. For example, either LTBP2 (or a polynucleotide encoding LTBP2) or a test compound can be immobilized utilizing conjugation of biotin and streptavidin. Biotinylated LTBP2 (or a polynucleotide encoding biotinylated LTBP2) or test compounds can be prepared from biotin-NHS (N-hydroxysuccinimide) using techniques well known in the art (e.g., biotinylation kit, Pierce Chemicals, Rockford, Ill.) and immobilized in the wells of streptavidin-coated plates (Pierce Chemical). Alternatively, antibodies which specifically bind to LTBP2, polynucleotide, or a test compound, but which do not interfere with a desired binding site, such as the active site of LTBP2, can be derivatized to the wells of the plate. Unbound target or protein can be trapped in the wells by antibody conjugation.

Methods for detecting such complexes, in addition to those described above for the GST-immobilized complexes, include immunodetection of complexes using antibodies which specifically bind to LTBP2 polypeptide or test compound, enzyme-linked assays which rely on detecting an activity of LTBP2 polypeptide, and SDS gel electrophoresis under non-reducing conditions.

Screening for test compounds which bind to a LTBP2 polypeptide or polynucleotide also can be carried out in an intact cell. Any cell which comprises a LTBP2 polypeptide or polynucleotide can be used in a cell-based assay system. A LTBP2 polynucleotide can be naturally occurring in the cell or can be introduced using techniques such as those described above. Binding of the test compound to LTBP2 or a polynucleotide encoding LTBP2 is determined as described above.

Functional Assays

Test compounds can be tested for the ability to increase or decrease LTBP2 activity of a LTBP2 polypeptide. The LTBP2 activity can be measured, for example, using methods described in the specific examples, below. LTBP2 activity can be measured after contacting either a purified LTBP2 or an intact cell with a test compound. A test compound which decreases LTBP2 activity by at least about 10, preferably about 50, more preferably about 75, 90, or 100% is identified as a potential agent for decreasing LTBP2 activity. A test compound which increases LTBP2 activity by at least about 10, preferably about 50, more preferably about 75, 90, or 100% is identified as a potential agent for increasing LTBP2 activity.

Gene Expression

In another embodiment, test compounds which increase or decrease LTBP2 gene expression are identified. As used herein, the term "correlates with expression of a polynucleotide" indicates that the detection of the presence of nucleic acids, the same or related to a nucleic acid sequence encoding LTBP2, by northern analysis or realtime PCR is indicative of the presence of nucleic acids encoding LTBP2 in a sample, and thereby correlates with expression of the transcript from the polynucleotide encoding LTBP2. The term "microarray", as used herein, refers to an array of distinct polynucleotides or oligonucleotides arrayed on a substrate, such as paper, nylon or any other type of membrane, filter, chip, glass slide, or any other suitable solid support. A LTBP2 polynucleotide is contacted with a test compound, and the expression of an RNA or polypeptide product of LTBP2 polynucleotide is determined. The level of expression of appropriate mRNA or polypeptide in the presence of the test compound is compared to the level of expression of mRNA or polypeptide in the absence of the test compound. The test compound can then be identified as a regulator of expression based on this comparison. For example, when expression of mRNA or polypeptide is greater in the presence of the test compound than in its absence, the test compound is identified as a stimulator or enhancer of the mRNA or polypeptide expression. Alternatively, when expression of the mRNA or polypeptide is less in the presence of the test compound than in its absence, the test compound is identified as an inhibitor of the mRNA or polypeptide expression.

The level of LTBP2 mRNA or polypeptide expression in the cells can be determined by methods well known in the art for detecting mRNA or polypeptide. Either qualitative or quantitative methods can be used. The presence of polypeptide products of LTBP2 polynucleotide can be determined, for example, using a variety of techniques known in the art, including immunochemical methods such as radioimmunoassay, Western blotting, and immunohistochemistry. Alternatively, polypeptide synthesis can be determined in vivo, in a cell culture, or in an in vitro translation system by detecting incorporation of labelled amino acids into LTBP2.

Such screening can be carried out either in a cell-free assay system or in an intact cell. Any cell which expresses LTBP2 polynucleotide can be used in a cell-based assay system. The LTBP2 polynucleotide can be naturally occurring in the cell or can be introduced using techniques such as those described above. Either a primary culture or an established cell line can be used.

Test Compounds

Suitable test compounds for use in the screening assays of the invention can be obtained from any suitable source, e.g., conventional compound libraries. The test compounds can also be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds [Lam, (1997)]. Examples of methods for the synthesis of molecular libraries can be found in the art.

Libraries of compounds may be presented in solution or on beads, bacteria, spores, plasmids or phage.

Modeling of Regulators

Computer modeling and searching technologies permit identification of compounds, or the improvement of already identified compounds, that can modulate LTBP2 expression or activity. Having identified such a compound or composition, the active sites or regions are identified. Such sites might typically be the enzymatic active site, regulator binding sites, or ligand binding sites. The active site can be identified using methods known in the art including, for example, from the amino acid sequences of peptides, from the nucleotide sequences of nucleic acids, or from study of complexes of the relevant compound or composition with its natural ligand. In the latter case, chemical or X-ray crystallographic methods can be used to find the active site by finding where on the factor the complexed ligand is found.

Next, the three dimensional geometric structure of the active site is determined. This can be done by known methods, including X-ray crystallography, which can determine a complete molecular structure. On the other hand, solid or liquid phase NMR can be used to determine certain intramolecular distances. Any other experimental method of structure determination can be used to obtain partial or complete geometric structures. The geometric structures may be measured with a complexed ligand, natural or artificial, which may increase the accuracy of the active site structure determined.

If an incomplete or insufficiently accurate structure is determined, the methods of computer based numerical modeling can be used to complete the structure or improve its accuracy. Any recognized modeling method may be used, including parameterized models specific to particular biopolymers such as proteins or nucleic acids, molecular dynamics models based on computing molecular motions, statistical mechanics models based on thermal ensembles, or combined models. For most types of models, standard molecular force fields, representing the forces between constituent atoms and groups, are necessary, and can be selected from force fields known in physical chemistry. The incomplete or less accurate experimental structures can serve as constraints on the complete and more accurate structures computed by these modeling methods.

Finally, having determined the structure of the active site, either experimentally, by modeling, or by a combination, candidate modulating compounds can be identified by searching databases containing compounds along with information on their molecular structure. Such a search seeks compounds having structures that match the determined active site structure and that interact with the groups defining the active site. Such a search can be manual, but is preferably computer assisted. These compounds found from this search are potential LTBP2 modulating compounds.

Alternatively, these methods can be used to identify improved modulating compounds from an already known modulating compound or ligand. The composition of the known compound can be modified and the structural effects of modification can be determined using the experimental and computer modeling methods described above applied to the new composition. The altered structure is then compared to the active site structure of the compound to determine if an improved fit or interaction results. In this manner systematic variations in composition, such as by varying side groups, can be quickly evaluated to obtain modified modulating compounds or ligands of improved specificity or activity.

Therapeutic Indications and Methods

It was found by the present applicant that LTBP2 is expressed in various human tissues.

Cardiovascular Disorders

The human LTBP2 is highly expressed in the following cardiovascular related tissues: heart, heart myocardial infarction, heart atrium (right), heart ventricle (left), Purkinje fibers, aorta, aorta valve, coronary artery, coronary artery, pulmonary artery, carotid artery, vein, pulmonic valve, (caval) vein, coronary artery endothel cells, aortic smooth muscle cells, pulmonary artery smooth muscle cells, aortic endothel cells, HUVEC cells, pulmonary artery endothel cells, iliac artery endothel cells, adrenal gland, liver tumor, adipose, adipose, kidney, kidney tumor. Expression in the above mentioned tissues demonstrates that the human LTBP2 or mRNA can be utilized to diagnose of cardiovascular diseases. Additionally the activity of the human LTBP2 can be modulated to treat cardiovascular diseases.

The human LTBP2 is highly expressed in adipose tissues. Expression in adipose demonstrates that the human LTBP2 or mRNA can be utilized to diagnose of dyslipidemia diseases as an cardiovascular disorder. Additionally the activity of the human LTBP2 can be modulated to treat but not limited to dyslipidemia diseases.

The human LTBP2 is highly expressed in liver tissues: liver tumor. Expression in liver tissues demonstrates that the human LTBP2 or mRNA can be utilized to diagnose of dyslipidemia disorders as an cardiovascular disorder. Additionally the activity of the human LTBP2 can be modulated to treat but not limited to dyslipidemia disorders.

The human LTBP2 is highly expressed in kidney tissues: kidney, kidney, kidney tumor. Expression in kidney tissues demonstrates that the human LTBP2 or mRNA can be utilized to diagnose of blood pressure disorders as an cardiovascular disorder. Additionally the activity of the human LTBP2 can be modulated to treat but not limited to blood pressure disorders as hypertension or hypotension.

The human LTBP2 is highly expressed in adrenal gland. Expression in adrenal gland tissues demonstrates that the human LTBP2 or mRNA can be utilized to diagnose of blood pressure disorders as an cardiovascular disorder. Additionally the activity of the human LTBP2 can be modulated to treat but not limited to blood pressure disorders as hypertension or hypotension.

Heart failure is defined as a pathophysiological state in which an abnormality of cardiac function is responsible for the failure of the heart to pump blood at a rate commensurate with the requirement of the metabolizing tissue. It includes all forms of pumping failures such as high output and low output, acute and chronic, right sided or left sided, systolic or diastolic, independent of the underlying cause.

Myocardial infarction (MI) is generally caused by an abrupt decrease in coronary blood flow that follows a thrombotic occlusion of a coronary artery previously narrowed by arteriosclerosis. MI prophylaxis (primary and secondary prevention) is included as well as the acute treatment of MI and the prevention of complications.

Ischemic diseases are conditions in which the coronary flow is restricted resulting in a perfusion which is inadequate to meet the myocardial requirement for oxygen. This group of diseases includes stable angina, unstable angina and asymptomatic ischemia.

Arrhythmias include all forms of atrial and ventricular tachyarrhythmias, atrial tachycardia, atrial flutter, atrial fibrillation, atrio ventricular reentrant tachycardia, preexitation syndrome, ventricular tachycardia, ventricular flutter, ventricular fibrillation, as well as bradycardic forms of arrhythmias.

Hypertensive vascular diseases include primary as well as all kinds of secondary arterial hypertension, renal, endocrine, neurogenic, others. The genes may be used as drug targets for the treatment of hypertension as well as for the prevention of all complications arising from cardiovascular diseases.

Peripheral vascular diseases are defined as vascular diseases in which arterial and/or venous flow is reduced resulting in an imbalance between blood supply and tissue oxygen demand. It includes chronic peripheral arterial occlusive disease (PAOD), acute arterial thrombosis and embolism, inflammatory vascular disorders, Raynaud's phenomenon and venous disorders.

Atherosclerosis is a cardiovascular disease in which the vessel wall is remodeled, compromising the lumen of the vessel. The atherosclerotic remodeling process involves accumulation of cells, both smooth muscle cells and monocyte/macrophage inflammatory cells, in the intima of the vessel wall. These cells take up lipid, likely from the circulation, to form a mature atherosclerotic lesion. Although the formation of these lesions is a chronic process, occurring over decades of an adult human life, the majority of the morbidity associated with atherosclerosis occurs when a lesion ruptures, releasing thrombogenic debris that rapidly occludes the artery. When such an acute event occurs in the coronary artery, myocardial infarction can ensue, and in the worst case, can result in death.

The formation of the atherosclerotic lesion can be considered to occur in five overlapping stages such as migration, lipid accumulation, recruitment of inflammatory cells, proliferation of vascular smooth muscle cells, and extracellular matrix deposition. Each of these processes can be shown to occur in man and in animal models of atherosclerosis, but the relative contribution of each to the pathology and clinical significance of the lesion is unclear.

Thus, a need exists for therapeutic methods and agents to treat cardiovascular pathologies, such as atherosclerosis and other conditions related to coronary artery disease.

Cardiovascular diseases include but are not limited to disorders of the heart and the vascular system like congestive heart failure, myocardial infarction, ischemic diseases of the heart, all kinds of atrial and ventricular arrhythmias, hypertensive vascular diseases, peripheral vascular diseases, and atherosclerosis.

To high or to low levels of fats in the bloodstream, especially cholesterol, can cause long term problems. The risk to develop atherosclerosis and coronary artery or carotid artery disease (and thus the risk of having a heart attack or stroke) increases with the total cholesterol level increasing. Nevertheless, extremely low cholesterol levels may not be healthy. Examples of disorders of lipid metabolism are hyperlipidemia (abnormally high levels of fats (cholesterol, triglycerides, or both) in the blood, may be caused by family history of hyperlipidemia, obesity, a high fat diet, lack of exercise, moderate to high alcohol consumption, cigarette smoking, poorly controlled diabetes, and an underactive thyroid gland), hereditary hyperlipidemias (type I hyperlipoproteinemia (familial hyperchylomicronemia), type II hyperlipoproteinemia (familial hypercholesterolemia), type III hyperlipoproteinemia, type IV hyperlipoproteinemia, or type V hyperlipoproteinemia), hypolipoproteinemia, lipidoses (caused by abnormalities in the enzymes that metabolize fats), Gaucher's disease, Niemann Pick disease, Fabry's disease, Wolman's disease, cerebrotendinous xanthomatosis, sitosterolemia, Refsum's disease, or Tay Sachs disease.

Kidney disorders may lead to hyper or hypotension. Examples for kidney problems possibly leading to hypertension are renal artery stenosis, pyelonephritis, glomerulonephritis, kidney tumors, polycystic kidney disease, injury to the kidney, or radiation therapy affecting the kidney. Excessive urination may lead to hypotension.

Hematological Disorders

The human LTBP2 is highly expressed in the following tissues of the hematological system: bone marrow stromal cells, thrombocytes and leukocytes. The expression in the above mentioned tissues demonstrates that the human LTBP2 or mRNA can be utilized to diagnose of hematological diseases. Additionally the activity of the human LTBP2 can be modulated to treat hematological disorders.

Hematological disorders comprise diseases of the blood and all its constituents as well as diseases of organs involved in the generation or degradation of the blood. They include but are not limited to 1) Anemias, 2) Myeloproliferative Disorders, 3) Hemorrhagic Disorders, 4) Leukopenia, 5) Eosinophilic Disorders, 6) Leukemias, 7) Lymphomas, 8) Plasma Cell Dyscrasias, 9) Disorders of the Spleen in the course of hematological disorders, Disorders according to 1) include, but are not limited to anemias due to defective or deficient hem synthesis, deficient erythropoiesis. Disorders according to 2) include, but are not limited to polycythemia vera, tumor associated erythrocytosis, myelofibrosis, thrombocythemia. Disorders according to 3) include, but are not limited to vasculitis, thrombocytopenia, heparin induced thrombocytopenia, thrombotic thrombocytopenic purpura, hemolytic uremic syndrome, hereditary and acquired disorders of platelet function, hereditary coagulation disorders. Disorders according to 4) include, but are not limited to neutropenia, lymphocytopenia. Disorders according to 5) include, but are not limited to hypereosinophilia, idiopathic hypereosinophilic syndrome. Disorders according to 6) include, but are not limited to acute myeloic leukemia, acute lymphoblastic leukemia, chronic myelocytic leukemia, chronic lymphocytic leukemia, myelodysplastic syndrome. Disorders according to 7) include, but are not limited to Hodgkin's disease, non Hodgkin's lymphoma, Burkitt's lymphoma, mycosis fungoides cutaneous T cell lymphoma. Disorders according to 8) include, but are not limited to multiple myeloma, macroglobulinemia, heavy chain diseases. In extension of the preceding idiopathic thrombocytopenic purpura, iron deficiency anemia, megaloblastic anemia (vitamin B12 deficiency), aplastic anemia, thalassemia, malignant lymphoma bone marrow invasion, malignant lymphoma skin invasion, haemolytic uraemic syndrome, giant platelet disease are considered to be hematological diseases too.

Cancer Disorders

The human LTBP2 is highly expressed in the following cancer tissues: HUVEC cells, thyroid tumor, colon tumor, ileum tumor, rectum tumor, liver tumor, lung tumor, uterus tumor, ovary tumor, breast tumor, kidney tumor. The expression in the above mentioned tissues and in particular the differential expression between diseased tissue thyroid tumor and healthy tissue thyroid, between diseased tissue lung tumor and healthy tissue lung demonstrates that the human LTBP2 or mRNA can be utilized to diagnose of cancer. Additionally the activity of the human LTBP2 can be modulated to treat cancer.

Cancer disorders within the scope of the invention comprise any disease of an organ or tissue in mammals characterized by poorly controlled or uncontrolled multiplication of normal or abnormal cells in that tissue and its effect on the body as a whole. Cancer diseases within the scope of the invention comprise benign neoplasms, dysplasias, hyperplasias as well as neoplasms showing metastatic growth or any other transformations like e.g. leukoplakias which often precede a breakout of cancer. Cells and tissues are cancerous when they grow more rapidly than normal cells, displacing or spreading into the surrounding healthy tissue or any other tissues of the body described as metastatic growth, assume abnormal shapes and sizes, show changes in their nucleocytoplasmatic ratio, nuclear polychromasia, and finally may cease. Cancerous cells and tissues may affect the body as a whole when causing paraneoplastic syndromes or if cancer occurs within a vital organ or tissue, normal function will be impaired or halted, with possible fatal results. The ultimate involvement of a vital organ by cancer, either primary or metastatic, may lead to the death of the mammal affected. Cancer tends to spread, and the extent of its spread is usually related to an individual's chances of surviving the disease. Cancers are generally said to be in one of three stages of growth: early, or localized, when a tumor is still confined to the tissue of origin, or primary site; direct extension, where cancer cells from the tumour have invaded adjacent tissue or have spread only to regional lymph nodes; or metastasis, in which cancer cells have migrated to distant parts of the body from the primary site, via the blood or lymph systems, and have established secondary sites of infection. Cancer is said to be malignant because of its tendency to cause death if not treated. Benign tumors usually do not cause death, although they may if they interfere with a normal body function by virtue of their location, size, or paraneoplastic side effects. Hence benign tumors fall under the definition of cancer within the scope of the invention as well. In general, cancer cells divide at a higher rate than do normal cells, but the distinction between the growth of cancerous and normal tissues is not so much the rapidity of cell division in the former as it is the partial or complete loss of growth restraint in cancer cells and their failure to differentiate into a useful, limited tissue of the type that characterizes the functional equilibrium of growth of normal tissue. Cancer tissues may express certain molecular receptors and probably are influenced by the host's susceptibility and immunity and it is known that certain cancers of the breast and prostate, for example, are considered dependent on specific hormones for their existence. The term "cancer" under the scope of the invention is not limited to simple benign neoplasia but comprises any other benign and malign neoplasia like 1) Carcinoma, 2) Sarcoma, 3) Carcinosarcoma, 4) Cancers of the blood forming tissues, 5) tumors of nerve tissues including the brain, 6) cancer of skin cells. Cancer according to 1) occurs in epithelial tissues, which cover the outer body (the skin) and line mucous membranes and the inner cavitary structures of organs e.g. such as the breast, lung, the respiratory and gastrointestinal tracts, the endocrine glands, and the genitourinary system. Ductal or glandular elements may persist in epithelial tumors, as in adenocarcinomas like e.g. thyroid adenocarcinoma, gastric adenocarcinoma, uterine adenocarcinoma. Cancers of the pavement cell epithelium of the skin and of certain mucous membranes, such as e.g. cancers of the tongue, lip, larynx, urinary bladder, uterine cervix, or penis, may be termed epidermoid or squamous cell carcinomas of the respective tissues and are in the scope of the definition of cancer as well. Cancer according to 2) develops in connective tissues, including fibrous tissues, adipose (fat) tissues, muscle, blood vessels, bone, and cartilage like e.g. osteogenic sarcoma; liposarcoma, fibrosarcoma, synovial sarcoma. Cancer according to 3) is cancer that develops in both epithelial and connective tissue. Cancer disease within the scope of this definition may be primary or secondary, whereby primary indicates that the cancer originated in the tissue where it is found rather than was established as a secondary site through metastasis from another lesion. Cancers and tumor diseases within the scope of this definition may be benign or malign and may affect all anatomical structures of the body of a mammal. By example but not limited to they comprise cancers and tumor diseases of I) the bone marrow and bone marrow derived cells (leukemias), II) the endocrine and exocrine glands like e.g. thyroid, parathyroid, pituitary, adrenal glands, salivary glands, pancreas III) the breast, like e.g. benign or malignant tumors in the mammary glands of either a male or a female, the mammary ducts, adenocarcinoma, medullary carcinoma, comedo carcinoma, Paget's disease of the nipple, inflammatory carcinoma of the young woman, IV) the lung, V) the stomach, VI) the liver and spleen, VII) the small intestine, VIII) the colon, IX) the bone and its supportive and connective tissues like malignant or benign bone tumour, e.g. malignant osteogenic sarcoma, benign osteoma, cartilage tumors; like malignant chondrosarcoma or benign chondroma; bone marrow tumors like malignant myeloma or benign eosinophilic granuloma, as well as metastatic tumors from bone tissues at other locations of the body; X) the mouth, throat, larynx, and the esophagus, XI) the urinary bladder and the internal and external organs and structures of the urogenital system of male and female like ovaries, uterus, cervix of the uterus, testes, and prostate gland, XII) the prostate, XII) the pancreas, like ductal carcinoma of the pancreas; XIV) the lymphatic tissue like lymphomas and other tumors of lymphoid origin, XV) the skin, XVI) cancers and tumor diseases of all anatomical structures belonging to the respiration and respiratory systems including thoracal muscles and linings, XVII) primary or secondary cancer of the lymph nodes XVIII) the tongue and of the bony structures of the hard palate or sinuses, XVIV) the mouth, cheeks, neck and salivary glands, XX) the blood vessels including the heart and their linings, XXI) the smooth or skeletal muscles and their ligaments and linings, XXII) the peripheral, the autonomous, the central nervous system including the cerebellum, XXIII) the adipose tissue.

Endocrine System and Hormone Disorders

The human LTBP2 is highly expressed in the following tissues of the endocrinological system: adrenal gland, thyroid, thyroid tumor, pancreas. The expression in the above mentioned tissues demonstrates that the human LTBP2 or mRNA can be utilized to diagnose of endocrinological disorders. Additionally the activity of the human LTBP2 can be modulated to treat endocrinological disorders.

The endocrine system consists of a group of organs whose main function is to produce and secrete hormones directly into the bloodstream. The major organs of the endocrine system are the hypothalamus, the pituitary gland, thyroid gland, the parathyroid glands, the islets of the pancreas, the adrenal glands, the testes, and the ovaries.

The hypothalamus secretes several hormones that stimulate the pituitary: Some trigger the release of pituitary hormones; others suppress the release of pituitary hormones.

The pituitary gland coordinates many functions of the other endocrine glands, but some pituitary hormones have direct effects.

The insulin secreting cells of the pancreas respond to glucose and fatty acids. Parathyroid cells respond to calcium and phosphate. The adrenal medulla (part of the adrenal gland) responds to direct stimulation by the parasympathetic nervous system.

When endocrine glands malfunction, hormone in the blood can become abnormally high or low, disrupting body functions. Many disorders are caused by malfunction of the endocrine system or hormones. Examples of such disorders are presented in the following.

Diabetes mellitus is a disorder in which blood levels of glucose are abnormally high because the body doesn't release or use insulin adequately.

People with type I diabetes mellitus (insulin dependent diabetes) produce little or no insulin at all. In type I diabetes more than 90 percent of the insulin producing cells (beta cells) of the pancreas are permanently destroyed. The resulting insulin deficiency is severe, and to survive, a person with type I diabetes must regularly inject insulin.

In type II diabetes mellitus (non insulin dependent diabetes) the body develops resistance to insulin effects, resulting in a relative insulin deficiency.

The pancreas has two major functions: to secrete fluid containing digestive enzymes into the duodenum and to secrete the hormones insulin and glucagon. Chronic pancreatitis is a long standing inflammation of the pancreas. Eventually, the insulin secreting cells of the pancreas may be destroyed, gradually leading to diabetes. An insulinoma is a rare type of pancreatic tumor that secretes insulin. The symptoms of an insulinoma result from low blood glucose levels. A gastrinoma is a pancreatic tumor that produces excessive levels of the hormone gastrin, which stimulates the stomach to secrete acid and enzymes, causing peptic ulcers. The excess gastrin secreted by the gastrinoma causes symptoms, called the Zollinger Ellison syndrome. A glucagonoma is a tumor that produces the hormone glucagon, which raises the level of glucose in the blood and produces a distinctive rash.

Diabetes insipidus is a disorder in which insufficient levels of antidiuretic hormone cause excessive thirst (polydipsia) and excessive production of very dilute urine (polyuria). Diabetes insipidus results from the decreased production of antidiuretic hormone (vasopressin).

The body has two adrenal glands. The medulla of the adrenal glands secretes hormones such as adrenaline (epinephrine) that affect blood pressure, heart rate, sweating, and other activities also regulated by the sympathetic nervous system. The cortex secretes many different hormones, including corticosteroids (cortisone like hormones), androgens (male hormones), and mineralocorticoids, which control blood pressure and the levels of salt and potassium in the body.

A diseases characterized by underactive adrenal glands is Addison's disease (adrenocortical insufficiency).

Several disorders are characterized by overactive Adrenal Glands. The causes can be changes in the adrenal glands themselves or overstimulation by the pituitary gland. Examples of these diseases are listed in the following.

Overproduction of androgenic steroids (testosterone and similar hormones, leads to virilization), overproduction of corticosteroids (causes could be tumors of the pituitary or the adrenal gland, results in Cushing's syndrome), Nelson's syndrome (developed by people who have both adrenal glands removed, characterized by an enlargement of the pituitary gland), Overproduction of aldosterone (hyperaldosteronism), Conn's syndrome (hyperaldosterism caused by a tumor), pheochromocytoma (a tumor that originating from the adrenal gland's chromaffin cells, causing overproduction of catecholamines), The thyroid is a small gland located under the Adam's apple. It secretes thyroid hormones, which control the metabolic rate. The thyroid gland traps iodine and processes it into thyroid hormones. The euthyroid sick syndrome is characterized by lack of conversion of the T4 form of thyroid hormone to the T3 form. Hyperthyroidism (overactive thyroid gland, production of too much hormone) may have several causes. Thyroiditis (an inflammation of the thyroid gland), typically leads to a phase of hyperthyroidism. The inflammation may damage the thyroid gland, so that in later stages the disease is characterized by transient or permanent underactivity (hypothyroidism). Toxic thyroid nodules (adenomas) often produce thyroid hormone in large quantities. Toxic multinodular goiter (Plummer's disease) is a disorder in which there are many nodules. Graves' disease (toxic diffuse goiter) is believed to be caused by an antibody that stimulates the thyroid to produce too much thyroid hormone. In toxic nodular goiter, one or more nodules in the thyroid produce too much thyroid hormone and aren't under the control of thyroid stimulating hormone. Secondary hyperthyroidism may (rarely) be caused by a pituitary tumor that secretes too much thyroid stimulating hormone, by resistance of the pituitary to thyroid hormone, which results in the pituitary gland secreting too much thyroid stimulating hormone, or by a hydatidiform mole in women. Thyroid storm is a sudden extreme overactivity of the thyroid gland is a life threatening emergency requiring prompt treatment.

Hypothyroidism is a condition in which the thyroid gland is underactive and produces too little thyroid hormone. Very severe hypothyroidism is called myxedema. In Hashimoto's thyroiditis (autoimmune thyroiditis) the thyroid gland is often enlarged, and hypothyroidism results because the gland's functioning areas are gradually destroyed. Rarer causes of hypothyroidism include some inherited disorders which are caused by abnormalities of the enzymes in thyroid cells. In other rare disorders, either the hypothalamus or the pituitary gland fails to secrete enough of the hormone needed to stimulate normal thyroid function.

Other examples of Thyroiditis are silent lymphocytic thyroiditis, Hashimoto's thyroiditis, or subacute granulomatous thyroiditis.

Thyroid cancer is any one of four main types of malignancy of the thyroid: papillary, follicular, anaplastic, or medullary.

The pituitary is a pea sized gland that sits in a bony structure (sella turcica) at the base of the brain. The sella turcica protects the pituitary but allows very little room for expansion. If the pituitary enlarges, it tends to push upward, often pressing on the areas of the brain that carry signals from the eyes, possibly resulting in headaches or impaired vision. The pituitary gland has two distinct parts: the anterior (front) and the posterior (back) lobes. The anterior lobe produces (secretes) hormones that ultimately control the function of the thyroid gland, adrenal glands, and reproductive organs (ovaries and testes); milk production (lactation) in the breasts; and overall body growth. It also produces hormones that cause the skin to darken and that inhibit pain sensations. The posterior lobe produces hormones that regulate water balance, stimulate the let down of milk from the breasts in lactating women, and stimulate contractions of the uterus.

Examples for disorders of the pituitary gland are Empty Sella Syndrome; hypopituitarism (an underactive pituitary gland); acromegaly, which is excessive growth caused by oversecretion of growth hormone, which is almost always caused by a benign pituitary tumor (adenoma); galactorrhea, which is the production of breast milk in men or in women who aren't breastfeeding, in both sexes, the most common cause of galactorrhea is a prolactin producing tumor (prolactinoma) in the pituitary gland.

Neurological Disorders

The human LTBP2 is highly expressed in the following brain tissues: dorsal root ganglia, dorsal root ganglia, cerebellum, occipital lobe and spinal cord. The expression in brain tissues demonstrates that the human LTBP2 or mRNA can be utilized to diagnose nervous system diseases. Additionally the activity of the human LTBP2 can be modulated to treat nervous system diseases.

CNS disorders include disorders of the central nervous system as well as disorders of the peripheral nervous system. CNS disorders include, but are not limited to brain injuries, cerebrovascular diseases and their consequences, Parkinson's disease, corticobasal degeneration, motor neuron disease, dementia, including ALS, multiple sclerosis, traumatic brain injury, stroke, post stroke, post traumatic brain injury, and small vessel cerebrovascular disease. Dementias, such as Alzheimer's disease, vascular dementia, dementia with Lewy bodies, frontotemporal dementia and Parkinsonism linked to chromosome 17, frontotemporal dementias, including Pick's disease, progressive nuclear palsy, corticobasal degeneration, Huntington's disease, thalamic degeneration, Creutzfeld Jakob dementia, HIV dementia, schizophrenia with dementia, and Korsakoff's psychosis, within the meaning of the invention are also considered to be CNS disorders.

Similarly, cognitive related disorders, such as mild cognitive impairment, age associated memory impairment, age related cognitive decline, vascular cognitive impairment, attention deficit disorders, attention deficit hyperactivity disorders, and memory disturbances in children with learning disabilities are also considered to be CNS disorders.

Pain, within the meaning of the invention, is also considered to be a CNS disorder. Pain can be associated with CNS disorders, such as multiple sclerosis, spinal cord injury, sciatica, failed back surgery syndrome, traumatic brain injury, epilepsy, Parkinson's disease, post stroke, and vascular lesions in the brain and spinal cord (e.g., infarct, hemorrhage, vascular malformation). Non central neuropathic pain includes that associated with post mastectomy pain, phantom feeling, reflex sympathetic dystrophy (RSD), trigeminal neuralgiaradioculopathy, post surgical pain, HIV/AIDS related pain, cancer pain, metabolic neuropathies (e.g., diabetic neuropathy, vasculitic neuropathy secondary to connective tissue disease), paraneoplastic polyneuropathy associated, for example, with carcinoma of lung, or leukemia, or lymphoma, or carcinoma of prostate, colon or stomach, trigeminal neuralgia, cranial neuralgias, and post herpetic neuralgia. Pain associated with peripheral nerve damage, central pain (i.e. due to cerebral ischemia) and various chronic pain i.e., lumbago, back pain (low back pain), inflammatory and/or rheumatic pain. Headache pain (for example, migraine with aura, migraine without aura, and other migraine disorders), episodic and chronic tension type headache, tension type like headache, cluster headache, and chronic paroxysmal hemicrania are also CNS disorders. Visceral pain such as pancreatitis, intestinal cystitis, dysmenorrhea, irritable Bowel syndrome, Crohn's disease, biliary colic, ureteral colic, myocardial infarction and pain syndromes of the pelvic cavity, e.g., vulvodynia, orchialgia, urethral syndrome and protatodynia are also CNS disorders. Also considered to be a disorder of the nervous system are acute pain, for example postoperative pain, and pain after trauma.

Urological Disorders

The human LTBP2 is highly expressed in the following urological tissues: dorsal root ganglia, prostata, bladder, kidney, kidney tumor. The expression in the above mentioned tissues demonstrates that the human LTBP2 or mRNA can be utilized to diagnose of urological disorders. Additionally the activity of the human LTBP2 can be modulated to treat urological disorders.

The human LTBP2 is highly expressed in dorsal root ganglia tissue. Expression in dorsal root ganglia demonstrates that the human LTBP2 or mRNA can be utilized to diagnose of incontinence as an urological disorder. The dorsal root ganglia are involved in the neuronal regulation of the urological system. Additionally the activity of the human LTBP2 can be modulated to treat but not limited to incontinence.

Genitourological disorders comprise benign and malign disorders of the organs constituting the genitourological system of female and male, renal diseases like acute or chronic renal failure, immunologically mediated renal diseases like renal transplant rejection, lupus nephritis, immune complex renal diseases, glomerulopathies, nephritis, toxic nephropathy, obstructive uropathies like benign prostatic hyperplasia (BPH), neurogenic bladder syndrome, urinary incontinence like urge, stress, or overflow incontinence, pelvic pain, and erectile dysfunction.

Applications

The present invention provides LTBP2 for prophylactic, therapeutic and diagnostic methods for cardiovascular diseases, hematological diseases, neurological diseases, cancer, endocrinological diseases and urological diseases.

The regulatory method of the invention involves contacting a cell with an agent that modulates one or more of the activities of LTBP2. An agent that modulates activity can be an agent as described herein, such as a nucleic acid or a protein, a naturally-occurring cognate ligand of the polypeptide, a peptide, a peptidomimetic, or any small molecule. In one embodiment, the agent stimulates one or more of the biological activities of LTBP2. Examples of such stimulatory agents include the active LTBP2 and nucleic acid molecules encoding a portion of LTBP2. In another embodiment, the agent inhibits one or more of the biological activities of LTBP2. Examples of such inhibitory agents include antisense nucleic acid molecules and antibodies. These regulatory methods can be performed in vitro (e.g., by culturing the cell with the agent) or, alternatively, in vivo (e.g, by administering the agent to a subject). As such, the present invention provides methods of treating an individual afflicted with a disease or disorder characterized by unwanted expression or activity of LTBP2 or a protein in the LTBP2 signaling pathway. In one embodiment, the method involves administering an agent like any agent identified or being identifiable by a screening assay as described herein, or combination of such agents that modulate say upregulate or downregulate the expression or activity of LTBP2 or of any protein in the LTBP2 signaling pathway. In another embodiment, the method involves administering a regulator of LTBP2 as therapy to compensate for reduced or undesirably low expression or activity of LTBP2 or a protein in the LTBP2 signaling pathway.

Stimulation of activity or expression of LTBP2 is desirable in situations in which enzymatic activity or expression is abnormally low and in which increased activity is likely to have a beneficial effect. Conversely, inhibition of enzymatic activity or expression of LTBP2 is desirable in situations in which activity or expression of LTBP2 is abnormally high and in which decreasing its activity is likely to have a beneficial effect.

The present invention provides for the use of LTBP2 or fragments of LTBP2 as a biomarker for cardiovascular diseases, hematological diseases, neurological diseases, cancer, endocrinological diseases and urological diseases.

This invention is further illustrated by the following examples which should not be construed as limiting. The contents of all references, patents and published patent applications cited throughout this application are hereby incorporated by reference.

Pharmaceutical Compositions

This invention further pertains to novel agents identified by the above-described screening assays and uses thereof for treatments as described herein.

The nucleic acid molecules, polypeptides, and antibodies (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The invention includes pharmaceutical compositions comprising a regulator of LTBP2 expression or activity (and/or a regulator of the activity or expression of a protein in the LTBP2 signaling pathway) as well as methods for preparing such compositions by combining one or more such regulators and a pharmaceutically acceptable carrier. Also within the invention are pharmaceutical compositions comprising a regulator identified using the screening assays of the invention packaged with instructions for use. For regulators that are antagonists of LTBP2 activity or which reduce LTBP2 expression, the instructions would specify use of the pharmaceutical composition for treatment of cardiovascular diseases, hematological diseases, neurological diseases, cancer, endocrinological diseases and urological diseases. For regulators that are agonists of LTBP2 activity or increase LTBP2 expression, the instructions would specify use of the pharmaceutical composition for treatment of cardiovascular diseases, hematological diseases, neurological diseases, cancer, endocrinological diseases and urological diseases.

An inhibitor of LTBP2 may be produced using methods which are generally known in the art. In particular, purified LTBP2 may be used to produce antibodies or to screen libraries of pharmaceutical agents to identify those which specifically bind LTBP2. Antibodies to LTBP2 may also be generated using methods that are well known in the art. Such antibodies may include, but are not limited to, polyclonal, monoclonal, chimeric, single chain antibodies, Fab fragments, and fragments produced by a Fab expression library. Neutralizing antibodies like those which inhibit dimer formation are especially preferred for therapeutic use.

In another embodiment of the invention, the polynucleotides encoding LTBP2, or any fragment or complement thereof, may be used for therapeutic purposes. In one aspect, the complement of the polynucleotide encoding LTBP2 may be used in situations in which it would be desirable to block the transcription of the mRNA. In particular, cells may be transformed with sequences complementary to polynucleotides encoding LTBP2. Thus, complementary molecules or fragments may be used to modulate LTBP2 activity, or to achieve regulation of gene function. Such technology is now well known in the art, and sense or antisense oligonucleotides or larger fragments can be designed from various locations along the coding or control regions of sequences encoding LTBP2.

Expression vectors derived from retroviruses, adenoviruses, or herpes or vaccinia viruses, or from various bacterial plasmids, may be used for delivery of nucleotide sequences to the targeted organ, tissue, or cell population. Methods which are well known to those skilled in the art can be used to construct vectors which will express nucleic acid sequence complementary to the polynucleotides of the gene encoding LTBP2. These techniques are described, for example, in [Scott and Smith (1990)].

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical composition containing LTBP2 in conjunction with a pharmaceutically acceptable carrier, for any of the therapeutic effects discussed above. Such pharmaceutical compositions may consist of LTBP2, antibodies to LTBP2, and mimetics, agonists, antagonists, or inhibitors of LTBP2. The compositions may be administered alone or in combination with at least one other agent, such as a stabilizing compound, which may be administered in any sterile, biocompatible pharmaceutical carrier including, but not limited to, saline, buffered saline, dextrose, and water. The compositions may be administered to a patient alone, or in combination with other agents, drugs or hormones.

A pharmaceutical composition of the invention is formulated to be compatible with its intended route of administration. Examples of routes of administration include parenteral, e.g. intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EM™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, a pharmaceutically acceptable polyol like glycerol, propylene glycol, liquid polyetheylene glycol, and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin. Sterile injectable solutions can be prepared by incorporating the active compound (e.g., a polypeptide or antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed.

Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from a pressurized container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration. For pharmaceutical compositions which include an antagonist of LTBP2 activity, a compound which reduces expression of LTBP2, or a compound which reduces expression or activity of a protein in the LTBP2 signaling pathway or any combination thereof, the instructions for administration will specify use of the composition for cardiovascular diseases, hematological diseases, neurological diseases, cancer, endocrinological diseases and urological diseases. For pharmaceutical compositions which include an agonist of LTBP2 activity, a compound which increases expression of LTBP2, or a compound which increases expression or activity of a protein in the LTBP2 signaling pathway or any combination thereof, the instructions for administration will specify use of the composition for cardiovascular diseases, hematological diseases, neurological diseases, cancer, endocrinological diseases and urological diseases.

Diagnostics

One embodiment of the invention describes LTBP2 as a biomarker for diagnostic use.

Use of LTBP2 as a biomarker in diagnostics is based by the comparison of LTBP2 level in a biological sample from a diseased mammal with the LTBP2 level in a control sample from a healthy or normal mammal. Does the LTBP2 level in the diseased mammal differs from the LTBP2 level in a normal or healthy mammal then the diseased mammal is diagnosed with a disease associated with an altered LTBP2 level. Furthermore, comparing LTBP2 levels of a biological sample from a diseased mammal with LTBP2 levels of control samples from mammals with a LTBP2-associated disease already diagnosed with different stages or severity of said disease, allows the diagnose of a LTBP2-associated disease of said first diseased mammal and specifying the severity of the LTBP2-associated disease. The biological sample is taken from the analogue tissue or body fluid than the control sample.

Normal or standard values for LTBP2 expression are established by using control samples from healthy or diseased mammalian subjects. A control sample can be obtained by collecting separate or combined body fluids or cell extracts taken from normal mammalian subjects, preferably human, achieving statistical relevant numbers. To obtain the normal or standard LTBP2 level of the control samples, the samples were subjected to suitable detection methods to detect LTBP2 polypeptide, polynucleotide or activity. The determination of LTBP2 level in a mammal subjected to diagnosis is performed analogously by collecting a biological sample from said mammal. Quantities of LTBP2 levels in biological samples from a mammal subjected to diagnosis are compared with the standard or normal values measured from a control sample. Deviation between standard value (determined from control sample) and subject value (determined from biological sample) establishes the parameters for diagnosing disease. Absolute quantification of LTBP2 levels measured from biological or control samples may be achieved by comparing those values with values obtained from an experiment in which a known amount of a substantially purified polypeptide is used.

Antibodies which specifically bind LTBP2 may be used for the diagnosis of disorders characterized by the expression of the biomarker LTBP2, or in diagnostic assays to monitor patients being treated achieving guidance for therapy for such a disease. Such a treatment includes medication suitable to treat such a disease, and treatment with LTBP2 polypeptides or polynucleotides, or agonists, antagonists, and inhibitors of LTBP2. Antibodies useful for diagnostic purposes may be prepared in the same manner as those described above for therapeutics. Diagnostic assays for LTBP2 include methods which utilize the antibody and a label to detect LTBP2 in human body fluids or in extracts of cells or tissues. The antibodies may be used with or without modification, and may be labeled by covalent or non-covalent joining with a reporter molecule. A wide variety of reporter molecules, several of which are described above, are known in the art and may be used.

A variety of protocols for measuring LTBP2, including ELISAs, RIAs, Planar Waveguide technology, and FACS, are known in the art and provide a basis for diagnosing altered or abnormal levels of LTBP2 expression. Planar Waveguide Technology bioassays are designed to perform multiplexed nucleic acid hybridization assays, immunoaffinity reactions and membrane receptor based assays with high sensitivity and selectivity. The recognition elements specific for the analytes of interest are bound onto the surface in small discrete spots; the transfer of the recognition elements onto the surface is performed using an adequate spotting technology, which requires only minute amounts of recognition elements. Such an arrangement of different recognition elements in an array format allows the simultaneous detection and quantification of hundreds to thousands of different analytes per sample including replicates.

Reactions on microarrays usually follow a typical scheme:

Recognition elements (e.g. oligonucleotides, cDNAs, or antibodies) are spotted onto the chemically modified planar waveguide surface with typical spot diameters of 100-200 µm. The remaining free binding sites on the surface subsequently are being blocked to reduce or eliminate nonspecific binding. In a next step the sample (e.g. fluorescently labeled cDNA or pre-incubated analyte/fluorescently labeled antibody complex) is transferred onto the surface for incubation. The incubation time where a selective recognition and binding between recognition elements and corresponding target molecules (e.g. DNA—DNA hybridization or antigen—antibody interaction) occurs depends on the affinity between the analytes and the immobilized recognition elements. The resulting fluorescing spots can then be detected during readout.

Due to the laterally resolved imaging of the fluorescence signals of the individual spots by a CCD-camera, a large variety of different analytes can be quantified simultaneously, requiring typically sample volumes in the range of 15 µl. Calibration and referencing spots allow for accurate quantification of analytes using just one chip and enable the establishment of dose response and time dependent activity profiles [Pawlak (2002), Duveneck (2002)].

Normal or standard values for LTBP2 expression are established by using control samples from healthy or diseased mammalian subjects. A control sample can be obtained by collecting separate or combined body fluids or cell extracts taken from normal mammalian subjects, preferably human, achieving statistical relevant numbers. To obtain normal or standard values the control samples are combined with an antibody to LTBP2 under conditions suitable for complex formation. The amount of standard complex formation may be quantified by various methods, preferably by photometric means. The determination of LTBP2 level in a mammal subjected to diagnosis is performed analogously by collecting a biological sample from said mammal, combining said sample with an antibody to LTBP2 and determination of complex formation. Quantities of LTBP2 expressed in biological samples from a mammal subjected to diagnosis are compared with the standard or normal values measured from a control sample. Deviation between standard value (determined from control sample) and subject value (determined from biological sample) establishes the parameters for diagnosing disease. Absolute quantification of LTBP2 levels measured from biological or control samples may be achieved by comparing those values with values obtained from an experiment in which a known amount of a substantially purified polypeptide is used.

In another embodiment of the invention, the polynucleotides encoding LTBP2 may be used for diagnostic purposes. The polynucleotides which may be used include oligonucleotide sequences, complementary RNA and DNA molecules, and PNAs. The polynucleotides may be used to detect and quantified gene expression in control and biological samples in which expression of the biomarker LTBP2 may be correlated with disease. The diagnostic assay may be used to distinguish between absence, presence, and excess expression of LTBP2, and to monitor regulation of LTBP2 levels during therapeutic intervention.

Polynucleotide sequences encoding LTBP2 may be used for the diagnosis of cardiovascular diseases, hematological diseases, neurological diseases, cancer, endocrinological diseases and urological diseases associated with expression of LTBP2. The polynucleotide sequences encoding LTBP2 may be used in Southern, Northern, or dot-blot analysis, or other membrane-based technologies; in PCR technologies; in dipstick, pin, and ELISA assays; bDNA (branched DNA technology) and Planar Waveguide Technology; and in microarrays utilizing a biological sample from diseased mammals to detect altered LTBP2 expression. Such qualitative or quantitative methods are well known in the art.

In a particular aspect, the nucleotide sequences encoding LTBP2 may be useful in assays that detect the presence of associated disorders, particularly those mentioned above. The nucleotide sequences encoding LTBP2 may be labeled by standard methods and added to a biological sample from diseased mammals under conditions suitable for the formation of hybridization complexes. After a suitable incubation period, the sample is washed and the signal is quantified and compared with a standard value. If the amount of signal in the patient sample is altered from that of a comparable control sample, the nucleotide sequences have hybridized with nucleotide sequences in the sample, and the presence of altered levels of nucleotide sequences encoding LTBP2 in the sample indicates the presence of the associated disorder. Such assays may also be used to evaluate the efficacy of a particular therapeutic treatment regimen in animal studies, in clinical trials, or in monitoring the treatment of an individual patient.

In order to provide a basis for the diagnosis of cardiovascular diseases, hematological diseases, neurological diseases, cancer, endocrinological diseases and urological diseases associated with expression of LTBP2, a normal or standard profile for expression is established. This may be accomplished by combining body fluids or cell extracts taken from normal subjects, either animal or human, with a sequence, or a fragment thereof, encoding LTBP2, under conditions suitable for hybridization or amplification. Quantification of LTBP2 levels measured from biological or control samples may be achieved by comparing those values with values obtained from an experiment in which a known amount of a substantially purified polynucleotide is used. Standard values obtained from normal samples may be compared with values obtained from samples from patients who are symptomatic for a disorder. Deviation from standard values is used to establish the presence of a disorder.

Biomarker

Use of LTBP2 as a Biomarker

One of ordinary skill in the art knows several methods and devices for the detection and analysis of the markers of the instant invention. With regard to polypeptides or proteins in patient test samples, immunoassay devices and methods are often used. These devices and methods can utilize labelled molecules in various sandwich, competitive, or non-competitive assay formats, to generate a signal that is related to the presence or amount of an analyte of interest. Additionally, certain methods and devices, such as biosensors and optical immunoassays, may be employed to determine the presence or amount of analytes without the need for a labelled molecule.

Preferably the markers are analyzed using an immunoassay, although other methods are well known to those skilled in the art (for example, the measurement of marker RNA levels). The presence or amount of a marker is generally determined using antibodies specific for each marker and detecting specific binding. Any suitable immunoassay may be utilized, for example, enzyme-linked immunoassays (ELISA), radioimmunoassay (RIAs), competitive binding assays, planar waveguide technology, and the like. Specific immunological binding of the antibody to the marker can be detected directly or indirectly. Direct labels include fluorescent or luminescent tags, metals, dyes, radionuclides, and the like, attached to the antibody. Indirect labels include various enzymes well known in the art, such as alkaline phosphatase, horseradish peroxidase and the like. For an example of how this procedure is carried out on a machine, one can use the RAMP Biomedical device, called the Clinical Reader Sup™, which uses the fluorescent tag method, though the skilled artisan will know of many different machines and manual protocols to perform the same assay. Diluted whole blood is applied to the sample well. The red blood cells are retained in the sample pad, and the separated plasma migrates along the strip. Fluorescent dyed latex particles bind to the analyte and are immobilized at the detection zone. Additional particles are immobilized at the internal control zone. The fluorescence of the detection and internal control zones are measured on the RAMP Clinical Reader Sup™, and the ratio between these values is calculated. This ratio is used to determine the analyte concentration by interpolation from a lot-specific standard curve supplied by the manufacturer in each test kit for each assay.

The use of immobilized antibodies specific for the markers is also contemplated by the present invention and is well known by one of ordinary skill in the art. The antibodies could be immobilized onto a variety of solid supports, such as magnetic or chromatographic matrix particles, the surface of an assay place (such as microtiter wells), pieces of a solid substrate material (such as plastic, nylon, paper), and the like. An assay strip could be prepared by coating the antibody or a plurality of antibodies in an array on solid support. This strip could then be dipped into the test sample and then processed quickly through washes and detection steps to generate a measurable signal, such as a coloured spot.

The analysis of a plurality of markers may be carried out separately or simultaneously with one test sample. Several markers may be combined into one test for efficient processing of a multiple of samples. In addition, one skilled in the art would recognize the value of testing multiple samples (for example, at successive time points) from the same individual. Such testing of serial samples will allow the identification of changes in marker levels over time. Increases or decreases in marker levels, as well as the absence of change in marker levels, would provide useful information about the disease status that includes, but is not limited to identifying the approximate time from onset of the event, the presence and amount of salvagable tissue, the appropriateness of drug therapies, the effectiveness of various therapies, identification of the severity of the event, identification of the disease severity, and identification of the patient's outcome, including risk of future events.

An assay consisting of a combination of the markers referenced in the instant invention may be constructed to provide relevant information related to differential diagnosis. Such a panel may be constructed using 1, 2, 3, 4, 5, 6, 7, 8, 9, 10, 15, 20, or more or individual markers. The analysis of a single marker or subsets of markers comprising a larger panel of markers could be carried out methods described within the instant invention to optimize clinical sensitivity or specificity in various clinical settings.

The analysis of markers could be carried out in a variety of physical formats as well. For example, the use of microtiter plates or automation could be used to facilitate the processing of large numbers of test samples. Alternatively, single sample formats could be developed to facilitate immediate treatment and diagnosis in a timely fashion, for example, in ambulatory transport or emergency room settings. Particularly useful physical formats comprise surfaces having a plurality of discrete, addressable locations for the detection of a plurality of different analytes. Such formats include protein microarrays, or "protein chips" and capillary devices.

Cardiac markers serve an important role in the early detection and monitoring of cardiovascular disease. Markers of disease are typically substances found in a bodily sample that can be easily measured. The measured amount can correlate to underlying disease pathophysiology, presence or absence of a current or imminent cardiac event, probability of a cardiac event in the future. In patients receiving treatment for their condition the measured amount will also correlate with responsiveness to therapy. Markers can include elevated levels of blood pressure, cholesterol, blood sugar, homocysteine and C-reactive protein (CRP). However, current markers, even in combination with other measurements or risk factors, do not adequately identify patients at risk, accurately detect events (i.e., heart attacks), or correlate with therapy. For example, half of patients do not have elevated serum cholesterol or other traditional risk factors.

Use of markers in diagnosis of cardiac conditions is described in, for example, Alpert et al. (2000); Newby et al. (2001); de Lemos et al. (2002); Boersma et al. (2002); Christenson et al. (2001), each of which is incorporated by reference in its entirety.

Cardiovascular Biomarker

BNP (as an Example for Cardiovascular Biomarkers)

B-type natriuretic peptide (BNP), also called brain-type natriuretic peptide is a 32 amino acid, 4 kDa peptide that is involved in the natriuresis system to regulate blood pressure and fluid balance. The precursor to BNP is synthesized as a 108-amino acid molecule, referred to as "pre pro BNP," that is proteolytically processed into a 76-amino acid N-terminal peptide (amino acids 1-76), referred to as "NT pro BNP" and the 32-amino acid mature hormone, referred to as BNP or BNP 32 (amino acids 77-108). It has been suggested that each of these species—NT pro-BNP, BNP-32, and the pre pro BNP—can circulate in human plasma. The 2 forms, pre pro BNP and NT pro BNP, and peptides which are derived from BNP, pre pro BNP and NT pro BNP and which are present in the blood as a result of proteolyses of BNP, NT pro BNP and pre pro BNP, are collectively described as markers related to or associated with BNP. Proteolytic degradation of BNP and of peptides related to BNP have also been described in the literature and these proteolytic fragments are also encompassed it the term "BNP related peptides". BNP and BNP-related peptides are predominantly found in the secretory granules of the cardiac ventricles, and are released from the heart in response to both ventricular volume expansion and pressure overload. Elevations of BNP are associated with raised atrial and pulmonary wedge pressures, reduced ventricular systolic and diastolic function, left ventricular hypertrophy, and myocardial infarction [Sagnella, (1998)]. Furthermore, there are numerous reports of elevated BNP concentration associated with congestive heart failure and renal failure. While BNP and BNP-related peptides are likely not specific for ACS, they may be sensitive markers of ACS because they may indicate not only cellular damage due to ischemia, but also a perturbation of the natriuretic system associated with ACS. The term "BNP" as used herein refers to the mature 32-amino acid BNP molecule itself. As the skilled artisan will recognize, however, other markers related to BNP may also serve as diagnostic or prognostic indicators in patients with ACS. For example, BNP is synthesized as a 108-amino acid pre pro-BNP molecule that is proteolytically processed into a 76-amino acid "NT pro BNP" and the 32-amino acid BNP molecule. Because of its relationship to BNP, the concentration of NT pro-BNP molecule can also provide diagnostic or prognostic information in patients. The phrase "marker related to BNP or BNP related peptide" refers to any polypeptide that originates from the pre pro-BNP molecule, other than the 32-amino acid BNP molecule itself. Thus, a marker related to or associated with BNP includes the NT pro-BNP molecule, the pro domain, a fragment of BNP that is smaller than the entire 32-amino acid sequence, a fragment of pre pro-BNP other than BNP, and a fragment of the pro domain.

Biomarker Classes

LTBP2 could be used as a biomarker for cardiovascular diseases, hematological diseases, neurological diseases, cancer, endocrinological diseases and urological diseases in different classes:

Disease Biomarker: a biomarker that relates to a clinical outcome or measure of disease.

Efficacy Biomarker: a biomarker that reflects beneficial effect of a given treatment.

Staging Biomarker: a biomarker that distinguishes between different stages of a chronic disorder.

Surrogate Biomarker: a biomarker that is regarded as a valid substitute for a clinical outcomes measure.

Toxicity Biomarker: a biomarker that reports a toxicological effect of a drug on an in vitro or in vivo system.

Mechanism Biomarker: a biomarker that reports a downstream effect of a drug.

Target Biomarker: a biomarker that reports interaction of the drug with its target.

One embodiment of the invention is a method of use of LTBP2 as a biomarker for a disease comprising:
(a) obtaining a biological sample from a mammal,
(b) measuring the level of LTBP2 in the biological sample,
(c) obtaining a control sample from a mammal,
(d) measuring the level of LTBP2 in the control sample,
(e) comparing the level of LTBP2 in the biological sample with the level of LTBP2 in a control sample, and
(f) diagnosing a disease based upon the LTBP2 level of the biological sample in comparison to the control sample.

The biological sample in step (a) of the methods is in a preferred embodiment a biological sample comprised in a group of samples consisting of a blood sample, a plasma sample, a serum sample, a tissue sample, a oral mucosa sample, a saliva sample, an interstitial fluid sample or an urine sample. The blood sample is for example a whole blood sample, a fractionated blood sample, a platelet sample, a neutrophil sample, a leukocyte sample, a white blood cell sample, a monocyte sample, a red blood cell sample, a granulocyte sample, and a erythrocyte sample. A tissue sample is for example a sample collected from muscle, adipose, heart or skin.

In a preferred embodiment LTBP2 is used as a biomarker diagnosing a disease which is associated with altered LTBP2 levels. Another preferred embodiment LTBP2 is used as a biomarker for identifying an individual risk for developing a disease, or for predicting an adverse outcome in a patient diagnosed with a disease, Use of LTBP2 as a disease biomarker in diagnostics is based by the comparison of LTBP2 level in a biological sample from a diseased mammal with the LTBP2 level in a control sample from a healthy or normal mammal or a group of healthy or normal mammals. Does the LTBP2 level in the diseased mammal differs from the LTBP2 level in a normal or healthy mammal then the diseased mammal is diagnosed with a disease associated with altered LTBP2 level.

Furthermore, using LTBP2 as a staging biomarker, the LTBP2 levels of a diseased mammal are compared with LTBP2 levels of a mammal with a LTBP2-associated disease already diagnosed with different stages or severity of said disease, allows the diagnose of said first diseased mammal specifying the severity of the LTBP2-associated disease.

A control sample can be a sample taken from a mammal. A control sample can be a previously taken sample from a mammal, as a LTBP2 level in a control sample can be a predetermined level of LTBP2 measured in a previously taken sample. The level of LTBP2 in a control sample or in a biological sample can be determined for example as a relative value and as an absolute value. A previously measured LTBP2 level from a control sample can be for example stored in a database, in an internet publication, in an electronically accessible form, in a publication. Comparing the level of LTBP2 of a biological sample to a control sample may be comparing relative values or absolute quantified values.

Another embodiment is a method of use of LTBP2 as a biomarker for guiding a therapy of a disease comprising:
(a) obtaining a baseline level of LTBP2 in biological sample from a diseased mammal,
(b) administering to the diseased mammal a treatment for the disease,
(c) obtaining one or more subsequent biological samples from the diseased mammal
(d) measuring the level of LTBP2 in the one or more subsequent biological samples,
(e) comparing the level of LTBP2 in the one or more subsequent biological samples with the baseline sample, and
(f) determining whether increased dosages, additional or alternative treatments are necessary based on LTBP2 levels obtained from one or more subsequent biological samples compared to the baseline LTBP2 level.

In a preferred embodiment LTBP2 is used as a biomarker for guiding a therapy in a disease which is associated with altered LTBP2 levels.

Use of LTBP2 as a disease, efficacy or surrogate endpoint biomarker in diagnostics is based by the comparison of LTBP2 level in a biological sample from a diseased mammal before treatment (the baseline sample level) with the LTBP2 level in subsequent samples from said mammal receiving a treatment for the disease. Does the LTBP2 level in the baseline sample differs from the LTBP2 level in the subsequent samples then the therapy can be considered as successful. Does the LTBP2 level in the baseline sample does not differ or differs only slightly from the LTBP2 level in the subsequent samples then the therapy can be considered as not successful. If the therapy is considered not successful increased dosages of the same therapy, repeat of the same therapy or an alternative treatment which is different from the first therapy can be considered.

The biological sample in step (a) of the methods is in a preferred embodiment a biological sample comprised in a group of samples consisting of a blood sample, a plasma sample, a serum sample, a tissue sample, a oral mucosa sample, a saliva sample, an interstitial fluid sample or an urine sample. The blood sample is for example a whole blood sample, a fractionated blood sample, a platelet sample, a neutrophil sample, a leukocyte sample, a white blood cell sample, a monocyte sample, a red blood cell sample, a granulocyte sample, and a erythrocyte sample. A tissue sample is for example a sample collected from muscle, adipose, heart, skin or a biopsy.

In a preferred embodiment the level of LTBP2 is determined by determining the level of LTBP2 polynucleotide.

In another preferred embodiment the level of LTBP2 is determined by determining the level of LTBP2 polypeptide.

In a further preferred embodiment the level of LTBP2 is determined by determining the level of LTBP2 activity.

In a preferred embodiment the disease associated with LTBP2 is comprised in a group of diseases consisting of cardiovascular diseases, hematological diseases, neurological diseases, respiratory diseases, gastroenterological diseases, and urological diseases. In a more preferred embodiment the cardiovascular disease associated with LTBP2 is comprised in a group of diseases consisting of congestive heart failure, pulmonary hypertension, left ventricular dysfunction, and right ventricular dysfunction, myocardial infarction, coronary occlusion, disease, ischemic heart disease, cardiac hypertrophy disorder, cardiac fibrosis disorders.

In a preferred embodiment of the invention the mammal is a human.

In a preferred embodiment of the invention the level of LTBP2 of the biological sample is elevated compared to the control sample.

Another embodiment of the present invention prefers the use of LTBP2 in combination with the use of one or more biomarkers, more preferably with biomarkers used in diagnosing LTBP2-associated diseases.

In a preferred embodiment of the invention the use of LTBP2 is combined with the use of one or more biomarkers which are comprised in a group of biomarkers consisting of CRTAC, PRSS23, FN1, TGFB2, NPR3, CTGF, BNP, ANP, Troponin, CRP, Myoglobin, CK-MB and metabolites.

In a further preferred embodiment the use of LTBP2 is combined with the use of one or more clinical biomarkers which are comprised in a group of biomarkers consisting of blood pressure, heart rate, pulmonary artery pressure, or system vascular resistance.

In a further preferred embodiment the use of LTBP2 is combined with the use of one or more diagnostic imaging methods which are comprised in a group of methods consisting of PET (Positron Emission Tomography), CT (Computed Tomography), ultrasonic, SPECT (Single Photon Emission Computed Tomography), Echocardiography, or Impedance Cardiography.

In a further preferred embodiment the use of LTBP2 is combined with the use of one or more diagnostic imaging methods which are comprised in a group of methods consisting of PET (Positron Emission Tomography), CT (Computed Tomography), ultrasonic, SPECT (Single Photon Emission Computed Tomography), Echocardiography, Impedance Cardiography, blood pressure, heart rate, pulmonary artery pressure, systemic vascular resistance, CRTAC, PRSS23, FN1, TGFB2, NPR3, CTGF, BNP, ANP, Troponin, CRP, Myoglobin, CK-MB, and metabolites.

In a further preferred embodiment is a kit for identifying an individual risk for developing a disease, for predicting a disease or an adverse outcome in a patient diagnosed with a disease, or for guiding a therapy in a patient with a disease, the kit comprising one or more antibodies which specifically binds LTBP2, detection means, one or more containers for collecting and or holding the biological sample, and an instruction for its use.

Another preferred embodiment is a kit for identifying an individual risk for developing a disease, for predicting a disease or an adverse outcome in a patient diagnosed with a disease, or for guiding a therapy in a patient with a disease, the kit comprising one or more probes or primers for detecting LTBP2 mRNA, detection means, one or more containers for collecting and or holding the biological sample, and an instruction for its use.

Another preferred embodiment is a kit for identifying an individual risk for developing a disease, for predicting a disease or an adverse outcome in a patient diagnosed with a disease, or for guiding a therapy in a patient with a disease, the kit comprising one or more substrates for detecting LTBP2 activity, detection means, one or more containers for collecting and or holding the biological sample, and an instruction for its use.

Determination of a Therapeutically Effective Dose

The determination of a therapeutically effective dose is well within the capability of those skilled in the art. A therapeutically effective dose refers to that amount of active ingredient which increases or decreases LTBP2 activity relative to LTBP2 activity which occurs in the absence of the therapeutically effective dose. For any compound, the therapeutically effective dose can be estimated initially either in cell culture assays or in animal models, usually mice, rabbits, dogs, or pigs. The animal model also can be used to determine the appropriate concentration range and route of administration. Such information can then be used to determine useful doses and routes for administration in humans.

Therapeutic efficacy and toxicity, e.g., $ED_{50}$ (the dose therapeutically effective in 50% of the population) and $LD_{50}$ (the dose lethal to 50% of the population), can be determined by standard pharmaceutical procedures in cell cultures or experimental animals. The dose ratio of toxic to therapeutic effects is the therapeutic index, and it can be expressed as the ratio, $LD_{50}/ED_{50}$. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the $ED_{50}$ with little or no toxicity. The dosage varies within this range depending upon the dosage form employed, sensitivity of the patient, and the route of administration. The exact dosage will be determined by the practitioner, in light of factors related to the subject that requires treatment. Dosage and administration are adjusted to provide sufficient levels of the active ingredient or to maintain the desired effect. Factors which can be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions can be administered every 3 to 4 days, every week, or once every two weeks depending on the half-life and clearance rate of the particular formulation.

Normal dosage amounts can vary from 0.1 micrograms to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc. If the reagent is a single-chain antibody, polynucleotides encoding the antibody can be constructed and introduced into a cell either ex vivo or in vivo using well-established techniques including, but not limited to, transferrin-polycation-mediated DNA transfer, transfection with naked or encapsulated nucleic acids, liposome-mediated cellular fusion, intracellular transportation of DNA-coated latex beads, protoplast fusion, viral infection, electroporation, "gene gun", and DEAE- or calcium phosphate-mediated transfection.

If the expression product is mRNA, the reagent is preferably an antisense oligonucleotide or a ribozyme. Polynucleotides which express antisense oligonucleotides or ribozymes can be introduced into cells by a variety of methods, as described above. Preferably, a reagent reduces expression of LTBP2 gene or the activity of LTBP2 by at least about 10, preferably about 50, more preferably about 75, 90, or 100% relative to the absence of the reagent. The effectiveness of the mechanism chosen to decrease the level of expression of LTBP2 gene or the activity of LTBP2 can be assessed using methods well known in the art, such as hybridization of nucleotide probes to LTBP2-specific mRNA, quantitative RT-PCR, immunologic detection of LTBP2, or measurement of LTBP2 activity.

In any of the embodiments described above, any of the pharmaceutical compositions of the invention can be administered in combination with other appropriate therapeutic agents. Selection of the appropriate agents for use in combination therapy can be made by one of ordinary skill in the art, according to conventional pharmaceutical principles. The combination of therapeutic agents can act synergistically to effect the treatment or prevention of the various disorders described above. Using this approach, one may be able to achieve therapeutic efficacy with lower dosages of each agent, thus reducing the potential for adverse side effects. Any of the therapeutic methods described above can be applied to any subject in need of such therapy, including, for example, mammals such as dogs, cats, cows, horses, rabbits, monkeys, and most preferably, humans.

Nucleic acid molecules of the invention are those nucleic acid molecules which are contained in a group of nucleic acid molecules consisting of (i) nucleic acid molecules encoding a polypeptide comprising the amino acid sequence of SEQ ID NO: 3 or SEQ ID NO: 4, (ii) nucleic acid molecules comprising the sequence of SEQ ID NO: 1 or SEQ ID NO: 2, (iii) nucleic acid molecules having the sequence of SEQ ID NO: 1 or SEQ ID NO: 2, (iv) nucleic acid molecules the complementary strand of which hybridizes under stringent conditions to a nucleic acid molecule of (i), (ii), or (iii), (v) nucleic acid molecules the sequence of which differs from the sequence of a nucleic acid molecule of (iii) due to the degeneracy of the genetic code, (vi) nucleic acid molecules which have a sequence identity of at least 80%, 85%, 90%, 95%, 98% or 99%; and (vii) wherein the polypeptide encoded by said nucleic acid molecules of (i)-(vi) have LTBP2 activity.

Polypeptides of the invention are those polypeptides which are contained in a group of polypeptides consisting of (i) polypeptides having the sequence of SEQ ID NO: 3 or 4, (ii) polypeptides comprising the sequence of SEQ ID NO: 3 or 4, (iii) polypeptides encoded by nucleic acid molecules of the invention and (iv) polypeptides which show at least 99%, 98%, 95%, 90%, or 80% identity with a polypeptide of (i), (ii), or (iii).

An object of the invention is a method of screening for therapeutic agents useful in the treatment of a disease comprised in a group of diseases consisting of cardiovascular diseases, hematological diseases, neurological diseases, cancer, endocrinological diseases and urological diseases in a mammal comprising the steps of (i) contacting a test compound with a LTBP2 polypeptide, (ii) detect binding of said test compound to said LTBP2 polypeptide. E.g., compounds that bind to the LTBP2 polypeptide are identified potential therapeutic agents for such a disease.

Another object of the invention is a method of screening for therapeutic agents useful in the treatment of a disease comprised in a group of diseases consisting of cardiovascular diseases, hematological diseases, neurological diseases, cancer, endocrinological diseases and urological diseases in a mammal comprising the steps of (i) determining the activity of a LTBP2 polypeptide at a certain concentration of a test compound or in the absence of said test compound, (ii) determining the activity of said polypeptide at a different concentration of said test compound. E.g., compounds that lead to a difference in the activity of the LTBP2 polypeptide in (i) and (ii) are identified potential therapeutic agents for such a disease.

Another object of the invention is a method of screening for therapeutic agents useful in the treatment of a disease comprised in a group of diseases consisting of cardiovascular diseases, hematological diseases, neurological diseases, cancer, endocrinological diseases and urological diseases in a mammal comprising the steps of (i) determining the activity of a LTBP2 polypeptide at a certain concentration of a test compound, (ii) determining the activity of a LTBP2 polypeptide at the presence of a compound known to be a regulator of a LTBP2 polypeptide. E.g., compounds that show similar effects on the activity of the LTBP2 polypeptide in (i) as compared to compounds used in (ii) are identified potential therapeutic agents for such a disease.

Other objects of the invention are methods of the above, wherein the step of contacting is in or at the surface of a cell.

Other objects of the invention are methods of the above, wherein the cell is in vitro.

Other objects of the invention are methods of the above, wherein the step of contacting is in a cell-free system.

Other objects of the invention are methods of the above, wherein the polypeptide is coupled to a detectable label.

Other objects of the invention are methods of the above, wherein the compound is coupled to a detectable label.

Other objects of the invention are methods of the above, wherein the test compound displaces a ligand which is first bound to the polypeptide.

Other objects of the invention are methods of the above, wherein the polypeptide is attached to a solid support.

Other objects of the invention are methods of the above, wherein the compound is attached to a solid support.

Another object of the invention is a method of screening for therapeutic agents useful in the treatment of a disease comprised in a group of diseases consisting of cardiovascular diseases, hematological diseases, neurological diseases, cancer, endocrinological diseases and urological diseases in a mammal comprising the steps of (i) contacting a test compound with a LTBP2 polynucleotide, (ii) detect binding of said test compound to said LTBP2 polynucleotide. Compounds that, e.g., bind to the LTBP2 polynucleotide are potential therapeutic agents for the treatment of such diseases.

Another object of the invention is the method of the above, wherein the nucleic acid molecule is RNA.

Another object of the invention is a method of the above, wherein the contacting step is in or at the surface of a cell.

Another object of the invention is a method of the above, wherein the contacting step is in a cell-free system.

Another object of the invention is a method of the above, wherein the polynucleotide is coupled to a detectable label.

Another object of the invention is a method of the above, wherein the test compound is coupled to a detectable label.

Another object of the invention is a method of diagnosing a disease comprised in a group of diseases consisting of cardiovascular diseases, hematological diseases, neurological diseases, cancer, endocrinological diseases and urological diseases in a mammal comprising the steps of (i) determining the amount of a LTBP2 polynucleotide in a sample taken from said mammal, (ii) determining the amount of LTBP2 polynucleotide in healthy and/or diseased mammal. A disease is diagnosed, e.g., if there is a substantial similarity in the amount of LTBP2 polynucleotide in said test mammal as compared to a diseased mammal.

Another object of the invention is a pharmaceutical composition for the treatment of a disease comprised in a group of diseases consisting of cardiovascular diseases, hematological diseases, neurological diseases, cancer, endocrinological diseases and urological diseases in a mammal comprising a therapeutic agent which binds to a LTBP2 polypeptide.

Another object of the invention is a pharmaceutical composition for the treatment of a disease comprised in a group of diseases consisting of cardiovascular diseases, hematological diseases, neurological diseases, cancer, endocrinological diseases and urological diseases in a mammal comprising a therapeutic agent which regulates the activity of a LTBP2 polypeptide.

Another object of the invention is a pharmaceutical composition for the treatment of a disease comprised in a group of diseases consisting of cardiovascular diseases, hematological diseases, neurological diseases, cancer, endocrinological diseases and urological diseases in a mammal comprising a therapeutic agent which regulates the activity of a LTBP2 polypeptide, wherein said therapeutic agent is (i) a small molecule, (ii) an RNA molecule, (iii) an antisense oligonucleotide, (iv) a polypeptide, (v) an antibody, or (vi) a ribozyme.

Another object of the invention is a pharmaceutical composition for the treatment of a disease comprised in a group of diseases consisting of cardiovascular diseases, hematological diseases, neurological diseases, cancer, endocrinological diseases and urological diseases in a mammal comprising a LTBP2 polynucleotide.

Another object of the invention is a pharmaceutical composition for the treatment of a disease comprised in a group of diseases consisting of cardiovascular diseases, hematological diseases, neurological diseases, cancer, endocrinological diseases and urological diseases in a mammal comprising a LTBP2 polypeptide.

Another object of the invention is the use of regulators of a LTBP2 for the preparation of a pharmaceutical composition for the treatment of a disease comprised in a group of diseases consisting of cardiovascular diseases, hematological diseases, neurological diseases, cancer, endocrinological diseases and urological diseases in a mammal.

Another object of the invention is a method for the preparation of a pharmaceutical composition useful for the treatment of a disease comprised in a group of diseases consisting of cardiovascular diseases, hematological diseases, neurological diseases, cancer, endocrinological diseases and urological diseases in a mammal comprising the steps of (i) identifying a regulator of LTBP2, (ii) determining whether said regulator ameliorates the symptoms of a disease comprised in a group of diseases consisting of cardiovascular diseases, hematological diseases, neurological diseases, cancer, endocrinological diseases and urological diseases in a mammal; and (iii) combining of said regulator with an acceptable pharmaceutical carrier.

Another object of the invention is the use of a regulator of LTBP2 for the regulation of LTBP2 activity in a mammal having a disease comprised in a group of diseases consisting of cardiovascular diseases, hematological diseases, neurological diseases, cancer, endocrinological diseases and urological diseases.

The uses, methods or compositions of the invention are useful for each single disease comprised in a group of diseases consisting of cardiovascular diseases, hematological diseases, neurological diseases, cancer, endocrinological diseases and urological diseases.

The examples below are provided to illustrate the subject invention. These examples are provided by way of illustration and are not included for the purpose of limiting the invention.

EXAMPLES

Example 1:

Search for Homologous Sequences in Public Sequence Data Bases

The degree of homology can readily be calculated by known methods. Preferred methods to determine homology are designed to give the largest match between the sequences tested. Methods to determine homology are codified in publicly available computer programs such as BestFit, BLASTP, BLASTN, and FASTA. The BLAST programs are publicly available from NCBI and other sources in the internet.

For LTBP2 the following hits to known sequences were identified by using the BLAST algorithm [Altschul S F, Madden T L, Schaffer A A, Zhang J, Zhang Z, Miller W, Lipman D J; Nucleic Acids Res 1997 Sep. 1; 25(17): 3389-402] and the following set of parameters: matrix=BLOSUM62 and low complexity filter. The following databases were searched: NCBI (non-redundant database) and DERWENT patent database (Geneseq).

The following hits were found:
>dbj|DD288037.1| LYMPHATIC ENDOTHELIAL GENES, Length=7017, Score=1.391e+04 bits (7017), Expect=0.0, Identities=7017/7017 (100%)
>gb|S82451.1| latent transforming growth factor-beta-binding protein-2 [human, fibroblast cell line CC102, mRNA, 7017 nt], Length=7017, Score=1.391e+04 bits (7017), Expect=0.0, Identities=7017/7017 (100%)
>ref|NM_000428.2| *Homo sapiens* latent transforming growth factor beta binding protein 2 (LTBP2), mRNA, Length=8568, Score=1.384e+04 bits (6982), Expect=0.0, Identities=6982/6982 (100%)
>dbj|DD018049.1| A marker of heart failure and its use Length=8657, Score=1.376e+04 bits (6940), Expect=0.0, Identities=6967/6972 (99%), Gaps=3/6972 (0%)
>emb|CQ874661.1|Sequence 21 from Patent WO2004075835, Length=7000, Score=1.369e+04 bits (6906), Expect=0.0, Identities=6954/6966 (99%), Gaps=3/6966 (0%)
>emb|Z37976.1|HSLTBP2MR H. sapiens mRNA for latent transforming growth factor-beta binding protein (LTBP-2), Length=7000, Score=1.369e+04 bits (6906), Expect=0.0, Identities=6954/6966 (99%), Gaps=3/6966 (0%)
>gb|BC078659.1| Homo sapiens latent transforming growth factor beta binding protein 2, mRNA (cDNA clone MGC:87426 IMAGE:30343778), complete cds, Length=6901, Score=1.361e+04 bits (6867), Expect=0.0, Identities=6897/6905 (99%), Gaps=4/6905 (0%)
>dbj|AB209865.1| Homo sapiens mRNA for latent transforming growth factor beta binding protein 2 variant protein, Length=7803, Score=1.232e+04 bits (6216), Expect=0.0, Identities=6228/6232 (99%)

Example 2:

Expression Profiling

Total cellular RNA was isolated from cells by one of two standard methods: 1) guanidine isothiocyanate/Cesium chloride density gradient centrifugation [Kellogg, (1990)]; or with the Tri-Reagent protocol according to the manufacturer's specifications (Molecular Research Center, Inc., Cincinnati, Ohio). Total RNA prepared by the Tri-reagent protocol was treated with DNAse I to remove genomic DNA contamination.

For relative quantitation of the mRNA distribution of LTBP2, total RNA from each cell or tissue source was first reverse transcribed. 85 μg of total RNA was reverse transcribed using 1 μmole random hexamer primers, 0.5 mM each of dATP, dCTP, dGTP and dTTP (Qiagen, Hilden, Germany), 3000 U RnaseQut (Invitrogen, Groningen, Netherlands) in a final volume of 680 μl. The first strand synthesis buffer and Omniscript reverse transcriptase (2 u/μl) were from (Qiagen, Hilden, Germany). The reaction was incubated at 37° C. for 90 minutes and cooled on ice. The volume was adjusted to 6800 μl with water, yielding a final concentration of 12.5 ng/μl of starting RNA.

For relative quantitation of the distribution of LTBP2 mRNA in cells and tissues the Applied Bioscience 7900HT Sequence Detection system was used according to the manufacturer's specifications and protocols. PCR reactions were set up to quantitate LTBP2 and the housekeeping genes HPRT (hypoxanthine phosphoribosyltransferase), GAPDH (glyceraldehyde-3-phosphate dehydrogenase), β-actin, and others. Forward and reverse primers and probes for LTBP2 were designed using the Applied Bioscience ABI Primer Express™ software and were synthesized by Eurogentec (Belgium). The LTBP2 forward primer sequence was: Primer1 (SEQ ID NO: 8). The LTBP2 reverse primer sequence was Primer2 (SEQ ID NO: 10). Probe1 (SEQ ID NO: 9), labelled with FAM (carboxyfluorescein succinimidyl ester) as the reporter dye and TAMRA (carboxytetramethylrhodamine) as the quencher, is used as a probe for LTBP2. The following reagents were prepared in a total of 20 μl: 1× qPCR-MasterMix (Eurogentec; Belgium) and Probe1 (SEQ ID NO: 9), LTBP2 forward and reverse primers each at 200 nM, 200 nM LTBP2 FAM/TAMRA-labelled probe, and 5 μl of template cDNA. Thermal cycling parameters were 2 min at 50° C., followed by 10 min at 95° C., followed by 40 cycles of melting at 95° C. for 15 sec and annealing/extending at 60° C. for 1 min.

Calculation of Corrected CT Values

The CT (threshold cycle) value is calculated as described in the "Quantitative determination of nucleic acids" section. The CF-value (factor for threshold cycle correction) is calculated as follows:

1. PCR reactions were set up to quantitate the housekeeping genes (HKG) for each cDNA sample.
2. $CT_{HKG}$-values (threshold cycle for housekeeping gene) were calculated as described in the "Quantitative determination of nucleic acids" section.
3. $CT_{HKG}$-mean values (CT mean value of all HKG tested on one cDNAs) of all HKG for each cDNA are calculated (n=number of HKG):

$$CT_{HKG\text{-}n}\text{-mean value} = (CT_{HKG1}\text{-value} + CT_{HKG2}\text{-value} + \ldots + CT_{HKG\text{-}n}\text{-value})/n$$

4. $CT_{pannel}$ mean value (CT mean value of all HKG in all tested cDNAs)=

$$(CT_{HKG1}\text{-mean value} + CT_{HKG2}\text{-mean value} + \ldots + CT_{HKG\text{-}y}\text{-mean value})/y$$

(y=number of cDNAs)

5. $CF_{cDNA\text{-}n}$(correction factor for cDNA n)=$CT_{pannel}$-mean value — $CT_{HKG\text{-}n}$-mean value
6. $CT_{cDNA\text{-}n}$(CT value of the tested gene for the cDNA n)+$CF_{cDNA\text{-}n}$(correction factor for cDNA n)=$CT_{cor\text{-}cDNA\text{-}n}$ (corrected CT value for a gene on cDNA n)

Calculation of Relative Expression

Definition: highest $CT_{cor\text{-}cDNA\text{-}n} \neq 40$ is defined as $CT_{cor\text{-}cDNA}$ [high]

Relative Expression=$2^{(CT_{cor\text{-}cDNA[high]} - CT_{cor\text{-}cDNA\text{-}n})}$ Tissues The expression of LTBP2 was investigated in the tissues in table 1.

Expression Profile

The results of the mRNA-quantification (expression profiling) is shown in Table 1.

TABLE 1

Relative expression of LTBP2 in various human tissues.

| Tissue | Relative Expression |
|---|---|
| T-cells peripheral blood CD4+ | 2 |
| monocytes | 20 |
| monocytes HIV-1 infected | 20 |
| fetal heart | 193 |
| heart | 8306 |
| heart | 6252 |
| heart | 6517 |
| heart myocardial infarction | 1924 |
| heart myocardial infarction | 2106 |
| pericardium | 399 |
| heart atrium (right) | 1160 |
| heart atrium (right) | 350 |
| heart atrium (left) | 290 |
| heart atrium (left) | 635 |
| heart ventricle (left) | 1370 |
| heart ventricle (left) | 1235 |
| heart ventricle (right) | 29 |
| heart ventricle (right) | 365 |
| heart apex | 118 |
| Purkinje fibers | 1209 |
| interventricular septum | 265 |

TABLE 1-continued

Relative expression of LTBP2 in various human tissues.

| Tissue | Relative Expression |
| --- | --- |
| fetal aorta | 352 |
| aorta | 2385 |
| aorta | 832 |
| aorta | 549 |
| arcus aorta | 976 |
| aorta valve | 3902 |
| artery | 108 |
| coronary artery | 12766 |
| coronary artery | 2721 |
| pulmonary artery | 2557 |
| carotid artery | 1563 |
| mesenteric artery | 176 |
| arteria radialis | 143 |
| vein | 3281 |
| pulmonic valve | 3848 |
| vein (saphena magna) | 52 |
| (caval) vein | 1261 |
| coronary artery endothel cells | 3040 |
| coronary artery smooth muscle primary cells | 1144 |
| aortic smooth muscle cells | 4360 |
| pulmonary artery smooth muscle cells | 3822 |
| aortic endothel cells | 5595 |
| HUVEC cells | 5078 |
| pulmonary artery endothel cells | 2684 |
| iliac artery endothel cells | 3956 |
| skin | 340 |
| adrenal gland | 976 |
| thyroid | 56267 |
| thyroid tumor | 1951 |
| pancreas | 1510 |
| esophagus | 1160 |
| esophagus tumor | 347 |
| stomach | 261 |
| stomach tumor | 1053 |
| colon | 27 |
| colon tumor | 1563 |
| small intestine | 61 |
| ileum | 1675 |
| ileum tumor | 181 |
| ileum chronic inflammation | 56 |
| Caco-2 cells | 33 |
| rectum | 220 |
| rectum tumor | 338 |
| fetal liver | 33 |
| liver | 26 |
| liver | 0 |
| liver | 3 |
| liver liver cirrhosis | 474 |
| liver tumor | 193 |
| HuH-7 cells | 15 |
| leukocytes (peripheral blood) | 177 |
| Jurkat (T-cells) | 3 |
| Raji (B-cells) | 0 |
| bone marrow | 54 |
| HL-60 (promyeloblast-cells) | 1 |
| THP-1 (monocytes peripheral blood) | 3 |
| peripheral blood CD56+ (natural killer cells) | 27 |
| erythrocytes | 0 |
| lymphnode | 102 |
| thymus | 51 |
| thrombocytes | 120 |
| bone marrow stromal cells | 3956 |
| bone marrow CD71+ cells | 7 |
| bone marrow CD33+ cells | 3 |
| bone marrow CD34+ cells | 38 |
| bone marrow CD15+ cells | 39 |
| cord blood CD71+ cells | 12 |
| cord blood CD34+ cells | 16 |
| neutrophils cord blood | 27 |
| T-cells peripheral blood CD8+ | 37 |
| monocytes peripheral blood CD14+ | 2 |
| B-cells peripheral blood CD19+ | 46 |
| neutrophils peripheral blood | 25 |
| spleen | 31 |
| skeletal muscle | 187 |
| cartilage | 1563 |
| adipose | 4040 |
| adipose | 576 |
| adipose | 1017 |
| fetal adipose | 1409 |
| brain | 755 |
| cerebellum | 982 |
| cerebral cortex | 50 |
| frontal lobe | 996 |
| occipital lobe | 1938 |
| parietal lobe | 94 |
| temporal lobe | 25 |
| substantia nigra | 7 |
| caudatum | 24 |
| hippocampus | 14 |
| thalamus | 0 |
| posteroventral thalamus | 218 |
| dorsalmedial thalamus | 55 |
| hypothalamus | 147 |
| dorsal root ganglia | 76863 |
| spinal cord | 288 |
| spinal cord (ventral horn) | 74 |
| spinal cord (dorsal horn) | 104 |
| glial tumor H4 cells | 24 |
| retina | 141 |
| fetal lung | 1342 |
| fetal lung fibroblast IMR-90 cells | 2180 |
| fetal lung fibroblast MRC-5 cells | 1031 |
| lung | 19349 |
| lung | 21921 |
| lung tumor | 12944 |
| lung COPD | 1305 |
| trachea | 340 |
| primary bronchia | 580 |
| secondary bronchia | 744 |
| bronchial smooth muscle cells | 1795 |
| small airway epithelial cells | 292 |
| small airway epithelial cells | 338 |

Example 3:

Antisense Analysis

Knowledge of the correct, complete cDNA sequence coding for LTBP2 enables its use as a tool for antisense technology in the investigation of gene function. Oligonucleotides, cDNA or genomic fragments comprising the antisense strand of a polynucleotide coding for LTBP2 are used either in vitro or in vivo to inhibit translation of the mRNA. Such technology is now well known in the art, and antisense molecules can be designed at various locations along the nucleotide sequences. By treatment of cells or whole test animals with such antisense sequences, the gene of interest is effectively turned off. Frequently, the function of the gene is ascertained by observing behavior at the intracellular, cellular, tissue or organismal level (e.g., lethality, loss of differentiated function, changes in morphology, etc.).

In addition to using sequences constructed to interrupt transcription of a particular open reading frame, modifications of gene expression is obtained by designing antisense sequences to intron regions, promoter/enhancer elements, or even to trans-acting regulatory genes.

Example 4:

Expression of LTBP2

Expression of LTBP2 is accomplished by subcloning the cDNAs into appropriate expression vectors and transfecting the vectors into expression hosts such as, e.g., *E. coli*. In a particular case, the vector is engineered such that it contains a promoter for β-galactosidase, upstream of the cloning site, followed by sequence containing the amino-terminal Methionine and the subsequent seven residues of β-galactosidase. Immediately following these eight residues is an engineered bacteriophage promoter useful for artificial priming and transcription and for providing a number of unique endonuclease restriction sites for cloning.

Induction of the isolated, transfected bacterial strain with Isopropyl-β-D-thiogalactopyranoside (IPTG) using standard methods produces a fusion protein corresponding to the first seven residues of β-galactosidase, about 15 residues of "linker", and the peptide encoded within the cDNA. Since cDNA clone inserts are generated by an essentially random process, there is probability of 33% that the included cDNA will lie in the correct reading frame for proper translation. If the cDNA is not in the proper reading frame, it is obtained by deletion or insertion of the appropriate number of bases using well known methods including in vitro mutagenesis, digestion with exonuclease III or mung bean nuclease, or the inclusion of an oligonucleotide linker of appropriate length.

The LTBP2 cDNA is shuttled into other vectors known to be useful for expression of proteins in specific hosts. Oligonucleotide primers containing cloning sites as well as a segment of DNA (about 25 bases) sufficient to hybridize to stretches at both ends of the target cDNA is synthesized chemically by standard methods. These primers are then used to amplify the desired gene segment by PCR. The resulting gene segment is digested with appropriate restriction enzymes under standard conditions and isolated by gel electrophoresis. Alternately, similar gene segments are produced by digestion of the cDNA with appropriate restriction enzymes. Using appropriate primers, segments of coding sequence from more than one gene are ligated together and cloned in appropriate vectors. It is possible to optimize expression by construction of such chimeric sequences.

Suitable expression hosts for such chimeric molecules include, but are not limited to, mammalian cells such as Chinese Hamster Ovary (CHO) and human 293 cells., insect cells such as Sf9 cells, yeast cells such as *Saccharomyces cerevisiae* and bacterial cells such as *E. coli*. For each of these cell systems, a useful expression vector also includes an origin of replication to allow propagation in bacteria, and a selectable marker such as the β-lactamase antibiotic resistance gene to allow plasmid selection in bacteria. In addition, the vector may include a second selectable marker such as the neomycin phosphotransferase gene to allow selection in transfected eukaryotic host cells. Vectors for use in eukaryotic expression hosts require RNA processing elements such as 3' polyadenylation sequences if such are not part of the cDNA of interest.

Additionally, the vector contains promoters or enhancers which increase gene expression. Such promoters are host specific and include MMTV, SV40, and metallothionine promoters for CHO cells; trp, lac, tac and T7 promoters for bacterial hosts; and alpha factor, alcohol oxidase and PGH promoters for yeast. Transcription enhancers, such as the rous sarcoma virus enhancer, are used in mammalian host cells. Once homogeneous cultures of recombinant cells are obtained through standard culture methods, large quantities of recombinantly produced LTBP2 are recovered from the conditioned medium and analyzed using chromatographic methods known in the art. For example, LTBP2 can be cloned into the expression vector pcDNA3, as exemplified herein. This product can be used to transform, for example, HEK293 or COS by methodology standard in the art. Specifically, for example, using Lipofectamine (Gibco BRL catalog no. 18324-020) mediated gene transfer.

Example 5:

Isolation of Recombinant LTBP2

LTBP2 is expressed as a chimeric protein with one or more additional polypeptide domains added to facilitate protein purification. Such purification facilitating domains include, but are not limited to, metal chelating peptides such as histidine-tryptophan modules that allow purification on immobilized metals [Appa Rao, (1997)] and the domain utilized in the FLAGS extension/affinity purification system (Immunex Corp., Seattle, Wash.). The inclusion of a cleavable linker sequence such as Factor Xa or enterokinase (Invitrogen, Groningen, The Netherlands) between the purification domain and the LTBP2 sequence is useful to facilitate expression of LTBP2.

The following example provides a method for purifying LTBP2.

LTBP2 is generated using the baculovirus expression system BAC-TO-BAC (GIBCO BRL) based on *Autographa californica* nuclear polyhedrosis virus (AcNPV) infection of *Spodoptera frugiperda* insect cells (Sf9 cells).

cDNA encoding proteins cloned into either the donor plasmid pFASTBAC1 or pFASTBAC-HT which contain a mini-Tn7 transposition element. The recombinant plasmid is transformed into DH10BAC competent cells which contain the parent bacmid bMON14272 (AcNPV infectious DNA) and a helper plasmid. The mini-Tn7 element on the pFASTBAC donor can transpose to the attTn7 attachment site on the bacmid thus introducing the gene into the viral genome. Colonies containing recombinant bacmids are identified by disruption of the lacZ gene. The bacmid construct can then be isolated and infected into insect cells (Sf9 cells) resulting in the production of infectious recombinant baculovirus particles and expression of either unfused recombinant enzyme (pFastbac1) or LTBP2-His fusion protein (pFastbacHT).

Cells are harvested and extracts prepared 24, 48 and 72 hours after transfection. Expression of LTBP2 is confirmed by coomassie staining after sodium dodecyl sulphate-polyacrylamide gel electrophoresis (SDS-PAGE) and western blotting onto a PVDF membrane of an unstained SDS-PAGE. The protein-His fusion protein is detected due to the interaction between the Ni-NTA HRP conjugate and the His-tag which is fused to LTBP2.

Example 6:

Production of LTBP2 Specific Antibodies

Two approaches are utilized to raise antibodies to LTBP2, and each approach is useful for generating either polyclonal or monoclonal antibodies. In one approach, denatured protein from reverse phase HPLC separation is obtained in quantities up to 75 mg. This denatured protein is used to immunize mice or rabbits using standard protocols; about 100 μg are adequate for immunization of a mouse, while up to 1 mg might be used to immunize a rabbit. For identifying mouse hybridomas, the denatured protein is radioiodinated and used to screen potential murine B-cell hybridomas for those which produce antibody. This procedure requires only small quantities of protein, such that 20 mg is sufficient for labeling and screening of several thousand clones.

In the second approach, the amino acid sequence of an appropriate LTBP2 domain, as deduced from translation of the cDNA, is analyzed to determine regions of high antigenicity. Oligopeptides comprising appropriate hydrophilic regions are synthesized and used in suitable immunization protocols to raise antibodies. The optimal amino acid sequences for immunization are usually at the C-terminus, the N-terminus and those intervening, hydrophilic regions of the polypeptide which are likely to be exposed to the external environment when the protein is in its natural conformation.

Typically, selected peptides, about 15 residues in length, are synthesized using an Applied Biosystems Peptide Synthesizer Model 431A using fmoc-chemistry and coupled to keyhole limpet hemocyanin (KLH; Sigma, St. Louis, Mo.) by reaction with M-maleimidobenzoyl-N-hydroxy-succinimide ester, MBS. If necessary, a cysteine is introduced at the N-terminus of the peptide to permit coupling to KLH. Rabbits are immunized with the peptide-KLH complex in complete Freund's adjuvant. The resulting antisera are tested for antipeptide activity by binding the peptide to plastic, blocking with 1% bovine serum albumin, reacting with antisera, washing and reacting with labeled (radioactive or fluorescent), affinity purified, specific goat anti-rabbit IgG.

Hybridomas are prepared and screened using standard techniques. Hybridomas of interest are detected by screening with labeled LTBP2 to identify those fusions producing the monoclonal antibody with the desired specificity. In a typical protocol, wells of plates (FAST; Becton-Dickinson, Palo Alto, Calif.) are coated during incubation with affinity purified, specific rabbit anti-mouse (or suitable antispecies 1 g) antibodies at 10 mg/ml. The coated wells are blocked with 1% bovine serum albumin, (BSA), washed and incubated with supernatants from hybridomas. After washing the wells are incubated with labeled LTBP2 at 1 mg/ml. Supernatants with specific antibodies bind more labeled LTBP2 than is detectable in the background. Then clones producing specific antibodies are expanded and subjected to two cycles of cloning at limiting dilution. Cloned hybridomas are injected into pristane-treated mice to produce ascites, and monoclonal antibody is purified from mouse ascitic fluid by affinity chromatography on Protein A. Monoclonal antibodies with affinities of at least $10^8 M^{-1}$, preferably $10^9$ to $10^{10} M^{-1}$ or stronger, are typically made by standard procedures.

Example 7:

Diagnostic Test Using LTBP2 Specific Antibodies

Particular LTBP2 antibodies are useful for investigating signal transduction and the diagnosis of infectious or hereditary conditions which are characterized by differences in the amount or distribution of LTBP2 or downstream products of an active signaling cascade.

Diagnostic tests for LTBP2 include methods utilizing antibody and a label to detect LTBP2 in human body fluids, membranes, cells, tissues or extracts of such. The polypeptides and antibodies of the present invention are used with or without modification. Frequently, the polypeptides and antibodies are labeled by joining them, either covalently or non-covalently, with a substance which provides for a detectable signal. A wide variety of labels and conjugation techniques are known and have been reported extensively in both the scientific and patent literature. Suitable labels include radionuclides, enzymes, substrates, cofactors, inhibitors, fluorescent agents, chemiluminescent agents, chromogenic agents, magnetic particles and the like.

A variety of protocols for measuring soluble or membrane-bound LTBP2, using either polyclonal or monoclonal antibodies specific for the protein, are known in the art. Examples include enzyme-linked immunosorbent assay (ELISA), radioimmunoassay (RIA) and fluorescent activated cell sorting (FACS). A two-site monoclonal-based immunoassay utilizing monoclonal antibodies reactive to two non-interfering epitopes on LTBP2 is preferred, but a competitive binding assay may be employed.

Example 8:

Purification of Native LTBP2 Using Specific Antibodies

Native or recombinant LTBP2 is purified by immunoaffinity chromatography using antibodies specific for LTBP2. In general, an immunoaffinity column is constructed by covalently coupling the anti-TRH antibody to an activated chromatographic resin.

Polyclonal immunoglobulins are prepared from immune sera either by precipitation with ammonium sulfate or by purification on immobilized Protein A (Pharmacia LKB Biotechnology, Piscataway N.J.). Likewise, monoclonal antibodies are prepared from mouse ascites fluid by ammonium sulfate precipitation or chromatography on immobilized Protein A. Partially purified immunoglobulin is covalently attached to a chromatographic resin such as CnBr-activated Sepharose (Pharmacia LKB Biotechnology). The antibody is coupled to the resin, the resin is blocked, and the derivative resin is washed according to the manufacturer's instructions.

Such immunoaffinity columns are utilized in the purification of LTBP2 by preparing a fraction from cells containing LTBP2 in a soluble form. This preparation is derived by solubilization of whole cells or of a subcellular fraction obtained via differential centrifugation (with or without addition of detergent) or by other methods well known in the art. Alternatively, soluble LTBP2 containing a signal sequence is secreted in useful quantity into the medium in which the cells are grown.

A soluble LTBP2-containing preparation is passed over the immunoaffinity column, and the column is washed under conditions that allow the preferential absorbance of LTBP2 (e.g., high ionic strength buffers in the presence of detergent). Then, the column is eluted under conditions that disrupt antibody/protein binding (e.g., a buffer of pH 2-3 or a high concentration of a chaotrope such as urea or thiocyanate ion), and LTBP2 is collected.

Example 9:

Drug Screening

This invention is particularly useful for screening therapeutic compounds by using LTBP2 or fragments thereof in any of a variety of drug screening techniques.

The following example provides a system for drug screening measuring LTBP2.

The recombinant protein-His fusion protein can be purified from the crude lysate by metal-affinity chromatography using Ni-NTA agarose. This allows the specific retention of the recombinant material (since this is fused to the His-tag) whilst the endogenous insect proteins are washed off. The recombinant material is then eluted by competition with imidazol.

LTBP2 protein expression in tissues, tissue homogenates and body fluids including plasma and serum can be measured by antibody-based strategies, e.g. by ELISA technology or Western Blotting/Immunofluorescence. A polyclonal antibody generated against the full-length LTBP2 has been described in the literature [Vehvilainen et al. (2003)].

Example 10:

Rational Drug Design

The goal of rational drug design is to produce structural analogs of biologically active polypeptides of interest or of small molecules with which they interact, agonists, antagonists, or inhibitors. Any of these examples are used to fashion drugs which are more active or stable forms of the polypeptide or which enhance or interfere with the function of a polypeptide in vivo.

In one approach, the three-dimensional structure of a protein of interest, or of a protein-inhibitor complex, is determined by x-ray crystallography, by computer modeling or, most typically, by a combination of the two approaches. Both the shape and charges of the polypeptide must be ascertained to elucidate the structure and to determine active site(s) of the molecule. Less often, useful information regarding the structure of a polypeptide is gained by modeling based on the structure of homologous proteins. In both cases, relevant structural information is used to design efficient inhibitors. Useful examples of rational drug design include molecules which have improved activity or stability or which act as inhibitors, agonists, or antagonists of native peptides.

It is also possible to isolate a target-specific antibody, selected by functional assay, as described above, and then to solve its crystal structure. This approach, in principle, yields a pharmacore upon which subsequent drug design is based. It is possible to bypass protein crystallography altogether by generating anti-idiotypic antibodies (anti-ids) to a functional, pharmacologically active antibody. As a mirror image of a mirror image, the binding site of the anti-ids is expected to be an analog of the original receptor. The anti-id is then used to identify and isolate peptides from banks of chemically or biologically produced peptides. The isolated peptides then act as the pharmacore.

By virtue of the present invention, sufficient amount of polypeptide are made available to perform such analytical studies as X-ray crystallography. In addition, knowledge of the LTBP2 amino acid sequence provided herein provides guidance to those employing computer modeling techniques in place of or in addition to x-ray crystallography.

Example 11:

Identification of Other Members of the Signal Transduction Complex

Labeled LTBP2 is useful as a reagent for the purification of molecules with which it interacts. In one embodiment of affinity purification, LTBP2 is covalently coupled to a chromatography column. Cell-free extract derived from synovial cells or putative target cells is passed over the column, and molecules with appropriate affinity bind to LTBP2. LTBP2-complex is recovered from the column, and the LTBP2-binding ligand disassociated and subjected to N-terminal protein sequencing. The amino acid sequence information is then used to identify the captured molecule or to design degenerate oligonucleotide probes for cloning the relevant gene from an appropriate cDNA library.

In an alternate method, antibodies are raised against LTBP2, specifically monoclonal antibodies. The monoclonal antibodies are screened to identify those which inhibit the binding of labeled LTBP2. These monoclonal antibodies are then used therapeutically.

Example 12:

Use and Administration of Antibodies, Inhibitors, or Antagonists

Antibodies, inhibitors, or antagonists of LTBP2 or other treatments and compounds that are limiters of signal transduction (LSTs), provide different effects when administered therapeutically. LSTs are formulated in a nontoxic, inert, pharmaceutically acceptable aqueous carrier medium preferably at a pH of about 5 to 8, more preferably 6 to 8, although pH may vary according to the characteristics of the antibody, inhibitor, or antagonist being formulated and the condition to be treated. Characteristics of LSTs include solubility of the molecule, its half-life and antigenicity/immunogenicity. These and other characteristics aid in defining an effective carrier. Native human proteins are preferred as LSTs, but organic or synthetic molecules resulting from drug screens are equally effective in particular situations.

LSTs are delivered by known routes of administration including but not limited to topical creams and gels; transmucosal spray and aerosol; transdermal patch and bandage; injectable, intravenous and lavage formulations; and orally administered liquids and pills particularly formulated to resist stomach acid and enzymes. The particular formulation, exact dosage, and route of administration is determined by the attending physician and varies according to each specific situation.

Such determinations are made by considering multiple variables such as the condition to be treated, the LST to be administered, and the pharmacokinetic profile of a particular LST. Additional factors which are taken into account include severity of the disease state, patient's age, weight, gender and diet, time and frequency of LST administration, possible combination with other drugs, reaction sensitivities, and tolerance/response to therapy. Long acting LST formulations might be administered every 3 to 4 days, every week, or once every two weeks depending on half-life and clearance rate of the particular LST.

Normal dosage amounts vary from 0.1 to $10^5$ µg, up to a total dose of about 1 g, depending upon the route of administration. Guidance as to particular dosages and methods of delivery is provided in the literature; see U.S. Pat. No. 4,657,760; 5,206,344; or 5,225,212. Those skilled in the art employ different formulations for different LSTs. Administration to cells such as nerve cells necessitates delivery in a manner different from that to other cells such as vascular endothelial cells.

It is contemplated that abnormal signal transduction, trauma, or diseases which trigger LTBP2 activity are treatable with LSTs. These conditions or diseases are specifically diagnosed by the tests discussed above, and such testing should be performed in suspected cases of viral, bacterial or fungal infections, allergic responses, mechanical injury associated with trauma, hereditary diseases, lymphoma or carcinoma, or other conditions which activate the genes of lymphoid or neuronal tissues.

Example 13:

Production of Non-human Transgenic Animals

Animal model systems which elucidate the physiological and behavioral roles of the LTBP2 are produced by creating nonhuman transgenic animals in which the activity of the LTBP2 is either increased or decreased, or the amino acid sequence of the expressed LTBP2 is altered, by a variety of techniques. Examples of these techniques include, but are not limited to: 1) Insertion of normal or mutant versions of DNA encoding a LTBP2, by microinjection, electroporation, retroviral transfection or other means well known to those skilled in the art, into appropriately fertilized embryos in order to produce a transgenic animal or 2) homologous recombination of mutant or normal, human or animal versions of these genes with the native gene locus in transgenic animals to alter the regulation of expression or the structure of these LTBP2 sequences. The technique of homologous recombination is well known in the art. It replaces the native gene with the inserted gene and hence is useful for producing an animal that cannot express native LTBP2s but does express, for example, an inserted mutant LTBP2, which has replaced the native LTBP2 in the animal's genome by recombination, resulting in underexpression of the transporter. Microinjection adds genes to the genome, but does not remove them, and the technique is useful for producing an animal which expresses its own and added LTBP2, resulting in overexpression of the LTBP2.

One means available for producing a transgenic animal, with a mouse as an example, is as follows: Female mice are mated, and the resulting fertilized eggs are dissected out of their oviducts. The eggs are stored in an appropriate medium such as cesiumchloride M2 medium. DNA or cDNA encoding LTBP2 is purified from a vector by methods well known to the one skilled in the art. Inducible promoters may be fused with the coding region of the DNA to provide an experimental means to regulate expression of the transgene. Alternatively or in addition, tissue specific regulatory elements may be fused with the coding region to permit tissue-specific expression of the transgene. The DNA, in an appropriately buffered solution, is put into a microinjection needle (which may be made from capillary tubing using a piper puller) and the egg to be injected is put in a depression slide. The needle is inserted into the pronucleus of the egg, and the DNA solution is injected. The injected egg is then transferred into the oviduct of a pseudopregnant mouse which is a mouse stimulated by the appropriate hormones in order to maintain false pregnancy, where it proceeds to the uterus, implants, and develops to term. As noted above, microinjection is not the only method for inserting DNA into the egg but is used here only for exemplary purposes.

Example 14:

Use of LTBP2 as a Biomarker, Therapeutic and Diagnostic Target in Cardiovascular Disease (DOCA)

The DOCA-salt hypertensive rat model is a well established model of left ventricular hypertrophy.

Uninephrectomized male Sprague-Dawley rats weighing 300-350 g were given 1% NaCl in drinking water and subcutaneous injections of deoxycorticosterone acetate (DOCA, 30 mg/kg once weekly) for four weeks. Untreated rats without uninephrectomy served as control rats.

After four weeks DOCA-salt rats showed a significant increase in the tibia length-corrected left ventricular mass (DOCA-salt: 25.87±0.84 mg/mm vs. control: 21.03±0.60 mg/mm). At this time point heart and Li-Heparin plasma samples were taken for expression analysis.

Total cellular RNA was isolated with the Trizol-Reagent protocol according to the manufacturer's specifications (Invitrogen; USA). Total RNA prepared by the Trizol-reagent protocol was treated with DNAse I to remove genomic DNA contamination.

For relative quantitation of the mRNA distribution of LTBP2, total RNA from each sample was first reverse transcribed. 1 µg of total RNA was reverse transcribed using ImProm-II Reverse Transcription System (Promega, USA) according to the manufactures protocol. The final volume was adjusted to 200 µl with water.

For relative quantitation of the distribution of LTBP2 mRNA the Applied Bioscience ABI 7900HT Sequence Detection system was used according to the manufacturer's specifications and protocols. PCR reactions were set up to quantitate LTBP2 and the housekeeping gene L32. Forward and reverse primers and probes for LTBP2 were designed using the Applied Bioscience ABI Primer Express™ software and were synthesized by Eurogentec (Belgium). The LTBP2 forward primer sequence was: Primer1 (SEQ ID NO: 5). The LTBP2 reverse primer sequence was Primer2 (SEQ ID NO: 7). Probe1 (SEQ ID NO: 6), labelled with FAM (carboxyfluorescein succinimidyl ester) as the reporter dye and TAMRA (carboxytetramethylrhodamine) as the quencher, is used as a probe for LTBP2. The following reagents were prepared in a total of 20 µl: 1×qPCR-MasterMix (Eurogentec; Belgium) and Probe1 (SEQ ID NO: 6), LTBP2 forward and reverse primers each at 200 nM, 200 nM LTBP2 FAM/TAMRA-labelled probe, and 5 µl of template cDNA. Thermal cycling parameters were 2 min at 50° C., followed by 10 min at 95° C., followed by 40 cycles of melting at 95° C. for 15 sec and annealing/extending at 60° C. for 1 min.

Calculation of Relative Expression

The CT (threshold cycle) value is calculated as described in the "Quantitative determination of nucleic acids" section.

$$deltaCT = CT_{LTBP2} - CT_{L32}$$

$$relative\ expression = 2^{(15-deltaCT)}$$

The results of the mRNA-quantification (expression profiling) is shown in FIG. 11.

Example 15:

Use of LTBP2 as a Biomarker, Therapeutic and Diagnostic Target in Cardiovascular Disease (Occlusion)

In the chronic myocardial infarction model in rat [Pfeffer et al, (1979)] left coronary artery ligation is performed under isoflurane anaesthesia. Following a left thoractomy at the fourth intercostal space, the pericardium is opened and the heart briefly exteriorized. The left coronary artery (LAD) is chronically ligated. In sham operated animals the LAD stays open. The chest is closed and animals are weaned from the ventilator and placed in cages with free access to food and water. One week after LAD occlusion application of test compounds is started. Heart tissue and plasma samples are analyzed 9 weeks after induction of the infarct towards plasma markers and expression profiles.

Total cellular RNA was isolated with the Trizol-Reagent protocol according to the manufacturer's specifications (Invitrogen; USA). Total RNA prepared by the Trizol-reagent protocol was treated with DNAse I to remove genomic DNA contamination.

For relative quantitation of the mRNA distribution of LTBP2, total RNA from each sample was first reverse transcribed. 1 µg of total RNA was reverse transcribed using ImProm-II Reverse Transcription System (Promega, USA) according to the manufactures protocol. The final volume was adjusted to 200 µl with water.

For relative quantitation of the distribution of LTBP2 mRNA the Applied Bioscience ABI 7900HT Sequence Detection system was used according to the manufacturer's specifications and protocols. PCR reactions were set up to quantitate LTBP2 and the housekeeping gene L32. Forward and reverse primers and probes for LTBP2 were designed using the Applied Bioscience ABI Primer Express™ software and were synthesized by Eurogentec (Belgium). The LTBP2 forward primer sequence was: Primer1 (SEQ ID NO: 5). The LTBP2 reverse primer sequence was Primer2 (SEQ ID NO: 7). Probe1 (SEQ ID NO: 6), labelled with FAM (carboxyfluorescein succinimidyl ester) as the reporter dye and TAMRA (carboxytetramethylrhodamine) as the quencher, is used as a probe for LTBP2. The following reagents were prepared in a total of 20 µl: 1×qPCR-MasterMix (Eurogentec; Belgium) and Probe1 (SEQ ID NO: 6), LTBP2 forward and reverse primers each at 200 nM, 200 nM LTBP2 FAM/TAMRA-labelled probe, and 5 µl of template cDNA. Thermal cycling parameters were 2 min at 50° C., followed by 10 min at 95° C., followed by 40 cycles of melting at 95° C. for 15 sec and annealing/extending at 60° C. for 1 min.

Calculation of Relative Expression

The CT (threshold cycle) value is calculated as described in the "Quantitative determination of nucleic acids" section.

$$deltaCT = CT_{LTBP2} - CT_{L32}$$

$$relative\ expression = 2^{(15-deltaCT)}$$

The results of the mRNA-quantification (expression profiling) is shown in FIG. 12.

Example 16:

Use of LTBP2 as a Biomarker, Therapeutic and Diagnostic Target in Cardiovascular Disease (Monocrotalin)

Adult male Sprague-Dawley rats weighing 250 to 300 g were given a single subcutaneous injection of either 60 mg/kg Monocrotaline or vehicle.

The Monocrotaline (MCT)-treated rat is a widely used animal model for pulmonary arterial hypertension. After subcutaneous injection the pyrrolizidine alkaloid MCT is activated by the liver to the toxic MCT pyrrole, which causes endothelial injury in the pulmonary vasculature within few days with subsequent remodeling of small pulmonary arteries (de novo muscularization and medial hypertrophy). In the present study, MCT induced severe, progressive pulmonary hypertension in all animals.

Four weeks after a single MCT injection, the rats displayed threefold elevated right ventricular systolic pressure (placebo MCT: 77.62±4.17 mmHg vs. control: 26.4±1.12 mmHg; mean±sem), accompanied by a reduction of systemic arterial pressure, cardiac index, arterial oxygenation and central venous oxygen saturation. In accordance with these results, an impressive right heart hypertrophy was observed (right ventricle/left ventricle+septum ratio placebo MCT: 0.62±0.03 vs. control: 0.26±0.01).

Heart and Li-Heparin plasma samples were taken for expression analysis four weeks after the MCT injection.

Total cellular RNA was isolated with the Trizol-Reagent protocol according to the manufacturer's specifications (Invitrogen; USA). Total RNA prepared by the Trizol-reagent protocol was treated with DNAse I to remove genomic DNA contamination.

For relative quantitation of the mRNA distribution of LTBP2, total RNA from each sample was first reverse transcribed. 1 µg of total RNA was reverse transcribed using ImProm-II Reverse Transcription System (Promega, USA) according to the manufactures protocol. The final volume was adjusted to 200 µl with water.

For relative quantitation of the distribution of LTBP2 mRNA the Applied Bioscience ABI 7900HT Sequence Detection system was used according to the manufacturer's specifications and protocols. PCR reactions were set up to quantitate LTBP2 and the housekeeping gene L32. Forward and reverse primers and probes for LTBP2 were designed using the Applied Bioscience ABI Primer Express™ software and were synthesized by Eurogentec (Belgium). The LTBP2 forward primer sequence was: Primer1 (SEQ ID NO: 5). The LTBP2 reverse primer sequence was Primer2 (SEQ ID NO: 7). Probe1 (SEQ ID NO: 6), labelled with FAM (carboxyfluorescein succinimidyl ester) as the reporter dye and TAMRA (carboxytetramethylrhodamine) as the quencher, is used as a probe for LTBP2. The following reagents were prepared in a total of 20 µl: 1× qPCR-MasterMix (Eurogentec; Belgium) and Probe1 (SEQ ID NO: 6), LTBP2 forward and reverse primers each at 200 nM, 200 nM LTBP2 FAM/TAMRA-labelled probe, and 5 µl of template cDNA. Thermal cycling parameters were 2 min at 50° C., followed by 10 min at 95° C., followed by 40 cycles of melting at 95° C. for 15 sec and annealing/extending at 60° C. for 1 min.

Calculation of Relative Expression

The CT (threshold cycle) value is calculated as described in the "Quantitative determination of nucleic acids" section.

$$deltaCT = CT_{LTBP2} - CT_{L32}$$

$$relative\ expression = 2^{(15-deltaCT)}$$

The results of the mRNA-quantification (expression profiling) is shown in FIG. 13.

Example 17:

Microarray Experiments

Total RNA extracted from cardiac tissue and was purified using an affinity resin column (RNeasy; Qiagen, Hilden, Germany), quantified by spectrophotometry (absorbance 260 nm), and the quality of RNA was assessed by microfluidics electrophoretical separation with a Bioanalyzer (Agilent Technologies, Palo Alto, USA). Purified total RNA (1 µg) was converted to cDNA using the Superscript Choice cDNA synthesis kit (Invitrogen, Carlsbad, Calif., USA), incorporating a T7-(dT)24 primer. Double-stranded cDNA was then purified by affinity resin column (Clean up Kit, Qiagen, Hilden, Germany) with ethanol extraction. Purified cDNA was used as a template for in vitro transcription reaction for the synthesis of biotinylated cRNA using an Enzo BioArray HighYield RNA transcription labeling kit (Affymetrix, Santa Clara, Calif.), and further purified using an affinity resin column (Clean up Kit, Qiagen, Hilden, Germany). After purification, in vitro cRNA was fragmented in buffer containing magnesium at 95° C. for 35 min. Fragmented cRNA was hybridized onto the Affymetrix GeneChip Human Genome U133 Plus 2.0 Array. Briefly, 15 µg fragmented cRNA was added along with control cRNA (BioB, BioC, and BioD), herring sperm DNA (10 mg/ml), 10% DMSO, and acetylated BSA (50 mg/ml) to the hybridization buffer. The hybridization mixture was heated at 99° C. for 5 min, incubated at 45° C. for 5 min, centrifuged for 5 min at 13.000 rpm, and injected into the microarray. After hybridization at 45° C. for 16 h rotating at 60 rpm, the array was washed and stained with the Affymetrix Fluidics Protocols-antibody amplification for Eukaryotic Targets, and scanned using an Affymetrix microarray scanner (GeneChip Scanner 3000 7G system) at 570 nm.

Example 18:

Microarray Expression Data From Human Heart of CHF Patients With Left Ventricular Assist Devices Implantation of left ventricular assist devices (LVAD) often is the only possible means of supporting patients with end-stage heart failure in the form of bridging to transplantation (see [Clegg et al. (2005)] for a review). Like the heart, the LVAD is a pump. One end hooks up to the left ventricle— that's the chamber of the heart that pumps blood out of the lungs and into the body. The other end hooks up to the aorta, the body's main artery. A tube passes from the device through the skin. The outside of the tube is covered with a special material to aid in healing and allow the skin to regrow. The LVAD is implanted during open-heart surgery. Recent reports demonstrate that LVAD support may be associated with adaptive remodeling of the ventricular myocardium, including reduced LV mass, wall thickness and myocyte diameter, changes in LV pressure-volume relationships and reversal of LV chamber dilation [Li et al. (2001)].

Myocardial samples of the left ventricle were collected during cardiac surgery from 32 heart failure patients at the time of cardiac transplantation or insertion of a mechanical assist device. Corresponding myocardial specimen are designed as pre- and post-LVAD samples. All procedures involving human tissue use were approved by the institutional review boards of the 'Heart- and Diabetes-Center North Rhine Westphalia, Bad Oeynhausen, Germany. Consent was obtained from patients before tissue harvest. Samples were immediately frozen in liquid nitrogen and pulverized using pestle and mortar. Total RNA was isolated according to standard procedures.

Example 19:

Data Analysis From Microarray Experiments

Raw data analysis and scaling were performed in Microarray Suite 5.0 software (Affymetrix), and normalization and further analysis in expressionist Pro 3.0 (Genedata). Results for HG-U133 Plus 2.0 arrays were subjected to global scaling with a target intensity of 100.

Base-2 logarithms were calculated for all expression values and taken for subsequent statistical analysis. To analyze the differential expression between the two groups, non-failing hearts (N) and pre-operation hearts (P), a two-tailed Student's test was applied to the expression values under the assumption of equal variances. A resultant p-value of less or equal than 0.05 was taken as indicator for significant differential expression.

REFERENCES

EP 1 069 188
EP 1 275 733
EP 1 308 459
EP 1 560 025
EP 1 612 281
U.S. Pat. No. 4,522,811
U.S. Pat. No. 5,057,414
U.S. Pat. No. 5,283,317
U.S. Pat. No. 5,565,332
U.S. Pat. No. 5,723,323.
U.S. Pat. No. 5,747,334
U.S. Pat. No. 5,783,384
U.S. Pat. No. 5,885,814
U.S. Pat. No. 5,985,629
WO 84/03564
WO 93/03151
WO 94/13804
WO 00/47750
WO 02/06492
WO 02/26958
WO 02/47670
WO 03/051370
WO 02/081745
WO 2004075835
WO 02068579
Altschul S F, Madden T L, Schaffer A A, Zhang J, Zhang Z, Miller W, Lipman D J; Nucleic Acids Res 1997 Sep. 1; 25(17): 3389-402
Appa Rao et al., 1997, Protein Expr Purif November, 11(2): 201-8
Alpert, J. S., et al. J. Am. Coll. Cardiol. 2000; 36:959-69
Avalle et al., Ann. N Y Acad. Sci. 864:118 (1998)).
Barnes, 2000, Chest, 117:10S14S
Barrett et al., (Eds.), Handbook of Proteolytic Enzymes (Academic Press Inc. 1998).
Barrett (Ed.), Methods in Enzymology, Proteolytic Enzymes: Serine and Cysteine Peptidases (Academic Press Inc. 1994)
Boersma, E., et al. Lancet 2002; 359:189-98
Botstein et al., 1980, Am J Hum Genet. 32: 314-31
Clegg et al. 2005, Health Technol Assess. November; 9(45): 1-148
Colbere-Garapin et al., 1981, *J. Mol. Biol.* 150, 1-14
Christenson, R. H., et al., Clin. Chem. 2001; 47:464-470
Cunningham and Wells, J. Mol. Biol. 234:554 (1993).
DesGroseillers et al. (2001), DNA Cell Biol. August; 20(8): 493-8.
de Lemos, J. A., et al. J. Am. Coll. Cardiol. 2002; 40:238-44
Duveneck G. L. et al, Analytica Chimica Acta 469 (2002), 49-61.
Engelhard et al., 1994, *Proc. Nat. Acad. Sci.* 91, 3224-3227
Friboulet et al., Appl. Biochem. Biotechnol. 47:229 (1994)
Gergen and Weiss, 1992, Am Rev Respir Dis 146:823-824
Gibson et al., 1996, Genome Research 6: 995-1001
Haseloff et al., 1988, *Nature* 334, 585-591
Heid et al., 1996, Genome Research 6: 986-994
Holland et al., 1991, PNAS 88: 7276-7280
Ifon et al. 2005, Cancer Cell Int. June 22; 5:19.
Jeffreys et al., 1985, Nature 316: 76-9
Johnson et al., 1989, *Endoc. Rev.* 10, 317-331
Joron et al., Ann. N Y Acad. Sci. 672:216 (1992)
Karlsson, Immunol. Methods 145:229 (1991)
Kellogg et al., 1990, Anal. Biochem. 189:202-208
Lam, 1997, Anticancer Drug Res. 12(3):145-67
Li et al. 2001, Circulation. September 4; 104(10):1147-52
Livak et al., 1995, PCR Methods and Applications 357-362
Logan, Shenk, 1984, *Proc. Natl. Acad. Sci.* 81, 3655-3659
Lowy et al., 1980, *Cell* 22, 817-23
Maddox et al., 1983, *J. Exp. Med.* 158, 1211-1216
Monfardini et al., Proc. Assoc. Am. Physicians 108:420 (1996)
McConnell et al., 1992, *Science* 257, 1906-1912
Nicholls et al., 1993, *J. Immunol. Meth.* 165, 81-91
Newby, L. K., et al. Circulation 2001:103; 1832-7
Pawlak M. et al, Proteomics 2(4) (2002), 383-393

Pentecost et al. 2005, Mol Cell Endocrinol. June 30; 238(1-2):9-25.
Piatak et al., 1993, BioTechniques 14:70-81
Piatak et al., 1993, Science 259:1749-1754
Porath et al., 1992, *Prot. Exp. Purif* 3, 263-281
Pfeffer et al., Circ Res. 1979 April; 44(4):503-12.
Roberge et al., 1995, *Science* 269, 202-204
Sagnella, G. A., Clinical Science 95:519-529, 1998
Scott and Smith (1990) Science 249:386-390
Sjolander, Urbaniczky, 1991, *Anal. Chem.* 63, 2338-2345
Szabo et al., 1995, Curr. Opin. Struct. Biol. 5, 699-705
Thomas, 1980, Proc. Nat. Acad. Sci., 77:5201-5205
Uhlmann et al., 1987, *Tetrahedron. Lett.* 215, 3539-3542
Weber et al., 1990, Genomics 7: 524-30
Wigler et al., 1977, *Cell* 11, 223-32
Wigler et al., 1980, *Proc. Natl. Acad. Sci.* 77, 3567-70
Oklu R, Hesketh R., 2000, Biochem J. December 15; 352 Pt 3:601-10.
Saharinen J, Keski-Oja J. 2000, Mol Biol Cell. August; 11(8): 2691-704
Vehvilainen P, Hyytiainen M, Keski-Oja, 2003, J Biol Chem. July 4; 278(27):24705-13.
Hyytiainen M, Keski-Oja J. R 2003, J Cell Biol. December 22; 163(6):1363-74.
Shipley J M, Mecham R P, Maus E, Bonadio J, Rosenbloom J, McCarthy R T, Baumann M L, Frankfater C, Segade F, Shapiro S D, 2000, Mol Cell Biol. July; 20(13):4879-87.
Sinha S, Heagerty A M, Shuttleworth C A, Kielty C M., 2002, Cardiovasc Res. March; 53(4):971-83.
Watkins S J, Jonker L, Arthur H M., 2006, Cardiovasc Res. February 1; 69(2):432-9.

The invention claimed is:

1. A method of using latent TGFβ binding protein 2 (LTBP2) as a biomarker for heart failure, comprising:
   (i) measuring the level of LTBP2 mRNA in a heart tissue sample obtained from a mammal,
   (ii) comparing the level of LTBP2 mRNA in the heart tissue sample with the level of LTBP2 mRNA in a control sample, and
   (iii) diagnosing heart failure based upon the LTBP2 mRNA level of the heart tissue sample in comparison to the control sample,
   wherein an increase in the level of LTBP2 mRNA in the heart tissue sample compared to the level of LTBP2 mRNA in the control sample indicates a diagnosis of heart failure.

2. The method of claim 1 wherein the mammal is a human.

3. The method of claim 1 further comprising measuring a level of one or more additional biomarkers.

4. The method of claim 1 further comprising assessing one or more clinical biomarkers which are selected from the group consisting of blood pressure, heart rate, pulmonary artery pressure, and systemic vascular resistance.

* * * * *

SEQUENCE LISTING

<160> NUMBER OF SEQ ID NOS: 10

<210> SEQ ID NO 1
<211> LENGTH: 7017
<212> TYPE: DNA
<213> ORGANISM: Homo sapiens

<400> SEQUENCE: 1

```
cctcgctccc tctccggtaa tgagggggct gagctgtccc tccgaggagg gggcctggtg      60
tggataaaag agacgaaaaa gccggggggag gtttccaaaa ataaaaccgt ccgggtcccc     120
ttcagacggc tgcaggcaca gggaggaggc gcgaaggtgc agcagccgtg cgagcccagc     180
tggagtagga gcgcggactc gaggctcggg gcgcgcagcc ctcgttccgc cgagagccgg     240
gcccccagtc ggccgcttca gggcccccta gactcagaga agctggccgc cgggcggggc     300
cgggagaaca gcccgcgggc gtccagcgtg ccgaccacaa agctcttcgc ggtgcccgcg     360
cgcaccactc tccagccgcc ccgcgccatg aggccgcgga ccaaagcccg cagcccgggg     420
cgcgccctgc ggaacccctg gagaggcttc ctgccgctca ccctggctct cttcgtgggc     480
gcgggtcatg cccaaaggga ccccgtaggg agatacgagc cggctggtgg agacgcgaat     540
cgactgcggc gccctggggg cagctacccg gcagcggctg cagccaaggt gtacagtctg     600
ttccgggagc aggacgcgcc tgtcgcgggc ttgcagcccg tggagcgggc ccagccgggc     660
tgggggagcc ccaggaggcc caccgaggcg gaggccagga ggccgtcccg cgcgcagcag     720
tcgcggcgtg tccagccacc tgcgcagacc cggagaagca ctccctggg ccagcagcaa     780 ccagcacccc ggacccgggc cgcgccggct ctcccacgcc tggggacccc acagcggtct     840
ggggctgcgc ccccaacccc gccgcgaggg cggctcacgg ggaggaacgt ctgcggggga     900
cagtgctgcc caggatggac aacagcaaac agcaccaacc actgtatcaa acccgtttgc     960
gagccgccgt gccagaaccg gggctcctgc agccgcccgc agctctgtgt ctgccgctct    1020
ggtttccgtg gagcccgctg cgaggaggtc attcccgatg aggaatttga ccccccagaac    1080 tccaggctgg cacctcgacg ctgggccgag cgttcaccca acctgcgcag gagcagtgcg    1140
gctggagagg gcaccttggc cagagcacag ccgccagcac cacagtcgcc gcccgcacca    1200
cagtcgccac cagctgggac cctgagtggc ctcagccaga cccaccccttc ccagcagcac    1260 gtggggttgt cccgcactgt ccgacttcac ccgactgcca cggccagtag ccagctctct    1320
tccaacgccc tgccccgggg accaggcctt gagcagagag atggcaccca acaggcgta     1380 cctctggagc acccctcatc cccctggggg ctgaacctca cggagaaaat caagaagatc    1440
```

```
aagatcgtct tcactcccac catctgcaag cagacctgtg cccgtggaca ctgtgccaac    1500
agctgtgaga ggggcgacac caccaccctg tacagccagg gcggccatgg gcacgatccc    1560
aagtctggct tccgcatcta tttctgccag atcccctgcc tgaacggagg ccgctgcatc    1620
ggcagggacg aatgctggtg ccccgccaac tccaccggga agttctgcca cctgcctatc    1680
ccgcagccgg acaggagcc tccagggagg ggtcccgcc ccagggcctt gctggaagcc    1740
ccactgaagc agtccacttt cacactgccg ctctccaacc agctggcctc cgtgaacccc    1800
tccctggtga aggtgcacat tcaccaccca cccgaggcct cagtgcagat ccaccaggtg    1860
gcccaggtgc ggggcggggt ggaggaggcc ctagtggaga acagcgtgga gaccagaccc    1920
ccgccctggc tgcctgccag ccctggccac agcctctggg acagcaacaa catccctgct    1980
cggtctggag agccccctcg gccactgccc ccagcagcac ccaggcctcg aggactgctg    2040
ggccggtgtt acctgaacac tgtgaacgga cagtgtgcca ccctctgct ggagctgact    2100 acccaggagg actgctgtgg cagtgtggga gccttctggg gggtgacttt gtgtgcccca    2160
tgcccaccca gaccagcctc cccggtgatt gagaatggcc agctggagtg tcctcagggg    2220
tacaagagac tgaacctcac tcactgccaa gatatcaacg agtgcttgac cctgggcctg    2280
tgcaaggacg cggagtgtgt gaataccagg ggcagctacc tgtgcacatg cagacctggc    2340
ctcatgctgg atccatcgcg gagccgctgt gtgtcggaca aggcaatctc catgctgcag    2400
ggactgtgct accggtcgct ggggcccggc acctgcaccc tgcctttggc ccagcggatc    2460
accaagcaga tatgctgctg cagccgcgtg ggcaaagcat ggggcagcga gtgtgagaaa    2520
tgccctctgc ctggcacaga ggccttcaga gagatctgcc ctgccggcca cggctacacc    2580
tacgcgagct ccgacatccg cctgtccatg aggaaagccg aggaggagga actggcaagg    2640
cccccaaggg agcaagggca gaggagcagc ggggcactgc ccgggccagc agagaggcag    2700
cccctccggt tcgtcacgga cacctggctt gaggccggga ccatccctga caagggtgac    2760
tctcaggctg ccaggtcac gaccagtgtc actcatgcac ctgcctgggt cacagggaat    2820
gccacaaccc caccaatgcc tgaacagggg attgcagaga tacaggaaga caagtgacc    2880 ccctccaccg atgtgctggt gaccctgagc accccaggca ttgacagatg cgctgctgga    2940
gccaccaacg tctgtggccc tggaacctgc gtgaacctcc ccgatggata cagatgtgtc    3000
tgcagccctg gctaccagct gcaccccagc caggcctact gcacagatga caacgagtgt    3060
ctgagggacc cctgcaaggg aaaagggcgc tgcatcaacc gcgtggggtc ctactcctgc    3120
ttctgctacc ctggctacac tctggccacc tcagggcgca cacaggagtg tcaagatatc    3180
aatgagtgtg agcagccagg ggtgtgcagc gggggcagt gcaccaacac cgagggctcg    3240
taccactgcg agtgtgatca gggctacatc atggtcagga aaggacactg ccaagatatc    3300
aacgaatgcc gtcaccccgg tacctgcccc tgatgggaga tgcgtcaattc ccctggctcc    3360 tacacttgtc tggcctgtga ggagggctac cggggccaga gtgggagctg tgtagatgtg    3420
aatgagtgtc tgactcccgg ggtctgtgcc catggaaagt gcaccaacct agaaggctcc    3480
ttcagatgct cttgtgagca gggctatgag gtcacctcag atgagaaggg ctgccaagat    3540
gtggatgagt gtgccagccg ggcctcatgc ccacaggcc tctgcctcaa cacggagggc    3600
tccttcgcct gctctgcctg tgagaacggg tactgggtga tgaagacgg cactgcctgt    3660 gaagacctag atgagtgtgc cttcccggga gtctgccccct ccggagtctg caccaacacg    3720
gctggctcct tctcctgcaa ggactgcgat ggggctacc ggcccagccc cctgggtgac    3780
tcctgtgaag atgtggatga atgtgaagac ccccagcagca gctgcctggg aggcgagtgc    3840
```

```
aagaacactg tgggctccta ccagtgcctc tgtccccagg gcttccagct ggccaatggc    3900
accgtgtgtg aggatgtgaa tgagtgcatg ggggaggagc actgcgcacc ccacggcgag    3960
tgcctcaaca gccacgggtc tttcttctgt ctgtgcgcgc ctggcttcgt cagcgcagag    4020
gggggcacca gctgccagga tgtggacgag tgtgccacca cagacccgtg tgtgggaggg    4080
cactgtgtca acaccgaggg ctccttcaac tgtctatgtg agactggctt ccagccctcc    4140
ccagagagtg gagagtgtgt ggatattgac gagtgtgagg actatggaga cccggtgtgt    4200
ggcacctgga agtgtgaaaa cagccctggc tcctaccgct gtgttctggg ctgccagcct    4260
ggcttccaca tggccccgaa cggagactgc attgacatag acgagtgcgc caacgacacc    4320
atgtgtggca gccacggctt ctgtgacaac actgatggct ccttccgctg cctctgtgac    4380
cagggcttcg agatctctcc ctcaggctgg gactgtgtgg atgtgaacga gtgtgagctt    4440
atgctggcgg tatgtggggc cgcgctctgt gagaacgtgg agggctcctt cctgtgcctc    4500
tgtgccagtg acctggagga gtacgatgcc caggagggga actgccgccc acgggggggct    4560 ggaggtcaga gtatgtctga ggccccaacg ggggaccatg ccccggcccc cacccgcatg    4620
gactgctact ccgggcagaa gggccatgcg ccctgctcca gtgtcctggg ccggaacacc    4680
acacaggctg aatgctgctg cacccagggc gctagctggg gagatgcctg tgacctctgc    4740
ccgtctgagg actcagctga attcagcgag atctgcccta gtggaaaagg ctacattcct    4800
gtggaaggag cctggacgtt tggacagacc atgtacacag atgcggatga gtgtgtgata    4860
ttcgggcctg gtctctgccc gaacggccgg tgcctcaaca ccgtgcctgg ttatgtctgc    4920
ctgtgcaatc ccggcttcca ctacgatgct tcccacaaga agtgtgagga tcacgatgag    4980
tgccaggacc tggcctgtga aatggcgag tgcgtcaaca cggagggctc cttccactgc    5040
ttctgcagcc ccccgctcac cctggacctc agccagcagc gctgcatgaa cagcaccagc    5100
agcacggagg acctccctga ccacgacatc cacatggaca tctgctggaa aaaagtcacc    5160
aatgatgtgt gcagcgaacc cctgcgtggg caccgcacca cctacacgga atgctgctgc    5220
caggacggcg aggcctggag ccagcagtgt gctctgtgtc cccgaggag ctctgaggtc    5280 tatgctcagc tgtgcaacgt ggctcgcatt gaggcagagc gggaggccgg ggtccacttc    5340
cggccaggct atgagtatgg ccccgggccc gatgacctgc actacagcat ctatggccca    5400
gatggggccc ccttctacaa ctacctgggc cccgaggaca ccgtccctga gcctgccttc    5460
cccaacacag ccggtcactc agcggaccgc acacccatcc ttgagtctcc tttgcagccc    5520
tcagaactcc agccccacta cgtggccagc catccagagc ccccagccgg cttcgaaggg    5580
cttcaggcgg aggagtgcgg catcctgaac ggctgtgaga atggccgctg tgtgcgcgtg    5640
cgggagggct acacctgtga ctgttttgag ggcttccagc tggatgcggc ccacatggcc    5700
tgcgtagatg tgaatgagtg tgatgacttg aacgggcctg ctgtgctctg tgtccatggt    5760
tactgcgaga acacagaggg ctcctaccgc tgccactgct ccccgggata tgtggctgag    5820
gcagggcccc cccactgcac tgccaaggag tagcagtcag gggtcagtgt ggcaactacc    5880
tggaaatggc ctccagtcac aggcaggggc cttgaggatg atttcctagc tgggaagaca    5940
ccgtgacatc aggccagagg tttccaatca gccttgcctg ctttcatctc tcccagctta    6000
gcctctggct gtaagcttcg gtcattgcct ccatgccctt gcttggctca agcaccacca    6060
atcgctttaa tgcttcagcc accgcatgag gccctgtcca ccacctttcc tggccttgct    6120
atgggatgct accaaaagga tggccctcat ccaccctccc aagctgtgcg agcatgcaag    6180
gccccatggc ctcacactgc agacaccccct ttccagccac aatccaccat catcctgacg    6240
```

| | |
|---|---|
| atcccacaac tgggacagag gctacatctg ccctagggag gtccttcaga atctgtggag | 6300 |
| caagaaagga tttggggaag cttggggact gactccagag ccccctccta agaaccatca | 6360 |
| ccaccactca gccaatctgt tctgggccct gattttgcca cacctccatc ctgtagccca | 6420 |
| ttctctgacc ccaaggagtg gcagaagatc ccttcactca gagaagcaag gctgatatta | 6480 |
| gcttgttgaa tgtaagagac acaaatgaag aagaacaaag agcctgagaa agcagcaaga | 6540 |
| ggacatgatg aaaaatacgt ggagttgatg agaaagggga gccaaggctt tatacgtcta | 6600 |
| aagaaaatat tcagtagctg aatccgccca gtgatagcct gtgggcacca gcagcaaggg | 6660 |
| ctgccatggg atacagcacc catctacaaa gacctctatt acataaacac tgcttcttac | 6720 |
| aggaaacaaa cctcttctgg gatctccttt tgtgaaaacc agtttgatgt gctaaaagta | 6780 |
| aaaagtctat tttccagtgt ggtcttgttc agaagcagcc agatttccaa tgttgttttt | 6840 |
| cccctccact cagaaacccc tgcccttttcc cttcagaaaa cgatggcagg cattcctctg | 6900 |
| agtttacaag cagagactca ctccaaccca aactagctgg gagttcagaa ccatggtgga | 6960 |
| ataaagaaat gtgcatctgg tccaaaaaaa aaaaaaaaa aaaaaaaaa aaaaaaa | 7017 |

<210> SEQ ID NO 2
<211> LENGTH: 6442
<212> TYPE: DNA
<213> ORGANISM: Rattus norvegicus

<400> SEQUENCE: 2

| | |
|---|---|
| agaggtccct agacgggaag gggcacgccg ccaggcggga ctgtggagct aacgatggag | 60 |
| agcacctccc tgcgaggtct ccggtgccca cagctctgca gccactctgg cgccatgagg | 120 |
| gcgccgacca ccgtccgctg ctccggacgc atccaaaggg cgcgttggag gggcttcctg | 180 |
| ccacttgtcc tggctctctt gatggggaca agtcatgccc aaagggattc cgtggggaga | 240 |
| tacgaaccag ctagccggga tgccaatcgg ttgtggcgcc ccgtgggcaa ccaccccgca | 300 |
| gcggctgcag ccaaggtgta cagtctgttc cgagagcccg acgcgccggt ccccggcttg | 360 |
| tcgccctctg agtggaatca gccggggcag gggatccctg ggaggctcgc agaggccgag | 420 |
| gccaggagac cgtcccgagc ccagcagctg cgtcgagtcc agtcacctgt ccagactcgg | 480 |
| agaagcaatc cccgaggcca gcagccacca gcagcccgga ccgcacattc cgtcgtgcgc | 540 |
| ctggcgaccc ctcagcgacc cgcggctgca cgccgagggc ggctcaccgg gagaaatgtc | 600 |
| tgcgggggac agtgctgccc tggatggacg acatcgaaca gcaccaacca ctgtatcaaa | 660 |
| cctgtgtgtc agcctccctg tcagaaccgg ggctcctgca gccggcccca gctctgcatc | 720 |
| tgccgttctg gcttccgtgg ggcacgctgc gaggaggtca tccctgagga ggagtttgac | 780 |
| cctcagaatg ccaggcctgt gcccagacgc tcagtggagg gagcacctgg ccctcacagg | 840 |
| agcagcgagg ccagaggaag tctagtgacc agaatacagc cgctgctacc accactacca | 900 |
| ccacctccat ctaggaccct cagccagacc cgtcccctgc agcagcatgc aggactgtcc | 960 |
| agaacagttc gtcgttatcc ggccactggt accaatggcc aactgatgtc caacgctctg | 1020 |
| ccttcaggac caggacctga gctgagagac agcagccaac aggcagcaca catgaaccat | 1080 |
| ctctcacacc cctgggggct gaacctcacc gagaaaatca agaagattaa ggtcgtcttc | 1140 |
| actcccacca tctgcaagca gacctgtgcc cggggccgct gtgccaacac gtgtgagaag | 1200 |
| ggtgacacca ccaccctgta cagtcagggc ggccatgggc atgaccccaa gtctggcttc | 1260 |
| cgtatctatt tctgccaaat cccctgcctg aatgaggcc gctgcattgg ccgggacgag | 1320 |
| tgctggtgtc cagccaactc tacagggaag ttctgccatc tgcctgtccc acagccagac | 1380 |

```
agggagcctc caggacgagg ctcccagcac agagccctgc tggaagggcc attgaagcaa    1440
tccaccttca cgctgcctct ctccaaccag ctggcctctg tgaacccctc gctggtgaag    1500
gtacaaatgc agcacccgcc tgaggcctcc gtgcagatcc accaggtggc ccgggtccgg    1560
ggtgaggtgg accctgtgcc agaggacaac agtgtggaga ccagagcctc tcatcgcccc    1620
catggcagct caggccacag ccactgggcc agcaacagca tacccgctcg ggctggagag    1680
gcccctcggc caccaccagt gccgtccagg cattatggac ttctgggcca gtgttacctg    1740
agcacggtga atggacagtg tgctaacccc ctaggggagc tgacttctca ggaagactgc    1800
tgtggcagtg tggggacttc ttgggggggtg acttcctgtg ccccatgccc acccagacca    1860
gctttccccg tgattgaaaa cggccagctg gagtgtcccc aagggtataa gagactaaac    1920
ctcagccatt gccaagacat caatgagtgc ctgaccctgg gcctgtgcaa ggattcagag    1980
tgtgtgaaca ccaggggcag ctacctgtgc acctgcaggc ccggcctcat gctggatcca    2040
tcaaggagcc gctgtgtatc ggacaaggct gtctccatga acagggact ctgttaccgg    2100 tcaatggtgt ctggcacctg caccctgcct ttggtacaac ggatcaccaa gcagatatgc    2160
tgttgcagcc gtgtgggcaa agcctggggc agcaaatgtg aacactgccc cctgcctggc    2220
acagaagcct tcagggagat ctgccctgct ggccatggct acgcctactc aagctcagac    2280
atccgcctgt ctatgaggaa agctgaggaa gaggaactgg ctagcccgt aagggaacag    2340 agacagcaga gcagtggacc cccacctggg gcagcagaaa ggcagccact ccgggcagcc    2400
actgccacct ggattgaggc tgagaccctc cctgacaaag gtgactctcg ggctattcag    2460
attacaacca gtgctcccca cctacctgcc cgggtaccag gggatgccac tggaagacca    2520
acgccatcat tgcctggaca gggcattcca gagggtccag cagaagagca ggtgatccct    2580
tccagtgatg tcctggtgac gcacggtccc ccaggctttg atccatgttt cgctggagcc    2640
tccaacatct gtggccctgg gacctgtgtg aagctcccaa atggatacag atgtgtctgc    2700
agccctggtt accagctaca ccccagccag gactactgta ctgatgacaa cgagtgtctg    2760 aggaaccccct gtgaaggaag agggcgctgt gtcaacagtg tgggctccta ctcctgcctc    2820
tgctacccag gctacacact agccaccta ggagacacac aggagtgcca agatgtggat    2880
gagtgtgagc agccgggggt gtgcagcggt ggacgatgca gcaacactga gggctcgtac    2940
cactgcgagt gtgatcaggg ctacgtcatg gtcagaagag gacactgcca agatatcaac    3000
gaatgccgtc accctggtac ctgccctgat gggagatgcg tcaactcccc tggctcctac    3060
acttgtctgg cctgtgagga gggctacata gggcagagcg ggaactgtgt agatatgaat    3120
gagtgtctga cccccgggat atgtgcccat ggaaggtgca tcaacatgga aggctccttt    3180
agatgctctt gtgagccagg ctatgagctc acccagaca agaagggctg ccgagatgtg    3240
gacgagtgtg ccagccgagc ctcatgcccc accggcctct gcctcaacac ggagggctcc    3300
ttcacctgct cagcctgtca gagtgggtac tgggtgaacg aagatggcac tgcctgtgaa    3360
gacctggatg aatgtgcctt ccccggagtc tgccccacag cgtctgcac caacactgtg    3420 ggctccttct cctgcaagga ctgcgacagg ggcttccggc ccagcccct gggcaacagc    3480 tgtgaagatg tggatgagtg tgaaggtccc cagaacagct gcctgggagg cgagtgcaag    3540
aacacagatg gttcctacca gtgcctctgt ccccagggct ccagctggc caatggcacc    3600 gtgtgtgagg atgtggacga atgtgttggg gaagaacact gcgctcctca tggcgaatgc    3660
ctcaacagcc cggggtcctt cttctgtctc tgtgcacccg gctttgctag tgctgagggg    3720
ggcaccagat gccaggatgt tgatgaatgt gcaaccacag agccgtgtct gggaggacac    3780
```

```
tgtgtcaaca ccgagggctc cttcaactgt ctgtgtgaga ctggcttcca gcccgcccca   3840
gacagtggag agtgtgtgga catagatgaa tgtgcaaatg atactgtgtg tgggaaccat   3900
ggcttctgtg acaatacgga tggctccttc cgctgcctgt gtgaccaggg cttcgagacc   3960
tcaccctcag gctgggagtg tgttgatgtg aacgagtgtg agctcatgct ggcagtgtgt   4020
ggggatgcac tctgcgagaa cgtggaaggc tccttcctgt gcctttgtgc cagtgacctt   4080
gaggagtatg atgcagaaga aggacactgc cgtcctcggg tggctggagc tcagagaatc   4140
ccagaggtcc aacagagga gcaggctgca ggccttaccg gcatggagtg ctatgctgaa   4200
cacaatggtg gtcctccatg ctctcaaatc ttgggccaga actccacaca ggctgagtgc   4260
tgctcgaccc agggtgccag atgggggaa acctgtgatc cctgcccatc tgaggactca   4320
gttgaattca gtgagctgtg ccccagtggt caaggttaca tcccagtgga aggggcctgg   4380
acatttggac aagccatgta tacagatgcc gacgagtgca tactgtttgg gcctgctctc   4440
tgccagaatg gccgatgcct caacacagtg cctggctaca tttgcctgtg caaccctggc   4500
taccactatg atgccgtcag caggaagtgc caggatcaca acgaatgcca ggacttggcc   4560
tgtgagaacg gcgagtgtgt gaacacagaa ggctccttcc actgcttctg cagtccccc   4620 ctcatcctag acctcagcgg acagcgctgt gtgaacagta ccagcagctc agaggacttc   4680
cctgaccatg acatccacat ggacatctgc tggaaaaaag tcaccaatga cgtgtgcagc   4740
cagcccttgc gtgggcacca tactacctat acagagtgct gctgccaaga cggggaggcc   4800
tggagccagc agtgtgctct gtgccccccc aggagctctg aggtctatgc tcagctgtgc   4860
aatgtggctc ggattgaggc agagagggaa gcagggatcc acttccggcc aggatatgag   4920
tatggccctg gccagatgaa tctacctgaa accctctacg gcccagatgg agccccttc   4980 tataactacc tgggccctga ggacactgtt cctgagcctc ccttctccaa cacagccagt   5040
catttgggag acaacacacc catccttgag cctcccctgc agccctctga acttcagccc   5100
ccagccattc agaacccct ggcttccttc gaaggccttc aggctgagga atgtggcatc   5160
ctgaatggct gtgagaatgg ccgctgtgtg cgtgtgcgcg agggctacac ttgtgactgc   5220
tttgaaggct tccagctgga tacagccctc atggcctgtg tggatgtgaa tgagtgtgaa   5280
gacctgaacg gcgctgcgcg actctgtgcg catggtcact gcgagaacac agagggttcc   5340
tatcgctgcc actgttcccc tggttacgtg gcagagcccg gccccccaca ctgtgcagcc   5400
aaggagtagg agtgagagat catggtgggc agctatgtgg aaatggctat cagccatagg   5460
ctggggactt aaggttgctt ccctagctgg aagacgtga ctgggaagac cccgtgatgc   5520
catcaggcca gggctctgga gcccagttcc gccagcctcg cctccttttt atctcttccg   5580
gcttaactct gggtgtgaat ccgtcactg cctctatgcc actgcttggc tcagacacca   5640
caaatatttt aatgctttag ccactggccg tgagacacag cccacagtct gtcctcgggg   5700 ccacactta gagcgcccat cagaagagtc ctcgtgcact cctcttaggc tgtgcagaca   5760
ctgcaggcac ccccttccat ctgtgatcta cacatcatct cgatggttct gtaacgggga   5820
cagtggctac atccacctgg ggatggccct tcacagtgaa tggagcagga gagggtctgg   5880
ggagtagctc caatgccacc tctcagaacc accaccagca ctgggtggcg tgagttcttt   5940
ttgctactcc tccatcccat agacagttct gcggccccga aagggacca gtttccctca   6000 cctcagagga tgaagactaa tactaacttg ctgagtgtaa gaacgaaag aagaggaata   6060 acgagtctga gaaagtgtgg caagagagtg atacggaaaa catgggagtc catatgaaag   6120
gaggagccaa gagttagaca aaacacgaag tcgctttggg caaatcagtc caagcctcct   6180
```

```
tagagcttct gtgtgcctgc agggaggctc gccacaagct ctggcgccca tctgcaaaca    6240
cctttattag gctcatctgt tccccacagg aaaacctaaa tagatggcct taacaatata    6300
aaggcagagc aagccagatt tttcaaagtt gtttctctcc tccacttcag aagcacttgc    6360
ccttgcttcc tcttaacaca tgcacttcca caccagctag ctgggggttc aggagcgtgg    6420
gggaataaaa tgttcatctg cc                                             6442
```

<210> SEQ ID NO 3
<211> LENGTH: 1821
<212> TYPE: PRT
<213> ORGANISM: Homo sapiens

<400> SEQUENCE: 3

```
Met Arg Pro Arg Thr Lys Ala Arg Ser Pro Gly Arg Ala Leu Arg Asn
 1               5                  10                  15

Pro Trp Arg Gly Phe Leu Pro Leu Thr Leu Ala Leu Phe Val Gly Ala
            20                  25                  30

Gly His Ala Gln Arg Asp Pro Val Gly Arg Tyr Glu Pro Ala Gly Gly
        35                  40                  45

Asp Ala Asn Arg Leu Arg Arg Pro Gly Gly Ser Tyr Pro Ala Ala Ala
    50                  55                  60

Ala Ala Lys Val Tyr Ser Leu Phe Arg Glu Gln Asp Ala Pro Val Ala
65                  70                  75                  80

Gly Leu Gln Pro Val Glu Arg Ala Gln Pro Gly Trp Gly Ser Pro Arg
                85                  90                  95

Arg Pro Thr Glu Ala Glu Ala Arg Arg Pro Ser Arg Ala Gln Gln Ser
            100                 105                 110

Arg Arg Val Gln Pro Pro Ala Gln Thr Arg Arg Ser Thr Pro Leu Gly
        115                 120                 125

Gln Gln Gln Pro Ala Pro Arg Thr Arg Ala Ala Pro Ala Leu Pro Arg
    130                 135                 140

Leu Gly Thr Pro Gln Arg Ser Gly Ala Ala Pro Pro Thr Pro Pro Arg
145                 150                 155                 160

Gly Arg Leu Thr Gly Arg Asn Val Cys Gly Gln Cys Cys Pro Gly
                165                 170                 175

Trp Thr Thr Ala Asn Ser Thr Asn His Cys Ile Lys Pro Val Cys Glu
            180                 185                 190

Pro Pro Cys Gln Asn Arg Gly Ser Cys Ser Arg Pro Gln Leu Cys Val
        195                 200                 205

Cys Arg Ser Gly Phe Arg Gly Ala Arg Cys Glu Glu Val Ile Pro Asp
    210                 215                 220

Glu Glu Phe Asp Pro Gln Asn Ser Arg Leu Ala Pro Arg Arg Trp Ala
225                 230                 235                 240

Glu Arg Ser Pro Asn Leu Arg Arg Ser Ser Ala Ala Gly Glu Gly Thr
                245                 250                 255

Leu Ala Arg Ala Gln Pro Pro Ala Pro Gln Ser Pro Ala Pro Gln
            260                 265                 270

Ser Pro Pro Ala Gly Thr Leu Ser Gly Leu Ser Gln Thr His Pro Ser
        275                 280                 285

Gln Gln His Val Gly Leu Ser Arg Thr Val Arg Leu His Pro Thr Ala
    290                 295                 300

Thr Ala Ser Ser Gln Leu Ser Ser Asn Ala Leu Pro Pro Gly Pro Gly
305                 310                 315                 320

Leu Glu Gln Arg Asp Gly Thr Gln Gln Ala Val Pro Leu Glu His Pro
```

-continued

```
                325                 330                 335
Ser Ser Pro Trp Gly Leu Asn Leu Thr Glu Lys Ile Lys Lys Ile Lys
            340                 345                 350

Ile Val Phe Thr Pro Thr Ile Cys Lys Gln Thr Cys Ala Arg Gly His
                355                 360                 365

Cys Ala Asn Ser Cys Glu Arg Gly Asp Thr Thr Leu Tyr Ser Gln
    370                 375                 380

Gly Gly His Gly His Asp Pro Lys Ser Gly Phe Arg Ile Tyr Phe Cys
385                 390                 395                 400

Gln Ile Pro Cys Leu Asn Gly Arg Cys Ile Gly Arg Asp Glu Cys
                405                 410                 415

Trp Cys Pro Ala Asn Ser Thr Gly Lys Phe Cys His Leu Pro Ile Pro
            420                 425                 430

Gln Pro Asp Arg Glu Pro Pro Gly Arg Gly Ser Arg Pro Arg Ala Leu
                435                 440                 445

Leu Glu Ala Pro Leu Lys Gln Ser Thr Phe Thr Leu Pro Leu Ser Asn
            450                 455                 460

Gln Leu Ala Ser Val Asn Pro Ser Leu Val Lys Val His Ile His His
465                 470                 475                 480

Pro Pro Glu Ala Ser Val Gln Ile His Gln Val Ala Gln Val Arg Gly
                485                 490                 495

Gly Val Glu Glu Ala Leu Val Glu Asn Ser Val Glu Thr Arg Pro Pro
            500                 505                 510

Pro Trp Leu Pro Ala Ser Pro Gly His Ser Leu Trp Asp Ser Asn Asn
            515                 520                 525

Ile Pro Ala Arg Ser Gly Glu Pro Pro Arg Pro Leu Pro Pro Ala Ala
            530                 535                 540

Pro Arg Pro Arg Gly Leu Leu Gly Arg Cys Tyr Leu Asn Thr Val Asn
545                 550                 555                 560

Gly Gln Cys Ala Asn Pro Leu Leu Glu Leu Thr Thr Gln Glu Asp Cys
                565                 570                 575

Cys Gly Ser Val Gly Ala Phe Trp Gly Val Thr Leu Cys Ala Pro Cys
            580                 585                 590

Pro Pro Arg Pro Ala Ser Pro Val Ile Glu Asn Gly Gln Leu Glu Cys
            595                 600                 605

Pro Gln Gly Tyr Lys Arg Leu Asn Leu Thr His Cys Gln Asp Ile Asn
            610                 615                 620

Glu Cys Leu Thr Leu Gly Leu Cys Lys Asp Ala Glu Cys Val Asn Thr
625                 630                 635                 640

Arg Gly Ser Tyr Leu Cys Thr Cys Arg Pro Gly Leu Met Leu Asp Pro
                645                 650                 655

Ser Arg Ser Arg Cys Val Ser Asp Lys Ala Ile Ser Met Leu Gln Gly
            660                 665                 670

Leu Cys Tyr Arg Ser Leu Gly Pro Gly Thr Cys Thr Leu Pro Leu Ala
            675                 680                 685

Gln Arg Ile Thr Lys Gln Ile Cys Cys Ser Arg Val Gly Lys Ala
            690                 695                 700

Trp Gly Ser Glu Cys Glu Lys Cys Pro Leu Pro Gly Thr Glu Ala Phe
705                 710                 715                 720

Arg Glu Ile Cys Pro Ala Gly His Gly Tyr Thr Tyr Ala Ser Ser Asp
                725                 730                 735

Ile Arg Leu Ser Met Arg Lys Ala Glu Glu Glu Leu Ala Arg Pro
            740                 745                 750
```

-continued

```
Pro Arg Glu Gln Gly Gln Arg Ser Ser Gly Ala Leu Pro Gly Pro Ala
        755                 760                 765
Glu Arg Gln Pro Leu Arg Val Val Thr Asp Thr Trp Leu Glu Ala Gly
770                 775                 780
Thr Ile Pro Asp Lys Gly Asp Ser Gln Ala Gly Gln Val Thr Thr Ser
785                 790                 795                 800
Val Thr His Ala Pro Ala Trp Val Thr Gly Asn Ala Thr Thr Pro Pro
                805                 810                 815
Met Pro Glu Gln Gly Ile Ala Glu Ile Gln Glu Gln Val Thr Pro
                820                 825                 830
Ser Thr Asp Val Leu Val Thr Leu Ser Thr Pro Gly Ile Asp Arg Cys
        835                 840                 845
Ala Ala Gly Ala Thr Asn Val Cys Gly Pro Gly Thr Cys Val Asn Leu
850                 855                 860
Pro Asp Gly Tyr Arg Cys Val Cys Ser Pro Gly Tyr Gln Leu His Pro
865                 870                 875                 880
Ser Gln Ala Tyr Cys Thr Asp Asp Asn Glu Cys Leu Arg Asp Pro Cys
                885                 890                 895
Lys Gly Lys Gly Arg Cys Ile Asn Arg Val Gly Ser Tyr Ser Cys Phe
        900                 905                 910
Cys Tyr Pro Gly Tyr Thr Leu Ala Thr Ser Gly Ala Thr Gln Glu Cys
915                 920                 925
Gln Asp Ile Asn Glu Cys Glu Gln Pro Gly Val Cys Ser Gly Gly Gln
930                 935                 940
Cys Thr Asn Thr Glu Gly Ser Tyr His Cys Glu Cys Gln Gly Tyr
945                 950                 955                 960
Ile Met Val Arg Lys Gly His Cys Gln Asp Ile Asn Glu Cys Arg His
                965                 970                 975
Pro Gly Thr Cys Pro Asp Gly Arg Cys Val Asn Ser Pro Gly Ser Tyr
                980                 985                 990
Thr Cys Leu Ala Cys Glu Glu Gly Tyr Arg Gly Gln Ser Gly Ser Cys
        995                 1000                1005
Val Asp Val Asn Glu Cys Leu Thr Pro Gly Val Cys Ala His Gly Lys
    1010                1015                1020
Cys Thr Asn Leu Glu Gly Ser Phe Arg Cys Ser Cys Glu Gln Gly Tyr
1025                1030                1035                1040
Glu Val Thr Ser Asp Glu Lys Gly Cys Gln Asp Val Asp Glu Cys Ala
                1045                1050                1055
Ser Arg Ala Ser Cys Pro Thr Gly Leu Cys Leu Asn Thr Glu Gly Ser
        1060                1065                1070
Phe Ala Cys Ser Ala Cys Glu Asn Gly Tyr Trp Val Asn Glu Asp Gly
        1075                1080                1085
Thr Ala Cys Glu Asp Leu Asp Glu Cys Ala Phe Pro Gly Val Cys Pro
    1090                1095                1100
Ser Gly Val Cys Thr Asn Thr Ala Gly Ser Phe Ser Cys Lys Asp Cys
1105                1110                1115                1120
Asp Gly Gly Tyr Arg Pro Ser Pro Leu Gly Asp Ser Cys Glu Asp Val
                1125                1130                1135
Asp Glu Cys Glu Asp Pro Gln Ser Ser Cys Leu Gly Gly Glu Cys Lys
        1140                1145                1150
Asn Thr Val Gly Ser Tyr Gln Cys Leu Cys Pro Gln Gly Phe Gln Leu
    1155                1160                1165
Ala Asn Gly Thr Val Cys Glu Asp Val Asn Glu Cys Met Gly Glu Glu
    1170                1175                1180
```

```
His Cys Ala Pro His Gly Glu Cys Leu Asn Ser His Gly Ser Phe Phe
1185                1190                1195                1200

Cys Leu Cys Ala Pro Gly Phe Val Ser Ala Glu Gly Gly Thr Ser Cys
            1205                1210                1215

Gln Asp Val Asp Glu Cys Ala Thr Thr Asp Pro Cys Val Gly His
    1220                1225                1230

Cys Val Asn Thr Glu Gly Ser Phe Asn Cys Leu Cys Glu Thr Gly Phe
            1235                1240                1245

Gln Pro Ser Pro Glu Ser Gly Glu Cys Val Asp Ile Asp Glu Cys Glu
    1250                1255                1260

Asp Tyr Gly Asp Pro Val Cys Gly Thr Trp Lys Cys Glu Asn Ser Pro
1265                1270                1275                1280

Gly Ser Tyr Arg Cys Val Leu Gly Cys Gln Pro Gly Phe His Met Ala
            1285                1290                1295

Pro Asn Gly Asp Cys Ile Asp Ile Asp Glu Cys Ala Asn Asp Thr Met
            1300                1305                1310

Cys Gly Ser His Gly Phe Cys Asp Asn Thr Asp Gly Ser Phe Arg Cys
            1315                1320                1325

Leu Cys Asp Gln Gly Phe Glu Ile Ser Pro Ser Gly Trp Asp Cys Val
1330                1335                1340

Asp Val Asn Glu Cys Glu Leu Met Leu Ala Val Cys Gly Ala Ala Leu
1345                1350                1355                1360

Cys Glu Asn Val Glu Gly Ser Phe Leu Cys Leu Cys Ala Ser Asp Leu
            1365                1370                1375

Glu Glu Tyr Asp Ala Gln Glu Gly His Cys Arg Pro Arg Gly Ala Gly
            1380                1385                1390

Gly Gln Ser Met Ser Glu Ala Pro Thr Gly Asp His Ala Pro Ala Pro
            1395                1400                1405

Thr Arg Met Asp Cys Tyr Ser Gly Gln Lys Gly His Ala Pro Cys Ser
            1410                1415                1420

Ser Val Leu Gly Arg Asn Thr Thr Gln Ala Glu Cys Cys Cys Thr Gln
1425                1430                1435                1440

Gly Ala Ser Trp Gly Asp Ala Cys Asp Leu Cys Pro Ser Glu Asp Ser
            1445                1450                1455

Ala Glu Phe Ser Glu Ile Cys Pro Ser Gly Lys Gly Tyr Ile Pro Val
            1460                1465                1470

Glu Gly Ala Trp Thr Phe Gly Gln Thr Met Tyr Thr Asp Ala Asp Glu
            1475                1480                1485

Cys Val Ile Phe Gly Pro Gly Leu Cys Pro Asn Gly Arg Cys Leu Asn
            1490                1495                1500

Thr Val Pro Gly Tyr Val Cys Leu Cys Asn Pro Gly Phe His Tyr Asp
1505                1510                1515                1520

Ala Ser His Lys Lys Cys Glu Asp His Asp Glu Cys Gln Asp Leu Ala
            1525                1530                1535

Cys Glu Asn Gly Glu Cys Val Asn Thr Glu Gly Ser Phe His Cys Phe
            1540                1545                1550

Cys Ser Pro Pro Leu Thr Leu Asp Leu Ser Gln Gln Arg Cys Met Asn
            1555                1560                1565

Ser Thr Ser Ser Thr Glu Asp Leu Pro Asp His Asp Ile His Met Asp
        1570                1575                1580

Ile Cys Trp Lys Lys Val Thr Asn Asp Val Cys Ser Glu Pro Leu Arg
1585                1590                1595                1600

Gly His Arg Thr Thr Tyr Thr Glu Cys Cys Cys Gln Asp Gly Glu Ala
```

```
               1605                1610                1615
Trp Ser Gln Gln Cys Ala Leu Cys Pro Pro Arg Ser Glu Val Tyr
            1620                1625                1630

Ala Gln Leu Cys Asn Val Ala Arg Ile Glu Ala Glu Arg Glu Ala Gly
            1635                1640                1645

Val His Phe Arg Pro Gly Tyr Glu Tyr Gly Pro Gly Pro Asp Asp Leu
            1650                1655                1660

His Tyr Ser Ile Tyr Gly Pro Asp Gly Ala Pro Phe Tyr Asn Tyr Leu
1665                1670                1675                1680

Gly Pro Glu Asp Thr Val Pro Glu Pro Ala Phe Pro Asn Thr Ala Gly
            1685                1690                1695

His Ser Ala Asp Arg Thr Pro Ile Leu Glu Ser Pro Leu Gln Pro Ser
            1700                1705                1710

Glu Leu Gln Pro His Tyr Val Ala Ser His Pro Glu Pro Pro Ala Gly
            1715                1720                1725

Phe Glu Gly Leu Gln Ala Glu Glu Cys Gly Ile Leu Asn Gly Cys Glu
            1730                1735                1740

Asn Gly Arg Cys Val Arg Val Arg Glu Gly Tyr Thr Cys Asp Cys Phe
1745                1750                1755                1760

Glu Gly Phe Gln Leu Asp Ala Ala His Met Ala Cys Val Asp Val Asn
            1765                1770                1775

Glu Cys Asp Asp Leu Asn Gly Pro Ala Val Leu Cys Val His Gly Tyr
            1780                1785                1790

Cys Glu Asn Thr Glu Gly Ser Tyr Arg Cys His Cys Ser Pro Gly Tyr
            1795                1800                1805

Val Ala Glu Ala Gly Pro Pro His Cys Thr Ala Lys Glu
            1810                1815                1820

<210> SEQ ID NO 4
<211> LENGTH: 1764
<212> TYPE: PRT
<213> ORGANISM: Rattus norvegicus

<400> SEQUENCE: 4

Met Arg Ala Pro Thr Thr Val Arg Cys Ser Gly Arg Ile Gln Arg Ala
1               5                   10                  15

Arg Trp Arg Gly Phe Leu Pro Leu Val Leu Ala Leu Leu Met Gly Thr
            20                  25                  30

Ser His Ala Gln Arg Asp Ser Val Gly Arg Tyr Glu Pro Ala Ser Arg
            35                  40                  45

Asp Ala Asn Arg Leu Trp Arg Pro Val Gly Asn His Pro Ala Ala Ala
            50                  55                  60

Ala Ala Lys Val Tyr Ser Leu Phe Arg Glu Pro Asp Ala Pro Val Pro
65                  70                  75                  80

Gly Leu Ser Pro Ser Glu Trp Asn Gln Pro Gly Gln Gly Ile Pro Gly
            85                  90                  95

Arg Leu Ala Glu Ala Glu Ala Arg Arg Pro Ser Arg Ala Gln Gln Leu
            100                 105                 110

Arg Arg Val Gln Ser Pro Val Gln Thr Arg Arg Ser Asn Pro Arg Gly
            115                 120                 125

Gln Gln Pro Pro Ala Ala Arg Thr Ala His Ser Val Val Arg Leu Ala
            130                 135                 140

Thr Pro Gln Arg Pro Ala Ala Ala Arg Gly Arg Leu Thr Gly Arg
145                 150                 155                 160

Asn Val Cys Gly Gly Gln Cys Cys Pro Gly Trp Thr Thr Ser Asn Ser
```

```
                        165                 170                 175
Thr Asn His Cys Ile Lys Pro Val Cys Gln Pro Cys Gln Asn Arg
            180                 185                 190
Gly Ser Cys Ser Arg Pro Gln Leu Cys Ile Cys Arg Ser Gly Phe Arg
            195                 200                 205
Gly Ala Arg Cys Glu Glu Val Ile Pro Glu Glu Phe Asp Pro Gln
            210                 215                 220
Asn Ala Arg Pro Val Pro Arg Arg Ser Val Gly Ala Pro Gly Pro
225                 230                 235                 240
His Arg Ser Ser Glu Ala Arg Gly Ser Leu Val Thr Arg Ile Gln Pro
            245                 250                 255
Leu Leu Pro Pro Leu Pro Pro Pro Ser Arg Thr Leu Ser Gln Thr
            260                 265                 270
Arg Pro Leu Gln Gln His Ala Gly Leu Ser Arg Thr Val Arg Arg Tyr
            275                 280                 285
Pro Ala Thr Gly Thr Asn Gly Gln Leu Met Ser Asn Ala Leu Pro Ser
            290                 295                 300
Gly Pro Gly Pro Glu Leu Arg Asp Ser Ser Gln Gln Ala Ala His Met
305                 310                 315                 320
Asn His Leu Ser His Pro Trp Gly Leu Asn Leu Thr Glu Lys Ile Lys
            325                 330                 335
Lys Ile Lys Val Val Phe Thr Pro Thr Ile Cys Lys Gln Thr Cys Ala
            340                 345                 350
Arg Gly Arg Cys Ala Asn Thr Cys Glu Lys Gly Asp Thr Thr Leu
            355                 360                 365
Tyr Ser Gln Gly Gly His Gly His Asp Pro Lys Ser Gly Phe Arg Ile
            370                 375                 380
Tyr Phe Cys Gln Ile Pro Cys Leu Asn Gly Gly Arg Cys Ile Gly Arg
385                 390                 395                 400
Asp Glu Cys Trp Cys Pro Ala Asn Ser Thr Gly Lys Phe Cys His Leu
            405                 410                 415
Pro Val Pro Gln Pro Asp Arg Glu Pro Pro Gly Arg Gly Ser Gln His
            420                 425                 430
Arg Ala Leu Leu Glu Gly Pro Leu Lys Gln Ser Thr Phe Thr Leu Pro
            435                 440                 445
Leu Ser Asn Gln Leu Ala Ser Val Asn Pro Ser Leu Val Lys Val Gln
            450                 455                 460
Met Gln His Pro Pro Glu Ala Ser Val Gln Ile His Gln Val Ala Arg
465                 470                 475                 480
Val Arg Gly Glu Val Asp Pro Val Pro Glu Asp Asn Ser Val Glu Thr
            485                 490                 495
Arg Ala Ser His Arg Pro His Gly Ser Ser Gly His Ser His Trp Ala
            500                 505                 510
Ser Asn Ser Ile Pro Ala Arg Ala Gly Glu Ala Pro Arg Pro Pro
            515                 520                 525
Val Pro Ser Arg His Tyr Gly Leu Leu Gly Gln Cys Tyr Leu Ser Thr
            530                 535                 540
Val Asn Gly Gln Cys Ala Asn Pro Leu Gly Glu Leu Thr Ser Gln Glu
545                 550                 555                 560
Asp Cys Cys Gly Ser Val Gly Thr Ser Trp Gly Val Thr Ser Cys Ala
            565                 570                 575
Pro Cys Pro Pro Arg Pro Ala Phe Pro Val Ile Glu Asn Gly Gln Leu
            580                 585                 590
```

```
Glu Cys Pro Gln Gly Tyr Lys Arg Leu Asn Leu Ser His Cys Gln Asp
    595                 600                 605
Ile Asn Glu Cys Leu Thr Leu Gly Leu Cys Lys Asp Ser Glu Cys Val
610                 615                 620
Asn Thr Arg Gly Ser Tyr Leu Cys Thr Cys Arg Pro Gly Leu Met Leu
625                 630                 635                 640
Asp Pro Ser Arg Ser Arg Cys Val Ser Asp Lys Ala Val Ser Met Lys
            645                 650                 655
Gln Gly Leu Cys Tyr Arg Ser Met Val Ser Gly Thr Cys Thr Leu Pro
            660                 665                 670
Leu Val Gln Arg Ile Thr Lys Gln Ile Cys Cys Ser Arg Val Gly
        675                 680                 685
Lys Ala Trp Gly Ser Lys Cys Glu His Cys Pro Leu Pro Gly Thr Glu
    690                 695                 700
Ala Phe Arg Glu Ile Cys Pro Ala Gly His Gly Tyr Ala Tyr Ser Ser
705                 710                 715                 720
Ser Asp Ile Arg Leu Ser Met Arg Lys Ala Glu Glu Glu Leu Ala
            725                 730                 735
Ser Pro Val Arg Glu Gln Arg Gln Ser Ser Gly Pro Pro Gly
            740                 745                 750
Ala Ala Glu Arg Gln Pro Leu Arg Ala Ala Thr Ala Thr Trp Ile Glu
            755                 760                 765
Ala Glu Thr Leu Pro Asp Lys Gly Asp Ser Arg Ala Ile Gln Ile Thr
770                 775                 780
Thr Ser Ala Pro His Leu Pro Ala Arg Val Pro Gly Asp Ala Thr Gly
785                 790                 795                 800
Arg Pro Thr Pro Ser Leu Pro Gly Gln Gly Ile Pro Glu Gly Pro Ala
            805                 810                 815
Glu Glu Gln Val Ile Pro Ser Ser Asp Val Leu Val Thr His Gly Pro
            820                 825                 830
Pro Gly Phe Asp Pro Cys Phe Ala Gly Ala Ser Asn Ile Cys Gly Pro
    835                 840                 845
Gly Thr Cys Val Lys Leu Pro Asn Gly Tyr Arg Cys Val Cys Ser Pro
850                 855                 860
Gly Tyr Gln Leu His Pro Ser Gln Asp Tyr Cys Thr Asp Asp Asn Glu
865                 870                 875                 880
Cys Leu Arg Asn Pro Cys Glu Gly Arg Gly Arg Cys Val Asn Ser Val
            885                 890                 895
Gly Ser Tyr Ser Cys Leu Cys Tyr Pro Gly Tyr Thr Leu Ala Thr Leu
            900                 905                 910
Gly Asp Thr Gln Glu Cys Gln Asp Val Asp Glu Cys Glu Gln Pro Gly
            915                 920                 925
Val Cys Ser Gly Gly Arg Cys Ser Asn Thr Glu Gly Ser Tyr His Cys
    930                 935                 940
Glu Cys Asp Gln Gly Tyr Val Met Val Arg Arg Gly His Cys Gln Asp
945                 950                 955                 960
Ile Asn Glu Cys Arg His Pro Gly Thr Cys Pro Asp Gly Arg Cys Val
            965                 970                 975
Asn Ser Pro Gly Ser Tyr Thr Cys Leu Ala Cys Glu Glu Gly Tyr Ile
            980                 985                 990
Gly Gln Ser Gly Asn Cys Val Asp Met Asn Glu Cys Leu Thr Pro Gly
            995                 1000                1005
Ile Cys Ala His Gly Arg Cys Ile Asn Met Glu Gly Ser Phe Arg Cys
    1010                1015                1020
```

```
Ser Cys Glu Pro Gly Tyr Glu Leu Thr Pro Asp Lys Lys Gly Cys Arg
1025                1030                1035                1040

Asp Val Asp Glu Cys Ala Ser Arg Ala Ser Cys Pro Thr Gly Leu Cys
            1045                1050                1055

Leu Asn Thr Glu Gly Ser Phe Thr Cys Ser Ala Cys Gln Ser Gly Tyr
        1060                1065                1070

Trp Val Asn Glu Asp Gly Thr Ala Cys Glu Asp Leu Asp Glu Cys Ala
    1075                1080                1085

Phe Pro Gly Val Cys Pro Thr Gly Val Cys Thr Asn Thr Val Gly Ser
1090                1095                1100

Phe Ser Cys Lys Asp Cys Asp Arg Gly Phe Arg Pro Ser Pro Leu Gly
1105                1110                1115                1120

Asn Ser Cys Glu Asp Val Asp Cys Glu Gly Pro Gln Asn Ser Cys
        1125                1130                1135

Leu Gly Gly Glu Cys Lys Asn Thr Asp Gly Ser Tyr Gln Cys Leu Cys
            1140                1145                1150

Pro Gln Gly Phe Gln Leu Ala Asn Gly Thr Val Cys Glu Asp Val Asp
        1155                1160                1165

Glu Cys Val Gly Glu Glu His Cys Ala Pro His Gly Glu Cys Leu Asn
    1170                1175                1180

Ser Pro Gly Ser Phe Phe Cys Leu Cys Ala Pro Gly Phe Ala Ser Ala
1185                1190                1195                1200

Glu Gly Gly Thr Arg Cys Gln Asp Val Asp Glu Cys Ala Thr Thr Glu
            1205                1210                1215

Pro Cys Leu Gly Gly His Cys Val Asn Thr Glu Gly Ser Phe Asn Cys
        1220                1225                1230

Leu Cys Glu Thr Gly Phe Gln Pro Ala Pro Asp Ser Gly Glu Cys Val
        1235                1240                1245

Asp Ile Asp Glu Cys Ala Asn Asp Thr Val Cys Gly Asn His Gly Phe
    1250                1255                1260

Cys Asp Asn Thr Asp Gly Ser Phe Arg Cys Leu Cys Asp Gln Gly Phe
1265                1270                1275                1280

Glu Thr Ser Pro Ser Gly Trp Glu Cys Val Asp Val Asn Glu Cys Glu
            1285                1290                1295

Leu Met Leu Ala Val Cys Gly Asp Ala Leu Cys Glu Asn Val Glu Gly
        1300                1305                1310

Ser Phe Leu Cys Leu Cys Ala Ser Asp Leu Glu Glu Tyr Asp Ala Glu
        1315                1320                1325

Glu Gly His Cys Arg Pro Arg Val Ala Gly Ala Gln Arg Ile Pro Glu
    1330                1335                1340

Val Pro Thr Glu Glu Gln Ala Ala Gly Leu Thr Gly Met Glu Cys Tyr
1345                1350                1355                1360

Ala Glu His Asn Gly Gly Pro Pro Cys Ser Gln Ile Leu Gly Gln Asn
            1365                1370                1375

Ser Thr Gln Ala Glu Cys Cys Ser Thr Gln Gly Ala Arg Trp Gly Glu
        1380                1385                1390

Thr Cys Asp Pro Cys Pro Ser Glu Asp Ser Val Glu Phe Ser Glu Leu
        1395                1400                1405

Cys Pro Ser Gly Gln Gly Tyr Ile Pro Val Glu Gly Ala Trp Thr Phe
    1410                1415                1420

Gly Gln Ala Met Tyr Thr Asp Ala Asp Glu Cys Ile Leu Phe Gly Pro
1425                1430                1435                1440

Ala Leu Cys Gln Asn Gly Arg Cys Leu Asn Thr Val Pro Gly Tyr Ile
```

Cys Leu Cys Asn Pro Gly Tyr His Tyr Asp Ala Val Ser Arg Lys Cys
    1445                1450                1455
                1460                1465                1470

Gln Asp His Asn Glu Cys Gln Asp Leu Ala Cys Glu Asn Gly Glu Cys
                1475                1480                1485

Val Asn Thr Glu Gly Ser Phe His Cys Phe Cys Ser Pro Pro Leu Ile
            1490                1495                1500

Leu Asp Leu Ser Gly Gln Arg Cys Val Asn Ser Thr Ser Ser Ser Glu
1505                1510                1515                1520

Asp Phe Pro Asp His Asp Ile His Met Asp Ile Cys Trp Lys Lys Val
                    1525                1530                1535

Thr Asn Asp Val Cys Ser Gln Pro Leu Arg Gly His His Thr Thr Tyr
                1540                1545                1550

Thr Glu Cys Cys Cys Gln Asp Gly Glu Ala Trp Ser Gln Gln Cys Ala
            1555                1560                1565

Leu Cys Pro Pro Arg Ser Ser Glu Val Tyr Ala Gln Leu Cys Asn Val
        1570                1575                1580

Ala Arg Ile Glu Ala Glu Arg Glu Ala Gly Ile His Phe Arg Pro Gly
1585                1590                1595                1600

Tyr Glu Tyr Gly Pro Gly Pro Asp Asp Leu Pro Glu Thr Leu Tyr Gly
                1605                1610                1615

Pro Asp Gly Ala Pro Phe Tyr Asn Tyr Leu Gly Pro Glu Asp Thr Val
            1620                1625                1630

Pro Glu Pro Pro Phe Ser Asn Thr Ala Ser His Leu Gly Asp Asn Thr
        1635                1640                1645

Pro Ile Leu Glu Pro Pro Leu Gln Pro Ser Glu Leu Gln Pro Pro Ala
    1650                1655                1660

Ile Gln Asn Pro Leu Ala Ser Phe Glu Gly Leu Gln Ala Glu Glu Cys
1665                1670                1675                1680

Gly Ile Leu Asn Gly Cys Glu Asn Gly Arg Cys Val Arg Val Arg Glu
                1685                1690                1695

Gly Tyr Thr Cys Asp Cys Phe Glu Gly Phe Gln Leu Asp Thr Ala Leu
            1700                1705                1710

Met Ala Cys Val Asp Val Asn Glu Cys Glu Asp Leu Asn Gly Ala Ala
        1715                1720                1725

Arg Leu Cys Ala His Gly His Cys Glu Asn Thr Glu Gly Ser Tyr Arg
    1730                1735                1740

Cys His Cys Ser Pro Gly Tyr Val Ala Glu Pro Gly Pro Pro His Cys
1745                1750                1755                1760

Ala Ala Lys Glu

<210> SEQ ID NO 5
<211> LENGTH: 21
<212> TYPE: DNA
<213> ORGANISM: Artificial
<220> FEATURE:
<223> OTHER INFORMATION: primer 1

<400> SEQUENCE: 5
cgagatctgc cctagtggaa a                                              21

<210> SEQ ID NO 6
<211> LENGTH: 21
<212> TYPE: DNA
<213> ORGANISM: Artificial
<220> FEATURE:
<223> OTHER INFORMATION: primer 2

```
<400> SEQUENCE: 6
ggcccgaata tcacacactc a                                              21

<210> SEQ ID NO 7
<211> LENGTH: 23
<212> TYPE: DNA
<213> ORGANISM: Artificial
<220> FEATURE:
<223> OTHER INFORMATION: probe 1

<400> SEQUENCE: 7
agcctggacg tttggacaga cca                                            23

<210> SEQ ID NO 8
<211> LENGTH: 21
<212> TYPE: DNA
<213> ORGANISM: Artificial
<220> FEATURE:
<223> OTHER INFORMATION: primer 3

<400> SEQUENCE: 8
cacttgtgac tgctttgaag g                                              21

<210> SEQ ID NO 9
<211> LENGTH: 20
<212> TYPE: DNA
<213> ORGANISM: Artificial
<220> FEATURE:
<223> OTHER INFORMATION: primer 4

<400> SEQUENCE: 9
cccgttcagg tcttcacact                                                20

<210> SEQ ID NO 10
<211> LENGTH: 25
<212> TYPE: DNA
<213> ORGANISM: Artificial
<220> FEATURE:
<223> OTHER INFORMATION: probe 2

<400> SEQUENCE: 10
ctcatggcct gtgtggatgt gaatg                                          25
```